US008598226B2

(12) United States Patent
Yasuma et al.

(10) Patent No.: US 8,598,226 B2
(45) Date of Patent: Dec. 3, 2013

(54) FUSED CYCLIC COMPOUNDS

(71) Applicant: Takeda Pharmaceutical Company Limited, Osaka (JP)

(72) Inventors: Tsuneo Yasuma, Osaka (JP); Nobuyuki Negoro, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/910,374

(22) Filed: Jun. 5, 2013

(65) Prior Publication Data

US 2013/0267589 A1    Oct. 10, 2013

Related U.S. Application Data

(62) Division of application No. 13/287,639, filed on Nov. 2, 2011, now Pat. No. 8,492,430, which is a division of application No. 12/659,695, filed on Mar. 17, 2010, now Pat. No. 8,088,821, which is a division of application No. 12/308,699, filed as application No. PCT/JP2007/063208 on Jun. 26, 2007, now Pat. No. 7,732,626.

(30) Foreign Application Priority Data

Jun. 27, 2006 (JP) .................. 2006-177099

(51) Int. Cl.
*A61K 31/343* (2006.01)
(52) U.S. Cl.
USPC .......................................... 514/469
(58) Field of Classification Search
USPC .......................................... 514/469
See application file for complete search history.

(56) References Cited

U.S. PATENT DOCUMENTS

| | | | |
|---|---|---|---|
| 5,504,213 A | 4/1996 | Fischer et al. | |
| 5,565,446 A | 10/1996 | Boschelli et al. | |
| 5,612,330 A | 3/1997 | Connor et al. | |
| 2002/0143017 A1 | 10/2002 | Mylari | |
| 2003/0004161 A1 | 1/2003 | Bebbington et al. | |
| 2003/0004164 A1 | 1/2003 | Bebbington et al. | |
| 2003/0022885 A1 | 1/2003 | Bebbington et al. | |
| 2003/0036543 A1 | 2/2003 | Bebbington et al. | |
| 2003/0055044 A1 | 3/2003 | Davies et al. | |
| 2003/0055068 A1 | 3/2003 | Bebbington et al. | |
| 2003/0064981 A1 | 4/2003 | Dnegtel et al. | |
| 2003/0064982 A1 | 4/2003 | Davies et al. | |
| 2003/0073687 A1 | 4/2003 | Bebbington et al. | |
| 2003/0078166 A1 | 4/2003 | Davies et al. | |
| 2003/0078275 A1 | 4/2003 | Bebbington et al. | |
| 2003/0083327 A1 | 5/2003 | Davies et al. | |
| 2003/0096249 A1 | 5/2003 | Westphal et al. | |
| 2003/0105090 A1 | 6/2003 | Bebbington et al. | |
| 2003/0162784 A1 | 8/2003 | Mylari | |
| 2003/0225283 A1 | 12/2003 | Corbett et al. | |
| 2004/0097501 A1 | 5/2004 | Bebbington et al. | |
| 2004/0102634 A1 | 5/2004 | Matsuura et al. | |
| 2004/0116454 A1 | 6/2004 | Davies et al. | |
| 2004/0132781 A1 | 7/2004 | Bebbington et al. | |
| 2004/0157893 A1 | 8/2004 | Bebbington et al. | |
| 2004/0167141 A1 | 8/2004 | Bebbington et al. | |
| 2004/0214814 A1 | 10/2004 | Bebbington et al. | |
| 2004/0224944 A1 | 11/2004 | Bebbington et al. | |
| 2005/0004110 A1 | 1/2005 | Bebbington et al. | |
| 2005/0038023 A1 | 2/2005 | Bebbington et al. | |
| 2005/0113381 A1 | 5/2005 | Mylari | |
| 2006/0178429 A1 | 8/2006 | Corbett et al. | |
| 2006/0258658 A1 | 11/2006 | Bebbington et al. | |
| 2006/0258722 A1 | 11/2006 | Yasuma et al. | |
| 2007/0037807 A1 | 2/2007 | Oi et al. | |
| 2007/0105959 A1 | 5/2007 | Kusuda et al. | |
| 2007/0270444 A1 | 11/2007 | Bebbington et al. | |
| 2008/0132563 A1 | 6/2008 | Kakinuma et al. | |
| 2008/0188502 A1 | 8/2008 | Burrows et al. | |
| 2008/0269220 A1 | 10/2008 | Yasuma et al. | |
| 2008/0287444 A1 | 11/2008 | Bebbington et al. | |
| 2009/0088419 A1 | 4/2009 | Maezaki et al. | |

(Continued)

FOREIGN PATENT DOCUMENTS

AP    2009 10287    2/2006
EP    1 559 422    8/2005

(Continued)

OTHER PUBLICATIONS

International Search Report issued Jul. 17, 2009 in International (PCT) Application PCT/JP2007/063208.
Bravo, Pierfrancesco et al., "Electron Impact Mass Spectrometry of Some 2, 3-Dihydro-1-benzofuran-3-acetic Acids," Organic Mass Spectrometry, 1985, vol. 20, No. 1, pp. 53-57.
Haeflinger, Walter von et al., "Stereospezifische Synthese einer neuen Morphin-Teilstruktur," Helvetica Chemica Acta, 1982, vol. 65, No. 6, pp. 1837-1852.
Communication Relating to the Results of the Partial International Search (Form PCT/ISA/206) in International Application No. PCT/JP2007/063208.

(Continued)

*Primary Examiner* — Taofiq A Solola
(74) *Attorney, Agent, or Firm* — Wenderoth, Lind & Ponack, L.L.P.

(57) ABSTRACT

The present invention provides a compound represented by the formula (I):

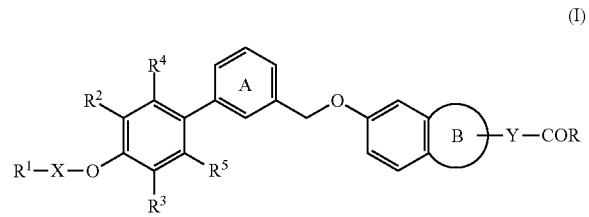

(I)

wherein each symbol is as defined in the description, or a salt thereof. The compound or a salt thereof or a prodrug thereof has a GPR40 receptor function modulating action and is useful as an insulin secretagogue or an agent for the prophylaxis or treatment of diabetes and the like.

1 Claim, No Drawings

(56) References Cited

U.S. PATENT DOCUMENTS

| | | |
|---|---|---|
| 2009/0105257 A1 | 4/2009 | Corbett et al. |
| 2009/0170894 A1 | 7/2009 | Aletru et al. |
| 2009/0176775 A1 | 7/2009 | Braun et al. |
| 2009/0312543 A1 | 12/2009 | Bebbington et al. |

FOREIGN PATENT DOCUMENTS

| | | |
|---|---|---|
| EP | 1 630 152 | 3/2006 |
| EP | 1 698 624 | 9/2006 |
| EP | 1 726 580 | 11/2006 |
| EP | 1 731 505 | 12/2006 |
| JP | 2003-261491 | 9/2003 |
| RU | 2 125 564 | 1/1999 |
| RU | 006023 | 8/2005 |
| RU | 2 340 611 | 12/2008 |
| RU | 2 387 649 | 2/2009 |
| RU | 011297 | 2/2009 |
| RU | 2 353 617 | 4/2009 |
| WO | 00/64876 | 11/2000 |
| WO | 01/14358 | 3/2001 |
| WO | 2004/041266 | 5/2004 |
| WO | 2004/091604 | 10/2004 |
| WO | 2004/106276 | 12/2004 |
| WO | 2005/051890 | 6/2005 |
| WO | 2005/063729 | 7/2005 |
| WO | 2005/087710 | 9/2005 |

OTHER PUBLICATIONS

Notification of Transmittal of the International Search Report and the Written Opinion of the Searching Authority (Jul. 17, 2009).

Written Opinion of the International Searching Authority (Jul. 17, 2009).

X. Cui et al., "Catalytic Homogeneous Asymmetric Hydrogenations of Largely Unfunctionalized Alkenes", Chemical Reviews, vol. 105, No. 9, pp. 3272-3296, 2005.

P. Barbaro et al., "Progress in stereoselective catalysis by metal complexes with chiral ferrocenyl phosphines", Coordination Chemistry Reviews, vol. 248, No. 21-24, pp. 2131-2150, Dec. 1, 2004.

M. J. Burk et al., "Modular Phospholane Ligands in Asymmetric Catalysis", Accounts of Chemical Research, vol. 33, No. 6, pp. 363-372, 2000.

P. Bravo et al., "Electron Impact Mass Spectrometry of Some 2,3-Dihydro-1-benzofuran-3-acetic Acids," Organic Mass Spectrometry, vol. 20, No. 1, pp. 53-57, 1985.

Examiner's Report and an English translation thereof issued in the corresponding Chilean Patent Application No. 1873-2007 (Sep. 28, 2007).

Search Report issued in corresponding Georgian Patent Application No. AP 2007/0011077 (with English translation) (Sep. 8, 2009).

Decision of Grant in corresponding Russian Application No. 2009102515 issued Sep. 19, 2011 (with English translation).

King, Med. Chem. (1994) pp. 206-208.

Office Action received Sep. 24, 2012 in corresponding Costa Rican Application No. 10564, with English translation.

FUSED CYCLIC COMPOUNDS

This application is a Divisional of U.S. application Ser. No. 13/287,639, filed Nov. 2, 2011, now allowed, which is a Divisional of U.S. application Ser. No. 12/659,695, filed Mar. 17, 2010, now U.S. Pat. No. 8,088,821, which is a Divisional of U.S. application Ser. No. 12/308,699, filed Apr. 21, 2009, now U.S. Pat. No. 7,732,626, which is a national stage application of International application No. PCT/JP2007/063208 filed Jun. 26, 2007.

TECHNICAL FIELD

The present invention relates to novel fused cyclic compounds having a GPR40 receptor function modulating action.

BACKGROUND OF THE INVENTION

As GPR40 receptor agonists useful as agents for the prophylaxis or treatment of diabetes and the like, the following compounds have been reported.

(1) WO2004/041266 discloses a GPR40 receptor function regulator comprising a compound having an aromatic ring and a group capable of releasing cation.

(2) WO2004/106276 discloses a compound represented by the following formula (I):

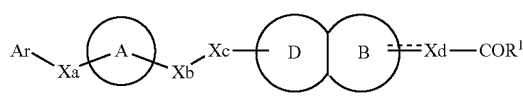

wherein

Ar is an optionally substituted cyclic group;

ring A is an optionally substituted ring (the ring should not be thiazole, oxazole, imidazole and pyrazole);

Xa and Xb are each a bond or a spacer having 1 to 5 atoms in the main chain;

Xc is O, S, SO or $SO_2$;

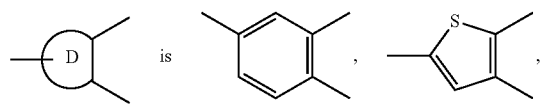

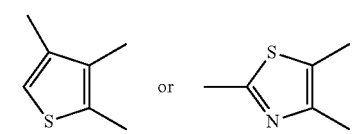

ring B is a 5- to 7-membered ring;

Xd is a bond, CH or $CH_2$; and $R^1$ is an optionally substituted hydroxy group.

(3) WO2005/063729 discloses a compound represented by the following formula (I):

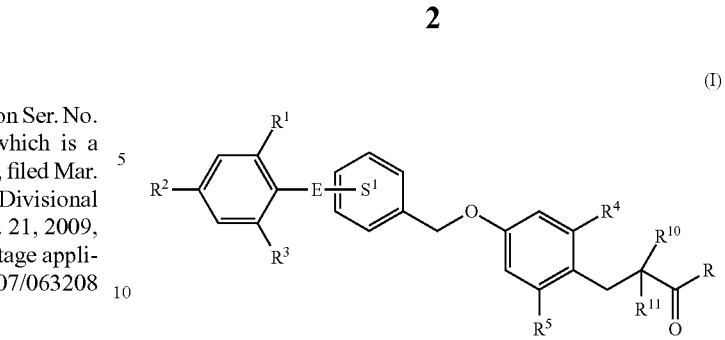

wherein $R^1$, $R^3$, $R^4$ and $R^5$ are each a hydrogen atom, a halogen atom, an optionally substituted hydrocarbon group or an optionally substituted hydroxy group;

$R^{10}$ and $R^{11}$ are each a hydrogen atom, a halogen atom or a $C_{1-6}$ alkoxy group;

R is an optionally substituted hydroxy group or an optionally substituted amino group;

$R^2$ is a halogen atom, a nitro group, an optionally substituted hydrocarbon group, an optionally substituted hydroxy group, an optionally substituted amino group, an optionally substituted mercapto group, an optionally substituted acyl group or an optionally substituted heterocyclic group;

E is a bond, an optionally substituted $C_{1-4}$ alkylene group, —$W^1$—O—$W^2$—, —$W^1$—S—$W^2$— or —$W^1$—N($R^6$)—$W^2$— (wherein $W^1$ and $W^2$ are each a bond or an optionally substituted $C_{1-3}$ alkylene group, and $R^6$ is a hydrogen atom, an optionally substituted acyl group or an optionally substituted hydrocarbon group); and ring $S^1$ is optionally further substituted by substituent(s) selected from a halogen atom, an optionally substituted hydrocarbon group, an optionally substituted hydroxy group and an optionally substituted amino group;

provided that $R^1$ and $R^3$ should not be simultaneously H.

However, none of the documents concretely disclose the compounds of the present invention.

As dihydrobenzofuran compounds useful as synthetic intermediates, the following compounds have been reported.

(1) WO2004/106276 discloses methyl (6-hydroxy-2,3-dihydro-1-benzofuran-3-yl)acetate.

(2) Helvetica Chimica Acta (1982), 65(6), 1837-1852 discloses optical resolution of 7-methoxy-3-(carboxymethyl)-2,3-dihydrobenzofuran.

(3) WO01/14358 discloses optical resolution of 3-(carboxymethyl)-2,3-dihydrobenzofuran.

DISCLOSURE OF THE INVENTION

The present invention aims at providing novel fused cyclic compounds having a GPR40 receptor function modulating action, which are useful as insulin secretagogues or agents for the prophylaxis or treatment of diabetes and the like.

The present inventors have intensively conducted various studies and found that the compounds represented by the following formula (I) unexpectedly have a superior GPR40 receptor agonist activity, show superior properties as pharmaceutical products such as stability and the like, particularly have low toxicity, and show good pharmacokinetics such as blood sustainability and the like, based on the specific chemical structure thereof, and therefore, can be safe and useful pharmaceutical agents for the prophylaxis or treatment of GPR40 receptor-related pathology or diseases in mammals, which resulted in the completion of the present invention.

Accordingly, the present invention relates to

[1] a compound represented by the formula (I):

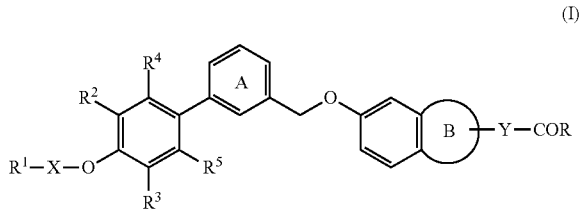

wherein
$R^1$ is $R^6—SO_2—$ (wherein $R^6$ is a substituent) or an optionally substituted 1,1-dioxidotetrahydrothiopyranyl group;
X is a bond or a divalent hydrocarbon group;
$R^2$ and $R^3$ are the same or different and each is a hydrogen atom, a halogen atom, an optionally substituted hydrocarbon group or an optionally substituted hydroxy group;
$R^4$ and $R^5$ are the same or different and each is a $C_{1-6}$ alkyl group optionally substituted by hydroxy group(s);
ring A is a benzene ring optionally further having substituent(s) selected from a halogen atom, an optionally substituted hydrocarbon group, an optionally substituted hydroxy group and an optionally substituted amino group;
ring B is a 5- to 7-membered ring;
Y is a bond or $CH_2$; and
R is an optionally substituted hydroxy group,
or a salt thereof (hereinafter be abbreviated as compound (I));
[2] compound (I) wherein $R^1$ is $R^6—SO_2—$ (wherein $R^6$ is a substituent);
[3] the compound of the above-mentioned [2], wherein $R^6$ is a $C_{1-6}$ alkyl group;
[4] compound (I) wherein X is a $C_{1-6}$ alkylene group;
compound (I) wherein $R^2$ and $R^3$ are the same or different and each is a hydrogen atom, a halogen atom or a $C_{1-6}$ alkyl group;
[6] compound (I) wherein $R^4$ and $R^5$ are the same or different and each is a $C_{1-6}$ alkyl group;
[7] compound (I) wherein ring A is an unsubstituted benzene ring;
[8] compound (I) wherein ring B is tetrahydrofuran;
[9] compound (I) wherein Y is $CH_2$;
[10] compound (I) wherein R is a hydroxy group;
[11] compound (I) which is selected from
[(3S)-6-({4'-[(4-hydroxy-1,1-dioxidotetrahydro-2H-thiopyran-4-yl)methoxy]-2',6'-dimethylbiphenyl-3-yl}methoxy)-2,3-dihydro-1-benzofuran-3-yl]acetic acid,
[(3S)-6-({2',6'-dimethyl-4'-[3-(methylsulfonyl)propoxy]biphenyl-3-yl}methoxy)-2,3-dihydro-1-benzofuran-3-yl]acetic acid,
[(3S)-6-({3'-fluoro-2',6'-dimethyl-4'-[3-(methylsulfonyl)propoxy]biphenyl-3-yl}methoxy)-2,3-dihydro-1-benzofuran-3-yl]acetic acid,
[(3S)-6-({3'-chloro-2',6'-dimethyl-4'-[3-(methylsulfonyl)propoxy]biphenyl-3-yl}methoxy)-2,3-dihydro-1-benzofuran-3-yl]acetic acid,
[(3S)-6-({3',5'-dichloro-2',6'-dimethyl-4'-[3-(methylsulfonyl)propoxy]biphenyl-3-yl}methoxy)-2,3-dihydro-1-benzofuran-3-yl]acetic acid, and
[(3S)-6-({2',6'-diethyl-4'-[3-(methylsulfonyl)propoxy]biphenyl-3-yl}methoxy)-2,3-dihydro-1-benzofuran-3-yl]acetic acid;
[12] a prodrug of compound (I);
[13] a GPR40 receptor function modulator comprising compound (I) or a prodrug thereof;
[14] a pharmaceutical agent comprising compound (I) or a prodrug thereof;
[15] the pharmaceutical agent of the above-mentioned [14], which is an agent for the prophylaxis or treatment of diabetes;
[16] a method for the prophylaxis or treatment of diabetes in a mammal, which comprises administering an effective amount of compound (I) or a prodrug thereof to the mammal;
[17] use of compound (I) or a prodrug thereof for the production of an agent for the prophylaxis or treatment of diabetes;
[18] (6-Hydroxy-2,3-dihydro-1-benzofuran-3-yl)acetic acid or a salt thereof;
[19] a production method of an optically active form of a compound represented by the formula (III):

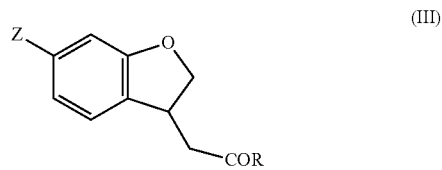

wherein
Z is a halogen atom or an optionally substituted hydroxy group; and
R is an optionally substituted hydroxy group,
or a salt thereof (hereinafter be abbreviated as compound (III)), which comprises subjecting a compound represented by the formula (II):

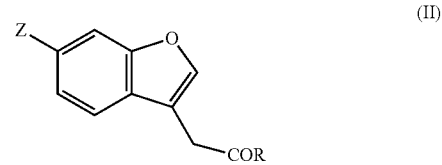

wherein each symbol is as defined above,
or a salt thereof (hereinafter be abbreviated as compound (II)) to an asymmetric reduction reaction; and the like.

The compounds of the present invention have a superior GPR40 receptor agonist activity, show superior properties as pharmaceutical products such as stability and the like, particularly have low toxicity and show good kinetics such as blood sustainability and the like, and therefore, can be safe and useful for the prophylaxis or treatment of GPR40 receptor-related pathology or diseases in mammals.

DETAILED DESCRIPTION OF THE INVENTION

Unless otherwise specified, as the "halogen atom" in the present specification, a fluorine atom, a chlorine atom, a bromine atom and an iodine atom can be mentioned.

Unless otherwise specified, as the "optionally substituted hydrocarbon group" in the present specification, for example, an "optionally substituted $C_{1-6}$ alkyl group", an "optionally substituted $C_{2-6}$ alkenyl group", an "optionally substituted $C_{2-6}$ alkynyl group", an "optionally substituted $C_{3-8}$ cycloalkyl group", an "optionally substituted $C_{6-14}$ aryl group", an "optionally substituted $C_{7-16}$ aralkyl group" and the like can be mentioned.

Unless otherwise specified, as the "$C_{1-6}$ alkyl group" in the present specification, for example, methyl, ethyl, propyl, isopropyl, butyl, isobutyl, sec-butyl, tert-butyl, pentyl, isopentyl, neopentyl, hexyl and the like can be mentioned.

Unless otherwise specified, as the "$C_{2-6}$ alkenyl group" in the present specification, for example, vinyl, propenyl, isopropenyl, 2-buten-1-yl, 4-penten-1-yl, 5-hexen-1-yl and the like can be mentioned.

Unless otherwise specified, as the "$C_{2-6}$ alkynyl group" in the present specification, for example, 2-butyn-1-yl, 4-pentyn-1-yl, 5-hexyn-1-yl and the like can be mentioned.

Unless otherwise specified, as the "$C_{3-8}$ cycloalkyl group" in the present specification, for example, cyclopropyl, cyclobutyl, cyclopentyl, cyclohexyl and the like can be mentioned.

Unless otherwise specified, as the "$C_{6-14}$ aryl group" in the present specification, for example, phenyl, 1-naphthyl, 2-naphthyl, 2-biphenylyl, 3-biphenylyl, 4-biphenylyl, 2-anthryl and the like can be mentioned. The $C_{6-14}$ aryl may be saturated partially, and as the partially saturated $C_{6-14}$ aryl, for example, tetrahydronaphthyl and the like can be mentioned.

Unless otherwise specified, as the "$C_{7-16}$ aralkyl group" in the present specification, for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl and the like can be mentioned.

Unless otherwise specified, as the "optionally substituted hydroxy group" in the present specification, for example, a "hydroxy group", an "optionally substituted $C_{1-6}$ alkoxy group", an "optionally substituted heterocyclyloxy group", an "optionally substituted $C_{6-14}$ aryloxy group", an "optionally substituted $C_{7-16}$ aralkyloxy group" and the like can be mentioned.

Unless otherwise specified, as the "$C_{1-6}$ alkoxy group" in the present specification, for example, methoxy, ethoxy, propoxy, isopropoxy, butoxy, isobutoxy, tert-butoxy, pentyloxy, hexyloxy and the like can be mentioned.

Unless otherwise specified, as the "$C_{1-6}$ alkoxy-$C_{1-16}$ alkoxy group" in the present specification, for example, methoxymethoxy, methoxyethoxy, ethoxymethoxy, ethoxyethoxy and the like can be mentioned.

As the "heterocyclyloxy group" in the present specification, a hydroxy group substituted by a "heterocyclic group" below can be mentioned. As preferable examples of the heterocyclyloxy group, tetrahydropyranyloxy, thiazolyloxy, pyridyloxy, pyrazolyloxy, oxazolyloxy, thienyloxy, furyloxy and the like can be mentioned.

Unless otherwise specified, as the "$C_{6-14}$ aryloxy group" in the present specification, for example, phenoxy, 1-naphthyloxy, 2-naphthyloxy and the like can be mentioned.

Unless otherwise specified, as the "$C_{7-16}$ aralkyloxy group" in the present specification, for example, benzyloxy, phenethyloxy and the like can be mentioned.

Unless otherwise specified, as the "optionally substituted mercapto group" in the present specification, for example, a "mercapto group", an "optionally substituted $C_{1-6}$ alkylthio group", an "optionally substituted heterocyclylthio group", an "optionally substituted $C_{6-14}$ arylthio group", an "optionally substituted $C_{7-16}$ aralkylthio group" and the like can be mentioned.

Unless otherwise specified, as the "$C_{1-6}$ alkylthio group" in the present specification, for example, methylthio, ethylthio, propylthio, isopropylthio, butylthio, sec-butylthio, tert-butylthio and the like can be mentioned.

Unless otherwise specified, as the "heterocyclylthio group" in the present specification, a mercapto group substituted by a "heterocyclic group" below can be mentioned. As preferable examples of the heterocyclylthio group, tetrahydropyranylthio, thiazolylthio, pyridylthio, pyrazolylthio, oxazolylthio, thienylthio, furylthio and the like can be mentioned.

Unless otherwise specified, as the "$C_{6-14}$ arylthio group" in the present specification, for example, phenylthio, 1-naphthylthio, 2-naphthylthio and the like can be mentioned.

Unless otherwise specified, as the "$C_{7-16}$ aralkylthio group" in the present specification, for example, benzylthio, phenethylthio and the like can be mentioned.

Unless otherwise specified, as the "heterocyclic group" in the present specification, for example, a 5- to 14-membered (monocyclic, bicyclic or tricyclic) heterocyclic group containing, as a ring-constituting atom besides carbon atoms, one or two kinds of 1 to 4 hetero atoms selected from a nitrogen atom, a sulfur atom and an oxygen atom, preferably (i) a 5- to 14-membered (preferably 5- to 10-membered) aromatic heterocyclic group, (ii) a 5- to 10-membered non-aromatic heterocyclic group and the like can be mentioned. Of these, a 5- or 6-membered aromatic heterocyclic group is preferable. Specifically, aromatic heterocyclic groups such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl, 5-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1-triazolyl, 2-triazolyl), tetrazolyl, pyridazinyl (e.g., 3-pyridazinyl, 4-pyridazinyl), isothiazolyl (e.g., 3-isothiazolyl, 4-isothiazolyl, 5-isothiazolyl), isoxazolyl (e.g., 3-isoxazolyl, 4-isoxazolyl, 5-isoxazolyl), indolyl (e.g., 1-indolyl, 2-indolyl, 3-indolyl), 2-benzothiazolyl, 2-benzoxazolyl, benzimidazolyl (e.g., 1-benzimidazolyl, 2-benzimidazolyl), benzo[b]thienyl (e.g., 2-benzo[b]thienyl, 3-benzo[b]thienyl), benzo[b]furanyl (e.g., 2-benzo[b]furanyl, 3-benzo[b]furanyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl) and the like;

non-aromatic heterocyclic groups such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., piperidino, 2-piperidinyl, 3-piperidinyl, 4-piperidinyl), piperazinyl (e.g., 1-piperazinyl, 2-piperazinyl), morpholinyl (e.g., 2-morpholinyl, 3-morpholinyl, morpholino), thiomorpholinyl (e.g., 2-thiomorpholinyl, 3-thiomorpholinyl, thiomorpholino), tetrahydropyranyl and the like, and the like can be mentioned.

Unless otherwise specified, as the "$C_{1-6}$ alkyl-carbonyl group" in the present specification, for example, acetyl, isobutanoyl, isopentanoyl and the like can be mentioned.

Unless otherwise specified, as the "$C_{1-6}$ alkoxy-carbonyl group" in the present specification, for example, methoxycarbonyl, ethoxycarbonyl, propoxycarbonyl, tert-butoxycarbonyl and the like can be mentioned.

Unless otherwise specified, as the "$C_{3-8}$ cycloalkyl-carbonyl group" in the present specification, for example, cyclopentylcarbonyl, cyclohexylcarbonyl and the like can be mentioned.

Unless otherwise specified, as the "$C_{6-14}$ aryl-carbonyl so group" in the present specification, for example, benzoyl, 1-naphthoyl, 2-naphthoyl and the like can be mentioned.

Unless otherwise specified, as the "$C_{7-16}$ aralkyl-carbonyl group" in the present specification, for example, phenylacetyl, 2-phenylpropanoyl and the like can be mentioned.

Unless otherwise specified, as the "$C_{6-14}$ aryloxy-carbonyl group" in the present specification, for example, phenoxycarbonyl, naphthyloxycarbonyl and the like can be mentioned.

Unless otherwise specified, as the "$C_{7-16}$ aralkyloxy-carbonyl group" in the present specification, for example, benzyloxycarbonyl, phenethyloxycarbonyl and the like can be mentioned.

Unless otherwise specified, as the "nitrogen-containing heterocyclyl-carbonyl group" in the present specification, for example, pyrrolidinylcarbonyl, piperidinocarbonyl and the like can be mentioned.

Unless otherwise specified, as the "$C_{1-6}$ alkylsulfonyl group" in the present specification, for example, methylsulfonyl, ethylsulfonyl and the like can be mentioned.

Unless otherwise specified, as the "$C_{6-14}$ arylsulfonyl group" in the present specification, for example, phenylsulfonyl, 1-naphthylsulfonyl, 2-naphthylsulfonyl and the like can be mentioned.

Unless otherwise specified, as the "$C_{1-6}$ alkylsulfinyl group" in the present specification, for example, methylsulfinyl, ethylsulfinyl and the like can be mentioned.

Unless otherwise specified, as the "$C_{6-14}$ arylsulfinyl group" in the present specification, for example, phenylsulfinyl, 1-naphthylsulfinyl, 2-naphthylsulfinyl and the like can be mentioned.

Unless otherwise specified, as the "optionally esterified carboxyl group" in the present specification, for example, a carboxyl group, a $C_{1-6}$ alkoxy-carbonyl group, a $C_{6-14}$ aryloxy-carbonyl group, a $C_{7-16}$ aralkyloxy-carbonyl group and the like so can be mentioned.

Unless otherwise specified, as the "optionally halogenated $C_{1-6}$ alkyl group" in the present specification, the above-mentioned "$C_{1-6}$ alkyl group" optionally substituted by 1 to 5 above-mentioned "halogen atoms" can be mentioned. For example, methyl, ethyl, propyl, isopropyl, butyl, tert-butyl, isobutyl, trifluoromethyl and the like can be mentioned.

Unless otherwise specified, as the "optionally halogenated $C_{1-6}$ alkoxy group" in the present specification, the above-mentioned "$C_{1-6}$ alkoxy group" optionally substituted by 1 to 5 above-mentioned "halogen atoms" can be mentioned. For example, methoxy, ethoxy, isopropoxy, tert-butoxy, trifluoromethoxy and the like can be mentioned.

Unless otherwise specified, as the "mono- or di-$C_{1-6}$ alkyl-amino group" in the present specification, an amino group mono- or di-substituted by the above-mentioned "$C_{1-6}$ alkyl group(s)" can be mentioned. For example, methylamino, ethylamino, propylamino, dimethylamino, diethylamino and the like can be mentioned.

Unless otherwise specified, as the "mono- or di-$C_{6-14}$ aryl-amino group" in the present specification, an amino group mono- or di-substituted by the above-mentioned "$C_{6-14}$ aryl group(s)" can be mentioned. For example, phenylamino, diphenylamino, 1-naphthylamino, 2-naphthylamino and the like can be mentioned.

Unless otherwise specified, as the "mono- or di-$C_{7-16}$ aralkyl-amino group" in the present specification, an amino group mono- or di-substituted by the above-mentioned "$C_{7-16}$ aralkyl group(s)" can be mentioned. For example, benzylamino, phenethylamino and the like can be mentioned.

Unless otherwise specified, as the "N—$C_{1-6}$ alkyl-N—$C_{6-14}$ aryl-amino group" in the present specification, an amino group substituted by the above-mentioned "$C_{1-6}$ alkyl group" and the above-mentioned "$C_{6-14}$ aryl group" can be mentioned. For example, N-methyl-N-phenylamino, N-ethyl-N-phenylamino and the so like can be mentioned.

Unless otherwise specified, as the "N—$C_{1-6}$ alkyl-N—$C_{7-16}$ aralkyl-amino group" in the present specification, an amino group substituted by the above-mentioned "$C_{1-6}$ alkyl group" and the above-mentioned "$C_{7-16}$ aralkyl group" can be mentioned. For example, N-methyl-N-benzylamino, N-ethyl-N-benzylamino and the like can be mentioned.

Unless otherwise specified, as the "mono- or di-$C_{1-6}$ alkyl-carbamoyl group" in the present specification, a carbamoyl group mono- or di-substituted by the above-mentioned "$C_{1-6}$ alkyl group(s)" can be mentioned. For example, methylcarbamoyl, ethylcarbamoyl, dimethylcarbamoyl, diethylcarbamoyl, ethylmethylcarbamoyl and the like can be mentioned.

Unless otherwise specified, as the "mono- or di-$C_{6-14}$ aryl-carbamoyl group" in the present specification, a carbamoyl group mono- or di-substituted by the above-mentioned "$C_{6-14}$ aryl group(s)" can be mentioned. For example, phenylcarbamoyl, 1-naphthylcarbamoyl, 2-naphthylcarbamoyl and the like can be mentioned.

Unless otherwise specified, as the "mono- or di-$C_{3-8}$ cycloalkyl-carbamoyl group" in the present specification, a carbamoyl group mono- or di-substituted by the above-mentioned "$C_{3-8}$ cycloalkyl group(s)" can be mentioned. For example, cyclopropylcarbamoyl and the like can be mentioned.

Unless otherwise specified, as the "mono- or di-$C_{7-16}$ aralkyl-carbamoyl group" in the present specification, a carbamoyl group mono- or di-substituted by the above-mentioned "$C_{7-16}$ aralkyl group(s)" can be mentioned. For example, benzylcarbamoyl and the like can be mentioned.

Unless otherwise specified, as the "mono- or di-5- to 7-membered heterocyclyl-carbamoyl group" in the present specification, a carbamoyl group mono- or di-substituted by 5- to 7-membered heterocyclic group(s) can be mentioned. As the 5- to 7-membered heterocyclic group, a heterocyclic group so containing, as a ring-constituting atom besides carbon atoms, one or two kinds of 1 to 4 hetero atoms selected from a nitrogen atom, a sulfur atom and an oxygen atom can be mentioned. As preferable examples of the "mono- or di-5 to 7-membered heterocyclyl-carbamoyl group", 2-pyridylcarbamoyl, 3-pyridylcarbamoyl, 4-pyridylcarbamoyl, 2-thienylcarbamoyl, 3-thienylcarbamoyl and the like can be mentioned.

Unless otherwise specified, as the "mono- or di-$C_{1-6}$ alkyl-sulfamoyl group" in the present specification, a sulfamoyl group mono- or di-substituted by the above-mentioned "$C_{1-6}$ alkyl group(s)" can be used, for example, methylsulfamoyl, ethylsulfamoyl, dimethylsulfamoyl, diethylsulfamoyl and the like can be mentioned.

Unless otherwise specified, as the "mono- or di-$C_{6-14}$ aryl-sulfamoyl group" in the present specification, a sulfamoyl group mono- or di-substituted by the above-mentioned "$C_{6-14}$ aryl group(s)" can be used, for example, phenylsulfamoyl, diphenylsulfamoyl, 1-naphthylsulfamoyl, 2-naphthylsulfamoyl and the like can be mentioned.

Unless otherwise specified, as the "mono- or di-$C_{7-16}$ aralkyl-sulfamoyl group" in the present specification, a sulfamoyl group mono- or di-substituted by the above-mentioned "$C_{7-16}$ aralkyl group(s)" can be used, for example, benzylsulfamoyl and the like can be mentioned.

Unless otherwise specified, as the "optionally substituted $C_{1-6}$ alkyl group", "optionally substituted $C_{2-6}$ alkenyl group", "optionally substituted $C_{2-6}$ alkynyl group", "optionally substituted $C_{1-6}$ alkoxy group" and "optionally substituted $C_{1-6}$ alkylthio group" in the present specification, for example, a "$C_{1-6}$ alkyl group", a "$C_{2-6}$ alkenyl group", a "$C_{2-6}$ alkynyl group", a "$C_{1-6}$ alkoxy group" and a "$C_{1-6}$ alkylthio group", each of which optionally has 1 to 5 substituents at substitutable positions selected from (1) a halogen atom;
(2) a hydroxy group;
(3) an amino group;
(4) a nitro group;
(5) a cyano group;
(6) a heterocyclic group (preferably furyl, pyridyl, thienyl, pyrazolyl, thiazolyl, oxazolyl) optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(7) a mono- or di-$C_{1-6}$ alkyl-amino group;
(8) a mono- or di-$C_{6-14}$ aryl-amino group;
(9) a mono- or di-$C_{7-16}$ aralkyl-amino group;
(10) an N—$C_{1-6}$ alkyl-N—$C_{6-14}$ aryl-amino group;
(11) an N—$C_{1-6}$ alkyl-N—$C_{7-16}$ aralkyl-amino group;
(12) a $C_{3-8}$ cycloalkyl group;
(13) an optionally halogenated $C_{1-6}$ alkoxy group;
(14) a $C_{1-6}$ alkylthio group;
(15) a $C_{1-6}$ alkylsulfinyl group;
(16) a $C_{1-6}$ alkylsulfonyl group;
(17) an optionally esterified carboxyl group;
(18) a $C_{1-6}$ alkyl-carbonyl group;
(19) a $C_{3-8}$ cycloalkyl-carbonyl group;
(20) a $C_{6-14}$ aryl-carbonyl group;
(21) a carbamoyl group;
(22) a thiocarbamoyl group;
(23) a mono- or di-$C_{1-6}$ alkyl-carbamoyl group;
(24) a mono- or di-$C_{6-14}$ aryl-carbamoyl group;
(25) a mono- or di-5- to 7-membered heterocyclyl-carbamoyl group;
(26) a $C_{1-6}$ alkyl-carbonylamino group (e.g., acetylamino, propionylamino) optionally substituted by carboxyl group(s);
(27) a $C_{6-14}$ aryloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(28) a $C_{6-14}$ aryl group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(29) a heterocyclyloxy group;
(30) a sulfamoyl group;
(31) a mono- or di-$C_{1-6}$ alkyl-sulfamoyl group;
(32) a mono- or di-$C_{6-14}$ aryl-sulfamoyl group;
(33) a $C_{7-16}$ aralkyloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group; and the like, can be mentioned.

As the "optionally substituted $C_{3-8}$ cycloalkyl group", "optionally substituted $C_{6-14}$ aryl group", "optionally substituted $C_{7-16}$ aralkyl group", "optionally substituted heterocyclic group", "optionally substituted heterocyclyloxy group", "optionally substituted $C_{6-14}$ aryloxy group", "optionally substituted $C_{7-16}$ aralkyloxy group", "optionally substituted heterocyclylthio group", "optionally substituted $C_{6-14}$ arylthio group" and "optionally substituted $C_{7-16}$ aralkylthio group" in the present specification, for example, a "$C_{3-8}$ cycloalkyl group", a "$C_{6-14}$ aryl group", a "$C_{7-16}$ aralkyl group", a "heterocyclic group", a "heterocyclyloxy group", a "$C_{6-14}$ aryloxy group", a "$C_{7-16}$ aralkyloxy group", a "heterocyclylthio group", a "$C_{6-14}$ arylthio group" and a "$C_{7-16}$ aralkylthio group", each of which optionally has 1 to 5 substituents at substitutable positions selected from (1) a halogen atom;
(2) a hydroxy group;
(3) an amino group;
(4) a nitro group;
(5) a cyano group;
(6) an optionally substituted $C_{1-6}$ alkyl group;
(7) an optionally substituted $C_{2-6}$ alkenyl group;
(8) an optionally substituted $C_{2-6}$ alkynyl group;
(9) a $C_{6-14}$ aryl group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(10) a $C_{6-14}$ aryloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(11) a $C_{7-16}$ aralkyloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(12) a heterocyclic group (preferably furyl, pyridyl, thienyl, pyrazolyl, thiazolyl, oxazolyl) optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(13) a mono- or di-$C_{1-6}$ alkyl-amino group;
(14) a mono- or di-$C_{6-14}$ aryl-amino group;
(15) a mono- or di-$C_{7-16}$ aralkyl-amino group;
(16) an N—$C_{1-6}$ alkyl-N—$C_{6-14}$ aryl-amino group;
(17) an N—$C_{1-6}$ alkyl-N—$C_{7-16}$ aralkyl-amino group;
(18) a $C_{3-8}$ cycloalkyl group;
(19) an optionally substituted $C_{1-6}$ alkoxy group;
(20) an optionally substituted $C_{1-6}$ alkylthio group;
(21) a $C_{1-6}$ alkylsulfinyl group;
(22) a $C_{1-6}$ alkylsulfonyl group;
(23) an optionally esterified carboxyl group;
(24) a $C_{1-6}$ alkyl-carbonyl group;
(25) a $C_{3-8}$ cycloalkyl-carbonyl group;
(26) a $C_{6-14}$ aryl-carbonyl group;
(27) a carbamoyl group;
(28) a thiocarbamoyl group;
(29) a mono- or di-$C_{1-6}$ alkyl-carbamoyl group;
(30) a mono- or di-$C_{6-14}$ aryl-carbamoyl group;
(31) a mono- or di-5- to 7-membered heterocyclyl-carbamoyl group;
(32) a sulfamoyl group;
(33) a mono- or di-$C_{1-6}$ alkyl-sulfamoyl group;
(34) a mono- or di-$C_{6-14}$ aryl-sulfamoyl group;
(35) a $C_{1-6}$ alkyl-carbonylamino group (e.g., acetylamino, propionylamino) optionally substituted by carboxyl group(s);
(36) a heterocyclyloxy group; and the like, can be mentioned.

Unless otherwise specified, as the "optionally substituted amino group" in the present specification, an amino group optionally substituted by 1 or 2 substituents selected from
(1) an optionally substituted $C_{1-6}$ alkyl group;
(2) an optionally substituted $C_{2-6}$ alkenyl group;
(3) an optionally substituted $C_{2-6}$ alkynyl group;
(4) an optionally substituted $C_{3-8}$ cycloalkyl group;
(5) an optionally substituted $C_{6-14}$ aryl group;
(6) an optionally substituted $C_{1-6}$ alkoxy group;
(7) an optionally substituted acyl group;
(8) an optionally substituted heterocyclic group (preferably furyl, pyridyl, thienyl, pyrazolyl, thiazolyl, oxazolyl);
(9) a sulfamoyl group;
(10) a mono- or di-$C_{1-6}$ alkyl-sulfamoyl group;
(11) a mono- or di-$C_{6-14}$ aryl-sulfamoyl group; and the like, can be mentioned. When the "optionally substituted amino group" is an amino group substituted by 2 substituents, these substituents may form a nitrogen-containing heterocycle together with the adjacent nitrogen atom. As the "nitrogen-containing heterocycle", for example, a 5- to 7-membered nitrogen-containing heterocycle containing, as a ring-constituting atom besides carbon atoms, at least one nitrogen atom and optionally further containing 1 or 2 hetero atoms selected from an oxygen atom, a sulfur atom and a nitrogen atom can be mentioned. As preferable examples of the nitrogen-containing heterocycle, pyrrolidine, imidazolidine, pyrazolidine, piperidine, piperazine, morpholine, thiomorpholine, thiazolidine, oxazolidine and the like can be mentioned.

Unless otherwise specified, as the "optionally substituted acyl group" in the present specification, groups represented by the formula: —$COR^7$, —CO—$OR^7$, —$SO_2R^7$, —$SOR^7$, —$PO(OR^7)(OR^8)$, —CO—$NR^{7a}R^{8a}$ and —CS—$NR^{7a}R^{8a}$, wherein $R^7$ and $R^8$ are the same or different and each is a hydrogen atom, an optionally substituted hydrocarbon group or an optionally substituted heterocyclic group, and $R^{7a}$ and $R^{8a}$ are the same or different and each is a hydrogen atom, an optionally substituted hydrocarbon group or an optionally substituted heterocyclic group, or $R^{7a}$ and $R^{8a}$ may form an optionally substituted nitrogen-containing heterocycle together with the adjacent nitrogen atom, and the like can be mentioned.

As the "nitrogen-containing heterocycle" of the "optionally substituted nitrogen-containing heterocycle" which $R^{7a}$ and $R^{8a}$ form together with the adjacent nitrogen atom, for example, a 5- to 7-membered nitrogen-containing heterocycle containing, as a ring-constituting atom besides carbon atoms, at least one nitrogen atom and optionally further containing 1 to 2 hetero atoms selected from an oxygen atom, a sulfur atom and a nitrogen atom can be mentioned. As preferable examples of the "nitrogen-containing heterocycle", pyrrolidine, imidazolidine, pyrazolidine, piperidine, piperazine, morpholine, thiomorpholine, thiazolidine, oxazolidine and the like can be mentioned.

The nitrogen-containing heterocycle optionally has 1 to 2 substituents at substitutable positions. As these substituents, a hydroxy group, an optionally halogenated $C_{1-6}$ alkyl group, a $C_{6-14}$ aryl group, a $C_{7-16}$ aralkyl group and the like can be mentioned.

As preferable examples of the "optionally substituted acyl group",
a formyl group;
a carboxyl group;
a carbamoyl group;
a $C_{1-6}$ alkyl-carbonyl group;
a $C_{1-6}$ alkoxy-carbonyl group;
a $C_{3-8}$ cycloalkyl-carbonyl group;
a $C_{6-14}$ aryl-carbonyl group;
a $C_{7-16}$ aralkyl-carbonyl group;
a $C_{6-14}$ aryloxy-carbonyl group;
a $C_{7-16}$ aralkyloxy-carbonyl group;
a mono- or di-$C_{1-6}$ alkyl-carbamoyl group;
a mono- or di-$C_{6-14}$ aryl-carbamoyl group;
a mono- or di-$C_{3-8}$ cycloalkyl-carbamoyl group;
a mono- or di-$C_{7-16}$ aralkyl-carbamoyl group;
a $C_{1-6}$ alkylsulfonyl group;

a $C_{6-14}$ arylsulfonyl group optionally substituted by nitro group(s);
a nitrogen-containing heterocyclyl-carbonyl group;
a $C_{1-6}$ alkylsulfinyl group;
a $C_{6-14}$ arylsulfinyl group;
a thiocarbamoyl group;
a sulfamoyl group;
a mono- or di-$C_{1-6}$ alkyl-sulfamoyl group;
a mono- or di-$C_{6-14}$ aryl-sulfamoyl group;
a mono- or di-$C_{7-16}$ aralkyl-sulfamoyl group;
and the like can be mentioned.

Each symbol in the formula (I) is described in detail in the following.

$R^1$ is $R^6$—$SO_2$— (wherein $R^6$ is a substituent) or an optionally substituted 1,1-dioxidotetrahydrothiopyranyl group.

As used herein, as the "substituent" for $R^6$, an "optionally substituted hydrocarbon group", an "optionally substituted heterocyclic group", an "optionally substituted hydroxy group", an "optionally substituted amino group", an "optionally substituted mercapto group", a "cyano group", an "optionally substituted acyl group", a "halogen atom" and the like can be mentioned.

$R^6$ is preferably an optionally substituted hydrocarbon group, more preferably a $C_{1-6}$ alkyl group (preferably methyl, ethyl).

The "1,1-dioxidotetrahydrothiopyranyl group" of the "optionally substituted 1,1-dioxidotetrahydrothiopyranyl group" for $R^1$ optionally has 1 to 5 substituents, preferably 1 to 3, substituents at substitutable positions. As the "substituent", those exemplified as the substituents of the aforementioned "optionally substituted $C_{3-8}$ cycloalkyl group" can be used. When the "1,1-dioxidotetrahydrothiopyranyl group" has two or more substituents, respective substituents may be the same or different.

The "substituent" is preferably a hydroxy group and the like.

$R^1$ is preferably a $C_{1-6}$ alkylsulfonyl group (preferably methylsulfonyl, ethylsulfonyl) or a 1,1-dioxidotetrahydrothiopyranyl group, each of which is optionally substituted by 1 to 3 substituents selected from a hydroxy group and the like, more preferably a $C_{1-6}$ alkylsulfonyl group (preferably methylsulfonyl, ethylsulfonyl), or a 1,1-dioxidotetrahydrothiopyranyl group optionally substituted by hydroxy group(s).

As another embodiment, $R^1$ is preferably $R^6$—$SO_2$— (wherein $R^6$ is a substituent), more preferably a $C_{1-6}$ alkylsulfonyl group (preferably methylsulfonyl, ethylsulfonyl).

X is a bond or a divalent hydrocarbon group.

As the "divalent hydrocarbon group" for X, for example, a divalent chain hydrocarbon group, a divalent cyclic hydrocarbon group, a divalent chain-cyclic hydrocarbon group can be mentioned. Specifically,
(1) a $C_{1-10}$ alkylene group (e.g., —$CH_2$—, —$(CH_2)_2$—, —$(CH_2)_3$—, —$(CH_2)_4$—, —$(CH_2)$—, —$(CH_2)_6$—, —$CHCH_3$—, —$C(CH_3)_2$, —$(CH(CH_3))_2$—, —$(CH_2)_2C(CH_3)_2$—, —$(CH_2)_3C(CH_3)_2$—);
(2) a $C_{2-10}$ alkenylene group (e.g., —CH=CH—, —$CH_2$—CH=CH—, —CH=CH—$CH_2$—, —CH=CH—$CH_2$—$CH_2$—, —$C(CH_3)_2$—CH=CH—, —$CH_2$—CH=CH—$CH_2$—, —$CH_2$—$CH_2$—CH=CH—, —CH=CH—CH=CH—, —CH=CH—$CH_2$—$CH_2$—$CH_2$—);
(3) a $C_{2-10}$ alkynylene group (e.g., —C≡C—, —$CH_2$—C≡C—, —$CH_2$—C≡C—$CH_2$—$CH_2$—);
(4) a $C_{3-8}$ cycloalkylene group (e.g., 1,2-cyclopropylene, 1,3-cyclobutylene, 1,3-cyclopentylene, 1,3-cyclohexylene, 1,4-cyclohexylene, 1,4-cycloheptylene, 1,5-cyclooctylene);
(5) a $C_{6-14}$ arylene group (e.g., phenylene (e.g., 1,2-phenylene, 1,3-phenylene, 1,4-phenylene), naphthylene (e.g., 1,2-naphthylene, 1,3-naphthylene, 1,4-naphthylene, 1,5-naphthylene, 1,6-naphthylene, 1,7-naphthylene, 1,8-naphthylene, 2,3-naphthylene, 2,6-naphthylene, 2,7-naphthylene), biphenylene (e.g., 2,2'-biphenylene, 3,3'-biphenylene, 4,4'-biphenylene) and the like. The $C_{6-14}$ arylene may be saturated partially, and as the partially saturated $C_{6-14}$ arylene, for example, tetrahydronaphthylene and the like can be mentioned);
(6) a combination of any two selected from the above-mentioned (1) to (5) (e.g., methylene-phenylene, phenylene-methylene, ethylene-phenylene, phenylene-ethylene, methylene-cyclohexylene, cyclohexylene-methylene, methylene-naphthylene, naphthylene-methylene);
and the like can be mentioned.

X is preferably a bond or a $C_{1-10}$ alkylene group (preferably a $C_{1-6}$ alkylene group, more preferably a straight chain $C_{1-3}$ alkylene group), more preferably a $C_{1-6}$ alkylene group (preferably a straight chain $C_{1-3}$ alkylene group, more preferably —$(CH_2)_3$—).

$R^2$ and $R^3$ are the same or different and each is a hydrogen atom, a halogen atom, an optionally substituted hydrocarbon group or an optionally substituted hydroxy group.

Preferably, $R^2$ and $R^3$ are the same or different and each is a hydrogen atom;
a halogen atom; or
a $C_{1-6}$ alkyl group (preferably methyl),
and more preferably, $R^2$ and $R^3$ are each a hydrogen atom.

$R^4$ and $R^5$ are the same or different and each is a $C_{1-6}$ alkyl group optionally substituted by hydroxy group(s).

Preferably, $R^4$ and $R^5$ are the same or different and each so is a $C_{1-6}$ alkyl group, and more preferably, $R^4$ and $R^5$ are each methyl.

Ring A is a benzene ring optionally further having substituent(s) selected from a halogen atom, an optionally substituted hydrocarbon group, an optionally substituted hydroxy group and an optionally substituted amino group.

Ring A is preferably a benzene ring optionally further having 1 to 3 substituents selected from
a halogen atom;
a $C_{1-6}$ alkyl group optionally substituted by 1 to 3 $C_{6-14}$ aryloxy groups (preferably phenoxy);
a $C_{1-6}$ alkoxy group optionally substituted by 1 to 3 $C_{6-14}$ aryl groups (preferably phenyl); and
a $C_{6-14}$ aryloxy group (preferably phenoxy),
more preferably a benzene ring optionally further having 1 to 3 substituents selected from a halogen atom, a $C_{1-6}$ alkyl group and a $C_{1-6}$ alkoxy group, particularly preferably an unsubstituted benzene ring.

Ring B is a 5- to 7-membered ring.

As the "5- to 7-membered ring" for ring B, for example, 5- to 7-membered aromatic rings such as a benzene ring, a 5- to 7-membered aromatic heterocycle and the like; 5- to 7-membered non-aromatic rings such as a 5- to 7-membered alicyclic hydrocarbon, a 5- to 7-membered non-aromatic heterocycle and the like, can be mentioned.

As the 5- to 7-membered aromatic heterocycle, for example, a 5- to 7-membered monocyclic aromatic heterocycle containing, as a ring-constituting atom besides carbon atoms, 1 to 4 hetero atoms selected from an oxygen atom, a sulfur atom and a nitrogen atom can be mentioned.

As preferable examples of the monocyclic aromatic heterocycle, furan, thiophene, pyridine, pyrimidine, pyridazine, pyrazine, pyrrole, imidazole, pyrazole, isoxazole, isothiazole, oxazole, thiazole, oxadiazole, thiadiazole, triazole, tetrazole, triazine and the like can be mentioned.

As the 5- to 7-membered alicyclic hydrocarbon, a saturated or unsaturated alicyclic hydrocarbon having 5 to 7 carbon atoms, for example, a $C_{5-7}$ cycloalkane, a $C_{5-7}$ cycloalkene and the like can be mentioned.

As preferable examples of the $C_{5-7}$ cycloalkane, cyclopentane, cyclohexane, cycloheptane and the like can be mentioned.

As preferable examples of the $C_{5-7}$ cycloalkene, cyclopentene, cyclohexene, cycloheptene and the like can be mentioned.

As the 5- to 7-membered non-aromatic heterocycle, for example, a 5- to 7-membered monocyclic non-aromatic heterocycle containing, as a ring-constituting atom besides carbon atoms, 1 to 4 hetero atoms selected from an oxygen atom, a sulfur atom and a nitrogen atom can be mentioned.

As preferable examples of the monocyclic non-aromatic heterocycle, dihydrofuran, tetrahydrofuran, dihydrothiophene, tetrahydrothiophene, pyrrolidine, pyrroline, pyrazolidine, pyrazoline, piperidine, piperazine, morpholine, thiomorpholine, hexamethylenimine, oxazolidine, oxazoline, thiazolidine, thiazoline, imidazolidine, imidazoline, azepane, oxazepane, tetrahydropyridine, dihydropyridine and the like can be mentioned.

Ring B is preferably a 5- to 7-membered monocyclic non-aromatic heterocycle, more preferably tetrahydrofuran. That is, a ring represented by

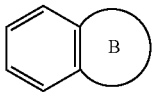

is

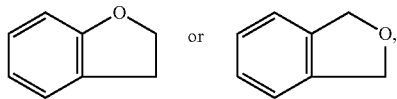 [SMILES: c1ccc2c(c1)CCO2 ; c1ccc2c(c1)COC2]

particularly preferably

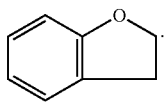

Y is a bond or $CH_2$.

Y is preferably $CH_2$.

R is an optionally substituted hydroxy group.

As used herein, the "substituent" which the "optionally substituted hydroxy group" optionally has is preferably a $C_{1-6}$ alkyl group.

R is preferably a hydroxy group; or a $C_{1-6}$ alkoxy group (preferably methoxy), more preferably a hydroxy group.

In the formula (I), the partial structure:

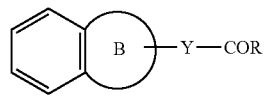

is preferably (2,3-dihydro-1-benzofuran-3-yl)acetic acid, namely

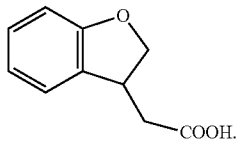 [SMILES: O=C(O)CC1COc2ccccc21]

Especially, compound (I) having a partial structure of ((3S)-2,3-dihydro-1-benzofuran-3-yl)acetic acid has an excellent GPR40 receptor agonist activity, and is preferable.

As preferable examples of compound (I), the following compounds can be mentioned.

[Compound A]

Compound (I) wherein $R^1$ is a $C_{1-6}$ alkylsulfonyl group (preferably methylsulfonyl, ethylsulfonyl) or a 1,1-dioxidotetrahydrothiopyranyl group, each of which is optionally substituted by 1 to 3 substituents selected from a hydroxy group and the like

[$R^1$ is preferably a $C_{1-6}$ alkylsulfonyl group (preferably methylsulfonyl, ethylsulfonyl), or a 1,1-dioxidotetrahydrothiopyranyl group optionally substituted by hydroxy group(s)];

X is a bond or a $C_{1-6}$ alkylene group (preferably a straight chain $C_{1-3}$ alkylene group);

$R^2$ and $R^3$ are the same or different and each is a hydrogen atom;

a halogen atom; or a $C_{1-6}$ alkyl group (preferably methyl);

$R^4$ and $R^5$ are the same or different and each is a $C_{1-6}$ alkyl group (preferably methyl);

ring A is a benzene ring optionally further having 1 to 3 substituents selected from a halogen atom, a $C_{1-6}$ alkyl group and a $C_{1-6}$ alkoxy group (preferably an unsubstituted benzene ring);

ring B is a 5- to 7-membered monocyclic non-aromatic heterocycle (preferably tetrahydrofuran);

Y is $CH_2$; and

R is a hydroxy group or a $C_{1-6}$ alkoxy group

[R is preferably a hydroxy group].

[Compound B]

Compound (I) wherein $R^1$ is a $C_{1-6}$ alkylsulfonyl group (preferably methylsulfonyl, ethylsulfonyl) or a 1,1-dioxidotetrahydrothiopyranyl group, each of which is optionally substituted by 1 to 3 substituents selected from a hydroxy group and the like

[$R^1$ is preferably a $C_{1-6}$ alkylsulfonyl group (preferably methylsulfonyl, ethylsulfonyl), or a 1,1-dioxidotetrahydrothiopyranyl group optionally substituted by hydroxy group(s)];

X is a bond or a $C_{1-6}$ alkylene group (preferably a straight chain $C_{1-3}$ alkylene group);

$R^2$ and $R^3$ are the same or different and each is a hydrogen atom;

a halogen atom; or a $C_{1-6}$ alkyl group (preferably methyl);

$R^4$ and $R^5$ are the same or different and each is a $C_{1-6}$ alkyl group (preferably methyl, ethyl) optionally substituted by hydroxy group(s)

[preferably, $R^4$ and $R^5$ are the same or different and each is a $C_{1-6}$ alkyl group (preferably methyl)];

ring A is a benzene ring optionally further having 1 to 3 substituents selected from a halogen atom;

a $C_{1-6}$ alkyl group optionally substituted by 1 to 3 $C_{6-14}$ aryloxy groups (preferably phenoxy);

a $C_{1-6}$ alkoxy group optionally substituted by 1 to 3 $C_{6-14}$ aryl groups (preferably phenyl); and a $C_{6-14}$ aryloxy group (preferably phenoxy)

[ring A is preferably a benzene ring optionally further having 1 to 3 substituents selected from a halogen atom, a $C_{1-6}$ alkyl group and a $C_{1-6}$ alkoxy group, particularly preferably an unsubstituted benzene ring];

ring B is a 5- to 7-membered monocyclic non-aromatic heterocycle (preferably tetrahydrofuran);

Y is $CH_2$; and

R is a hydroxy group or a $C_{1-6}$ alkoxy group

[R is preferably a hydroxy group].

[Compound C]

Compound (I) which is selected from

[(3S)-6-({4'-[(4-hydroxy-1,1-dioxidotetrahydro-2H-thiopyran-4-yl)methoxy]-2',6'-dimethylbiphenyl-3-yl}methoxy)-2,3-dihydro-1-benzofuran-3-yl]acetic acid (Example 6),

[(3S)-6-({2',6'-dimethyl-4'-[3-(methylsulfonyl)propoxy]biphenyl-3-yl}methoxy)-2,3-dihydro-1-benzofuran-3-yl]acetic acid (Example 10),

[(3S)-6-({3'-fluoro-2',6'-dimethyl-4'-[3-(methylsulfonyl)propoxy]biphenyl-3-yl}methoxy)-2,3-dihydro-1-benzofuran-3-yl]acetic acid (Example 13),

[(3S)-6-({3'-chloro-2',6'-dimethyl-4'-[3-(methylsulfonyl)propoxy]biphenyl-3-yl}methoxy)-2,3-dihydro-1-benzofuran-3-yl]acetic acid (Example 22),

[(3S)-6-({3',5'-dichloro-2',6'-dimethyl-4'-[3-(methylsulfonyl)propoxy]biphenyl-3-yl}methoxy)-2,3-dihydro-1-benzofuran-3-yl]acetic acid (Example 24), and

[(3S)-6-({2',6'-diethyl-4'-[3-(methylsulfonyl)propoxy]biphenyl-3-yl}methoxy)-2,3-dihydro-1-benzofuran-3-yl]acetic acid (Example 26).

As a salt of compound (I), for example, metal salts, an ammonium salt, salts with organic bases, salts with inorganic acids, salts with organic acids, salts with basic or acidic amino acids and the like can be mentioned.

Preferable examples of the metal salt include alkali metal salts such as sodium salt, potassium salt and the like; alkaline earth metal salts such as calcium salt, magnesium salt, barium salt and the like; aluminum salt and the like.

Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Preferable examples of the salt with inorganic acid include a salt with hydrochloric acid, hydrobromic acid, nitric acid, sulfuric acid, phosphoric acid and the like.

Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include a salt with arginine, lysine, ornithine and the like. Preferable examples of the salt with acidic amino acid include a salt with aspartic acid, glutamic acid and the like.

Of the above-mentioned salts, a pharmacologically acceptable salt is preferable.

The prodrug of the compound (I) is a compound which is converted to the compound (I) with a reaction due to an enzyme, gastric acid, etc. under the physiological condition in the living body, that is, a compound which is converted to the compound (I) by enzymatic oxidation, reduction, hydrolysis, etc.; a compound which is converted to the compound (I) by hydrolysis etc. due to gastric acid, and the like.

Examples of a prodrug of compound (I) include a compound wherein an amino group of compound (I) is acylated, alkylated or phosphorylated (e.g., a compound wherein an amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated); a compound wherein a hydroxy group of compound (I) is acylated, alkylated, phosphorylated or borated (e.g., a compound wherein a hydroxy group of compound (I) is acetylated, palmitoylated, propanoylated, pivaloylated, succinylated, fumarylated, alanylated or dimethylaminomethylcarbonylated); a compound wherein a carboxyl group of compound (I) is esterified or amidated (e.g., a compound wherein a carboxyl group of compound (I) is $C_{1-6}$ alkyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated) and the like. Of these, a compound wherein a carboxyl group of compound (I) is esterified by $C_{1-6}$ alkyl group such as methyl, ethyl, tert-butyl and the like is preferable. These compounds can be produced from compound (I) according to a method known per se.

A prodrug of the compound (I) may be a compound that converts to the compound (I) under physiological conditions as described in Development of Pharmaceutical Products, vol. 7, Molecule Design, 163-198, Hirokawa Shoten (1990).

Hereinafter the production methods of the compound (I) are explained.

Each symbol of the compounds in the schematic drawings of the following schemes is as defined above unless particularly described. Each compound described in the schemes may form a salt as long as it does not inhibit the reaction, and as such salt, those similar to the salts of compound (I) can be mentioned.

The compound obtained in each step can also be used as a crude product in the form of a reaction mixture in the next reaction, or can be isolated from the reaction mixture according to a conventional method, and further purified easily by a separation method such as recrystallization, distillation, chromatography and the like.

Compound (I) (e.g., compounds represented by the formulas (Ia) and (Ia') (to be abbreviated as compound (Ia) and compound (Ia') respectively)) can be produced, for example, according to the method shown in the following Scheme 1 or a method analogous thereto.

Scheme 1
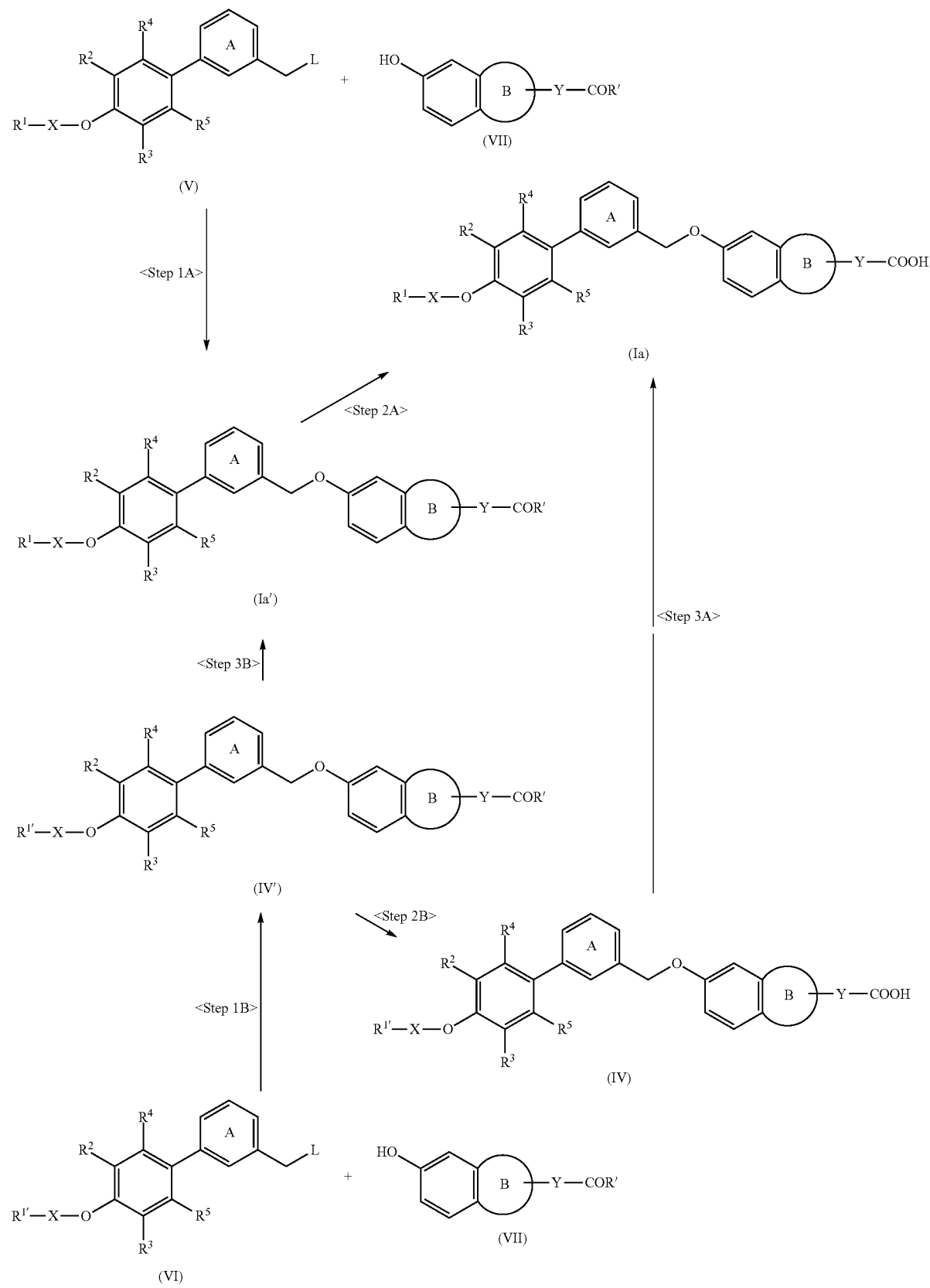

wherein $R^1$, is $R^6$—S— (wherein $R^6$ is as defined above) or a tetrahydrothiopyranyl group, $R^1$ is an optionally substituted $C_{1-6}$ alkoxy group, L is a leaving group or a hydroxy group, and the other symbols are as defined above.

<Step 1A>

(i) When L is a hydroxy group, compound (Ia') can be produced by subjecting a compound represented by the formula (V) and a compound represented by the formula (VII) (to be abbreviated as compound (V) and compound (VII) respectively) to the Mitsunobu reaction (Synthesis, 1981, pages 1-27).

In the Mitsunobu reaction, compound (V) and compound (VII) are reacted in the presence of an azodicarbonyl compound (e.g., diethyl azodicarboxylate, diisopropyl azodicarboxylate, 1,1'-(azodicarbonyl)dipiperidine) and a phosphine (e.g., triphenylphosphine, tributylphosphine).

The amount of compound (VII) to be used is generally about 0.2 to about 5 mol, preferably about 0.5 to about 2 mol, per 1 mol of compound (V).

The amount of the azodicarbonyl compound and phosphine to be used is generally about 1 to about 5 mol, preferably about 1 to about 2 mol, per 1 mol of compound (V), respectively.

The reaction is advantageously carried out using a solvent inert to the reaction. While the solvent is not particularly limited as long as the reaction proceeds, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; halogenated hydrocarbons such as dichloromethane, chloroform, carbon tetrachloride, 1,2-dichloroethane and the like; nitriles such as acetonitrile, propionitrile and the like; ketones such as acetone, ethyl methyl ketone and the like; sulfoxides such as dimethyl sulfoxide and the like; a mixed solvent thereof and the like are preferable.

The reaction temperature is generally −20 to 200° C., preferably 0 to 100° C. The reaction time is generally 5 min to 100 hr, preferably 30 min to 72 hr.

(ii) When L is a leaving group, compound (Ia') can be produced by reacting compound (V) with compound (VII) in the presence of a base.

As the leaving group for L, for example, a halogen atom, an optionally halogenated $C_{1-6}$ alkylsulfonyloxy group (e.g., methanesulfonyloxy, ethanesulfonyloxy, trichloromethanesulfonyloxy, trifluoromethanesulfonyloxy), a $C_{6-10}$ arylsulfonyloxy group optionally having substituent(s) [for example, a $C_{6-10}$ arylsulfonyloxy group (e.g., phenylsulfonyloxy, naphthylsulfonyloxy) optionally having 1 to 3 substituents selected from a $C_{1-6}$ alkyl group, a $C_{1-6}$ alkoxy group and a nitro group and the like; specifically, phenylsulfonyloxy, m-nitrophenylsulfonyloxy, p-toluenesulfonyloxy and the like], an acyloxy group (e.g., trichloroacetoxy, trifluoroacetoxy) and the like can be mentioned.

As the base, for example, alkali metal hydroxides such as lithium hydroxide, sodium hydroxide, potassium hydroxide and the like; alkaline earth metal hydroxides such as barium hydroxide and the like; alkali metal carbonates such as sodium carbonate, potassium carbonate, cesium carbonate and the like; alkali metal hydrogencarbonates such as sodium hydrogencarbonate and the like; alkali metal phosphates such as tripotassium phosphate and the like; acetates such as sodium acetate, ammonium acetate and the like; aromatic amines such as pyridine, lutidine and the like; tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like; alkali metal hydrides such as sodium hydride, potassium hydride and the like; metal amides such as sodium amide, lithium diisopropylamide, lithium hexamethyldisilazide and the like; alkali metal alkoxides having 1 to 6 carbon atoms such as sodium methoxide, sodium ethoxide, sodium tert-butoxide, potassium tert-butoxide and the like; organic lithiums such as methyllithium, n-butyllithium, sec-butyllithium, tert-butyllithium and the like, and the like can be mentioned.

The amount of compound (VII) to be used is generally about 0.2 to about 10 mol, preferably about 0.5 to about 2 mol, per 1 mol of compound (V).

The amount of the base to be used is generally about 1 to about 10 mol, preferably about 1 to about 3 mol, per 1 mol of compound (V).

The reaction is advantageously carried out using a solvent inert to the reaction. As such solvent, those exemplified in Step 1A-(i) can be mentioned.

The reaction temperature is generally −70 to 150° C., preferably −20 to 100° C. The reaction time is generally 10 min to 100 hr, preferably 20 min to 72 hr.

<Step 1B>

A compound represented by the formula (IV') (to be abbreviated as compound (IV')) can be produced by reacting a compound represented by the formula (VI) (to be abbreviated as compound (VI)) with compound (VII) according to the method shown in Step 1A or a method analogous thereto.

<Step 2A>

Compound (Ia) can be produced by subjecting compound (Ia') to a hydrolysis reaction.

The hydrolysis reaction is carried out using an acid or a base according to a conventional method.

As the acid, for example, mineral acids such as hydrochloric acid, sulfuric acid and the like; Lewis acids such as boron trichloride, boron tribromide and the like; organic acids such as trifluoroacetic acid, p-toluenesulfonic acid and the like, and the like can be mentioned. Lewis acid can be used concurrently with a thiol or a sulfide.

As the base, for example, alkali metal hydroxides such as lithium hydroxide, sodium hydroxide, potassium hydroxide and the like; alkaline earth metal hydroxides such as barium hydroxide and the like; alkali metal carbonates such as sodium carbonate, potassium carbonate and the like; alkali metal alkoxides having 1 to 6 carbon atoms such as sodium methoxide, sodium ethoxide, potassium tert-butoxide and the like; organic bases (including hydrates) such as triethylamine, imidazole, formamidine and the like, and the like can be mentioned.

The amount of the acid or base to be used is generally about 0.5 to about 10 mol, preferably about 0.5 to about 6 mol, per 1 mol of compound (Ia').

The hydrolysis reaction is carried out without solvent, or using a solvent inert to the reaction. While the solvent is not particularly limited as long as the reaction proceeds, for example, alcohols such as methanol, ethanol, propanol and the like; aromatic hydrocarbons such as benzene, toluene and the like; saturated hydrocarbons such as cyclohexane, hexane and the like; organic acids such as formic acid, acetic acid and the like; ethers such as tetrahydrofuran, 1,4-dioxane, 1,2-dimethoxyethane and the like; amides such as N,N-dimethylformamide, N,N-dimethylacetamide and the like; halogenated hydrocarbons such as dichloromethane, chloroform, carbon tetrachloride, 1,2-dichloroethane and the like; nitriles such as acetonitrile, propionitrile and the like; ketones such as acetone, ethyl methyl ketone and the like; sulfoxides such as dimethyl sulfoxide and the like; water; a mixed solvent thereof and the like are preferable.

The reaction temperature is generally −10 to 200° C., preferably 0 to 120° C. The reaction time is generally 10 min to 100 hr, preferably 10 min to 24 hr.

<Step 2B>

Compound (IV) can be produced by subjecting compound (IV') to a hydrolysis reaction.

The hydrolysis reaction is carried out according to the method shown in Step 2A or a method analogous thereto.

<Step 3A>

Compound (Ia) can be produced by subjecting compound (IV) to an oxidation reaction.

The oxidation reaction is generally carried out using an oxidant according to a conventional method. As the oxidant, for example, hydrogen peroxide, peracetic acid, m-chloroperbenzoic acid, tert-butylhydroperoxide, potassium peroxysulfate, sodium metaperiodate, sodium perborate, sodium hypochlorite, nitric acid, chromic acid, sodium dichromate, potassium permanganate, osmium(VII) oxide, ruthenium (VII) oxide, iodobenzene dichloride, iodobenzene diacetate, halogen, ozone, singlet oxygen and the like can be mentioned.

The amount of the oxidant to be used is appropriately determined according to the kind of the oxidant. It is generally about 0.25 to about 10 mol, preferably about 0.5 to about 5 mol, per 1 mol of compound (IV).

The reaction is advantageously carried out using a solvent inert to the reaction. As such solvent, those exemplified in Step 2A can be mentioned.

The reaction temperature is generally −10 to 200° C., preferably 0 to 120° C. The reaction time is generally 10 min to 100 hr, preferably 10 min to 24 hr.

<Step 3B>

Compound (Ia') can be produced by subjecting compound (IV') to an oxidation reaction.

The oxidation reaction is carried out according to the method shown in Step 3A or a method analogous thereto.

Compound (VII) used in the above-mentioned Scheme 1 can be produced, for example, according to the methods described in Journal of Medicinal Chemistry, vol. 39, pages 4928-4934, 1996; Bioorganic and Medicinal Chemistry, vol. 9, pages 1325-1335, 2001; Heterocycles, vol. 41, pages 647-650, 1995; Journal of Medicinal Chemistry, vol. 43, pages 2049-2063, 2000; Journal of Chemical Society Perkin Transactions 1, pages 2895-2900, 1996 and the like or a method analogous thereto.

Compound (V) and compound (VI) used in the above-mentioned Scheme 1 can be produced, for example, according to the method shown in the following Scheme 2 or a method analogous thereto.

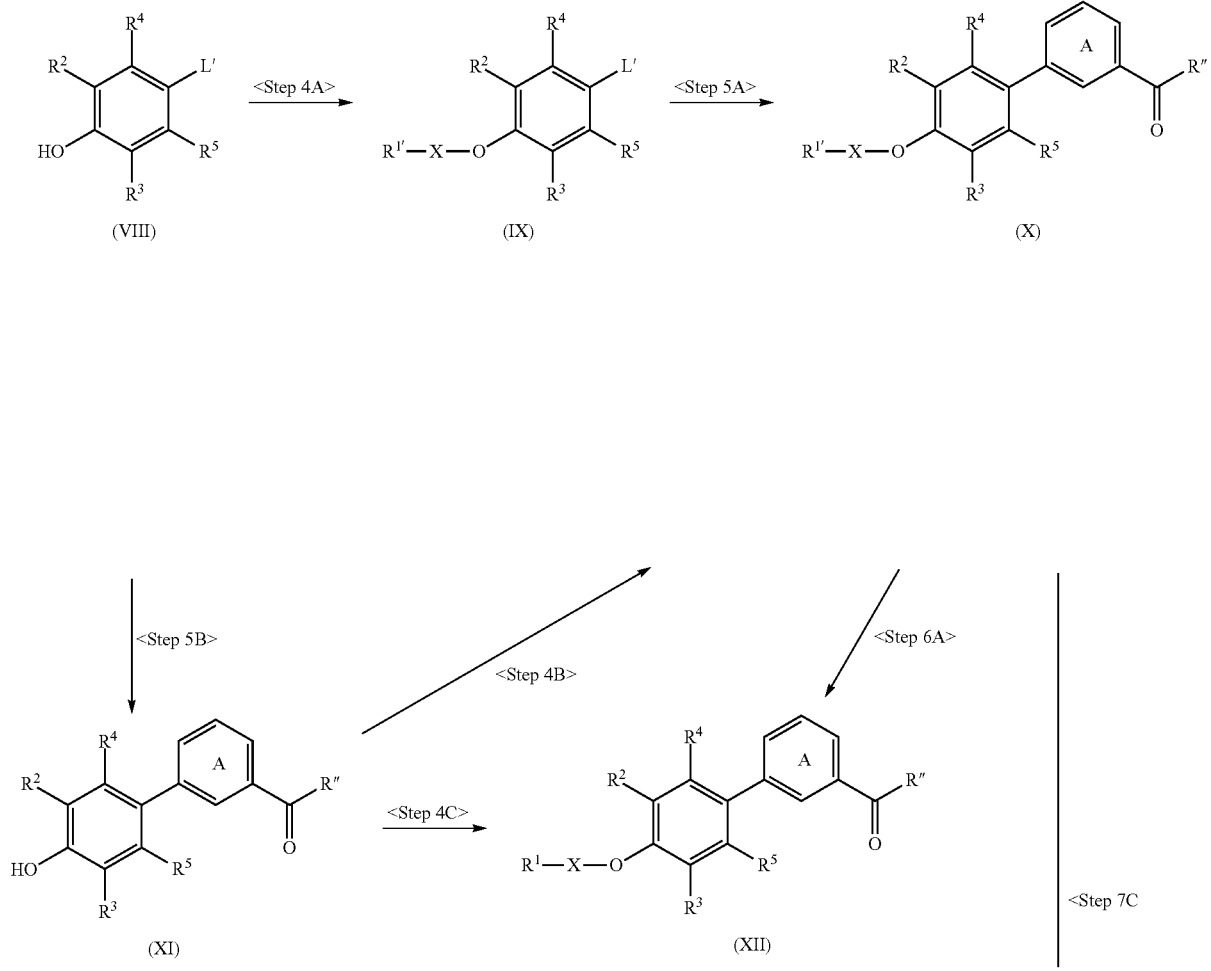

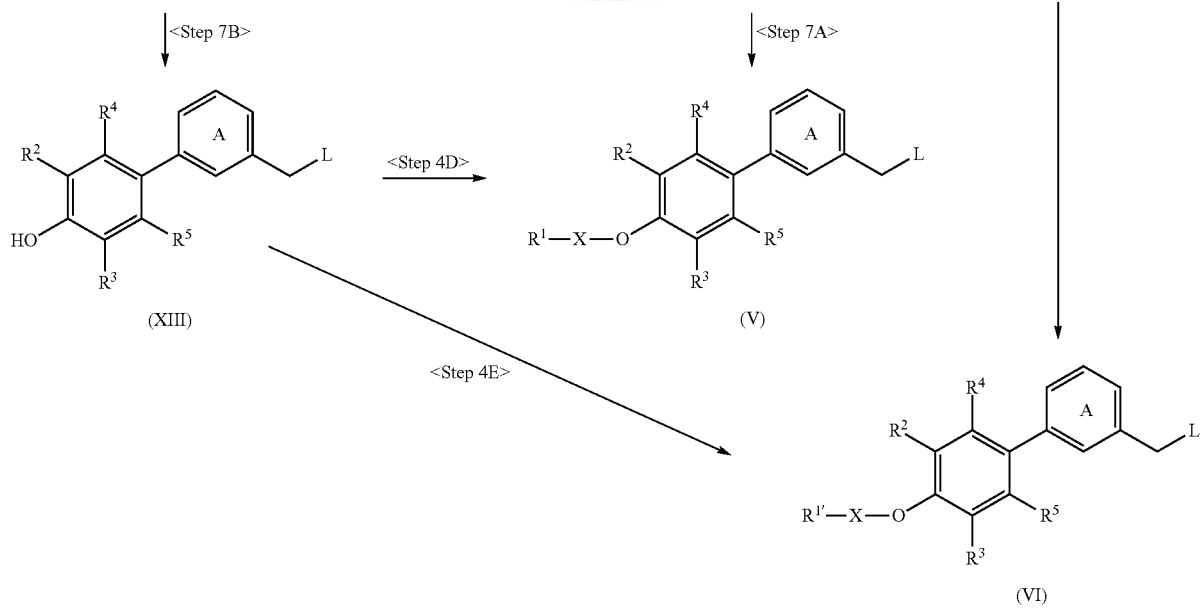

wherein R" is a hydrogen atom or an optionally substituted $C_{1-6}$ alkoxy group, L' is a leaving group, and the other symbols are as defined above.

As the "leaving group" for L', those exemplified as the aforementioned L can be mentioned.
<Step 4A>
A compound represented by the formula (IX) (to be abbreviated as compound (IX)) can be produced by reacting a compound represented by the formula (VIII) (to be abbreviated as compound (VIII)) with a compound represented by the formula: $R^{1'}$—X-L" (to be abbreviated as compound $R^{1'}$—X-L") or 1-oxa-6-thiaspiro[2.5]octane according to the method shown in the Step 1A or a method analogous thereto.

Here, L" is a leaving group or a hydroxy group, and the other symbol is as defined above. As the "leaving group" for L", those exemplified as the aforementioned L can be mentioned.
<Step 4B>
A compound represented by the formula (X) (to be abbreviated as compound (X)) can be produced by reacting a compound represented by the formula (XI) (to be abbreviated as compound (XI)) with compound $R^{1'}$—X-L" or 1-oxa-6-thiaspiro[2.5]octane according to the method shown in the Step 1A or a method analogous thereto.
<Step 4C>
A compound represented by the formula (XII) (to be abbreviated as compound (XII)) can be produced by reacting compound (XI) with a compound represented by the formula: $R^1$—X-L" (to be abbreviated as compound $R^1$—X-L") or 1-oxa-6-thiaspiro[2.5]octane 6,6-dioxide according to the method shown in the Step 1A or a method analogous thereto.
<Step 4D>
Compound (V) can be produced by reacting a compound represented by the formula (XIII) (to be abbreviated as compound (XIII)) with compound $R^1$—X-L" or 1-oxa-6-thiaspiro[2.5]octane 6,6-dioxide according to the method shown in the Step 1A or a method analogous thereto.
30<Step 4E>
Compound (VI) can be produced by reacting compound (XIII) with compound $R^{1'}$—X-L" or 1-oxa-6-thiaspiro[2.5]octane according to the method shown in the Step 1A or a method analogous thereto.

<Step 5A>
Compound (X) can be produced by subjecting compound (IX) and a compound represented by the formula: Ar-M (to be abbreviated as compound Ar-M) to a coupling reaction; or, by converting L' of compound (IX) to a metal (e.g., potassium, sodium, lithium, magnesium, copper, zinc, tin, thallium and the like, they may be complexed) according a method known per se, and subjecting the resulting compound and a compound represented by the formula: Ar-L'" (to be abbreviated as compound Ar-L'") to a coupling reaction.

Here, Ar is

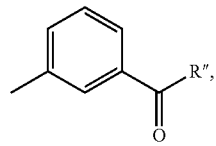

M is a metal (e.g., potassium, sodium, lithium, magnesium, copper, zinc, tin, thallium and the like, they may be complexed), L'" is a leaving group, and other symbols are as defined above. As the "leaving group" for L'", those exemplified as the aforementioned L can be mentioned.

The coupling reaction is generally carried out in the presence of a base. As the base, for example, alkali metal hydrides such as sodium hydride, potassium hydride and the like; alkali metal hydroxides such as lithium hydroxide, sodium hydroxide, potassium hydroxide and the like; alkaline earth metal hydroxides such as magnesium hydroxide, calcium hydroxide, barium hydroxide and the like; alkali metal carbonates such as sodium carbonate, potassium carbonate, cesium carbonate and the like; alkali metal hydrogencarbonates such as sodium hydrogencarbonate, potassium hydrogencarbonate and the like; alkali metal phosphates such as tripotassium phosphate and the like; alkali metal alkoxides having 1 to 6 carbon atoms such as sodium methoxide, sodium ethoxide, sodium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithiums such as methyllithium, n-butyllithium, sec-butyllithium, tert-butyllithium and the like; metal amides such as sodium amide, lithium diisopropylamide, lithium hexamethyldisilazide and the like, and the like can be mentioned.

The amount of the compound Ar-M or compound Ar-L'" to be used is generally about 0.1 to about 10 mol, preferably about 0.5 to about 2 mol, per 1 mol of compound (IX). The amount of the base to be used is generally about 1 to about 20 mol, preferably about 1 to about 5 mol, per 1 mol of compound (IX).

The coupling reaction is advantageously carried out using a solvent inert to the reaction. While the solvent is not particularly limited as long as the reaction proceeds, for example, alcohols such as methanol, ethanol, propanol, isopropanol, butanol, tert-butanol and the like; ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide; water; a mixed solvent thereof and the like are preferable.

The coupling reaction can be promoted by a metal catalyst to be used where necessary. As the metal catalyst, metal complexes having various ligands can be used and, for example, palladium compounds [e.g., palladium(II) acetate, tetrakis(triphenylphosphine)palladium(0), bis(triphenylphosphine)palladium(II) chloride, dichlorobis(triethylphosphine)palladium(II), tris(dibenzylideneacetone)dipalladium-2,2'-bis(diphenylphosphino)-1,1'-binaphthyl, a complex of palladium(II) acetate and 1,1'-bis(diphenylphosphino)ferrocene]; nickel compounds [e.g., tetrakis(triphenylphosphine)nickel(0), bis(triethylphosphine)nickel(II) chloride, bis(triphenylphosphine)nickel(II) chloride]; rhodium compounds [e.g., tris(triphenylphosphine)rhodium(III) chloride]; cobalt compounds; copper compounds [e.g., copper oxide, copper(II) chloride]; platinum compounds and the like can be mentioned. Of these, palladium compounds, nickel compounds and copper compounds are preferable.

The amount of the metal catalyst to be used is generally about 0.000001 to about 5 mol, preferably about 0.0001 to about 0.2 mol, per 1 mol of compound (IX). When a metal catalyst unstable to oxygen is used in this reaction, the reaction is preferably carried out in an inactive gas (e.g., argon gas or nitrogen gas) stream.

The reaction temperature is generally −10 to 250° C., preferably 0 to 150° C. While the reaction time varies depending on the kinds of compound (IX), compound Ar-M or compound Ar-L'", metal catalyst, base and solvent, reaction temperature and the like, it is generally 1 min to 200 hr, preferably 5 min to about 100 hr.

<Step 5B>

Compound (XI) can be produced by subjecting compound (VIII) and compound Ar-M to a coupling reaction.

The coupling reaction can be carried out according to the method shown in the Step 5A or a method analogous thereto.

<Step 6A>

Compound (XII) can be produced by subjecting compound (X) to an oxidation reaction.

The oxidation reaction can be carried out according to the method shown in the Step 3A or a method analogous thereto.

<Step 7A>

Compound (V) can be produced from compound (XII).

Compound (V) wherein L is a hydroxy group [hereinafter sometimes to be abbreviated as compound (V')] can be produced by subjecting compound (XII) to a reduction reaction.

The reduction reaction is generally carried out using a reducing agent according to a conventional method. As the reducing agent, for example, metal hydrides such as aluminum hydride, diisobutylaluminum hydride, tributyltin hydride and the like; metal hydride complexes such as sodium cyanoborohydride, sodium triacetoxyborohydride, sodium borohydride, lithium aluminum hydride and the like; borane complexes such as borane tetrahydrofuran complex, borane dimethylsulfide complex and the like; alkyl boranes such as thexylborane, disiamylborane and the like; diborane; metals such as zinc, aluminum, tin, iron and the like; alkali metals such as sodium, lithium and the like/liquid ammonia (Birch reduction) and the like can be mentioned.

The amount of the reducing agent to be used is appropriately determined according to the kind of the reducing agent. For example, the amount of the metal hydride, metal hydride complex, borane complex, alkyl borane or diborane to be used is generally about 0.25 to about 10 mol, preferably about 0.5 to about 5 mol, per 1 mol of compound (XII), and the amount of the metal (including alkali metal used for Birch reduction) to be used is generally about 1 to about 20 mol, preferably about 1 to about 5 mol, per 1 mol of compound (XII)

The reduction reaction is advantageously carried out using a solvent inert to the reaction. While the solvent is not particularly limited as long as the reaction proceeds, for example, alcohols such as methanol, ethanol, 1-propanol, 2-propanol, tert-butanol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; organic acids such as formic acid, acetic acid, propionic acid, trifluoroacetic acid, methanesulfonic acid and the like; a mixed solvent thereof and the like are preferable.

The reaction temperature is generally −20 to 100° C., preferably 0 to 80° C. While the reaction time varies depending on the reagent or solvent to be used, it is generally 10 min to 100 hr, preferably 30 min to 50 hr.

Compound (V) wherein L is a leaving group can be produced by reacting compound (V') with a halogenating agent or a sulfonylating agent.

As the halogenating agent, for example, thionyl chloride, phosphorus tribromide and the like can be used. In this case, compound (V) wherein L is a halogen atom (e.g., chlorine, bromine) can be produced.

The reaction of compound (V') with a halogenating agent, is carried out without solvent, or using a solvent inert to the reaction. As the solvent inert to the reaction, for example, halogenated hydrocarbons such as dichloromethane, chloroform, carbon tetrachloride and the like; aromatic hydrocarbons such as benzene, toluene, xylene and the like; ethers such as diethyl ether, diisopropyl ether, tert-butyl methyl ether, tetrahydrofuran, 1,4-dioxane, 1,2-dimethoxyethane and the like; esters such as methyl acetate, ethyl acetate, n-butyl acetate, tert-butyl acetate and the like, and the like can be mentioned. Alternatively, the halogenating agent may be used in an excess amount to replace a solvent.

The amount of the halogenating agent to be used is generally about 1 to about 10 mol, preferably about 1 to about 5 mol, per 1 mol of compound (V').

The reaction temperature is generally −20 to 100° C., preferably 0 to 80° C. The reaction time is generally 10 min to 100 hr, preferably 30 min to 48 hr.

As the sulfonylating agent, for example, sulfonyl halides such as methanesulfonyl chloride, benzenesulfonyl chloride, p-toluenesulfonyl chloride and the like; sulfonic acid anhydrides such as methanesulfonic anhydride, trifluoromethanesulfonic anhydride and the like, and the like can be used. In this case, compound (V) wherein L is, for example, methanesulfonyloxy, benzenesulfonyloxy, p-toluenesulfonyloxy, trifluoromethanesulfonyloxy and the like, can be produced.

The reaction of compound (V') with a sulfonylating agent is generally carried out in a solvent inert to the reaction, in the presence of a base. As the solvent inert to the reaction, those exemplified in the above-mentioned reaction of compound (V') with the halogenating agent can be mentioned.

The amount of the sulfonylating agent to be used is generally about 1 to about 10 mol, preferably about 1 to about 5 mol, per 1 mol of compound (V').

As the base, for example, amines such as triethylamine, N-methylmorpholine and the like; alkali metal hydrogencarbonates such as sodium hydrogencarbonate, potassium hydrogencarbonate and the like; alkali metal carbonates such as potassium carbonate and the like, and the like can be mentioned.

The amount of the base to be used is generally about 1 to about 10 mol, preferably about 1 to about 5 mol, per 1 mol of compound (V').

The reaction temperature is generally −20 to 100° C., preferably −10 to 80° C. The reaction time is generally 10 min to 24 hr, preferably 30 min to 8 hr.

<Step 7B>

Compound (XIII) can be produced from compound (XI) according to the method shown in the Step 7A or a method analogous thereto.

<Step 7C>

Compound (VI) can be produced from compound (X) according to the method shown in the Step 7A or a method analogous thereto.

Compound (VIII), compound R$^1$—X-L", compound R$^1$—X-L", compound Ar-M and compound Ar-L'" used in the above-mentioned Scheme 2 are commercially easily available, and can be also produced according to a method known per se or a method analogous thereto.

Of compounds (VII), an optically active form of (6-hydroxy-2,3-dihydro-1-benzofuran-3-yl)acetic acid (which is a particularly useful compound) or a salt thereof or compound (III) including the compound can be produced, for example, according to the method shown in the following Scheme 3 or a method analogous thereto.

Scheme 3

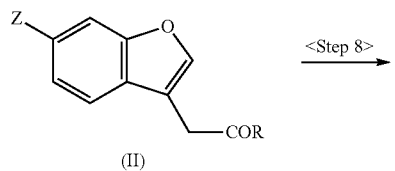
(II)
<Step 8>

-continued

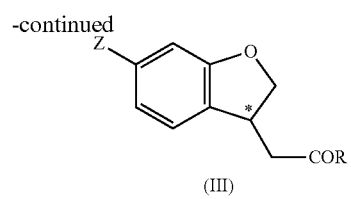
(III)

wherein a carbon atom marked with * is an asymmetric carbon atom, and the other symbols are as defined above.

<Step 8>

An optically active form of compound (III) can be produced by subjecting compound (II) to an asymmetric reduction reaction.

The asymmetric reduction reaction is advantageously carried out by hydrogenation using an optically active rhodium-phosphine complex as a catalyst, in the presence of a base.

The optically active rhodium-phosphine complex can be obtained by producing from an optically active phosphine and a rhodium complex according to a known method, and isolating or purifying according to a known means (e.g., concentration, solvent extraction, fractionation, crystallization, recrystallization, chromatography).

The optically active rhodium-phosphine complex can be also prepared by adding an optically active phosphine and a rhodium complex to a reaction system.

In this case, the timing and order of addition of the optically active phosphine and rhodium complex to the reaction system is not particularly limited, and they may be simultaneously added to the reaction system, or added separately in a staggered manner.

As the optically active phosphine, for example, 2,2'-bis-(diphenylphosphino)-1,1'-binaphthyl (hereinafter sometimes to be abbreviated as BINAP); BINAP derivatives which has substituent(s) (e.g., a C$_{1-6}$ alkyl group, a C$_{6-14}$ aryl group and the like) on the naphthyl ring of BINAP, for example, 2,2'-bis-(diphenylphosphino)-6,6'-dimethyl-1,1'-binaphthyl; BINAP derivatives wherein the naphthyl ring of BINAP is partially hydrogenated, for example, 2,2'-bis-(diphenylphosphino)-5,6,7,8,5',6',7',8'-octahydro-1,1'-binaphthyl (H8 BINAP); BINAP derivatives which has 1 to 5 substituents (e.g., a C$_{1-6}$ alkyl group and the like) on one benzene ring bonded to the phosphorus atom of BINAP, for example, 2,2'-bis-(di-p-tolylphosphino)-1,1'-binaphthyl (tol-BINAP), 2,2'-bis[bis(3,5-dimethylphenyl)phosphino]-1,1'-binaphthyl (xyl-BINAP); 2,2'-bis(dicyclohexylphosphino)-6,6'-dimethyl-1,1'-biphenyl (BICHEP), 2,3-bis(diphenylphosphino) butane (CHIRAPHOS), 1-cyclohexyl-1,2-bis(diphenylphosphino)ethane (CYCPHOS), 1,2-bis[(2-methoxyphenyl) phenylphosphino]ethane (DIPAMP), 1,2-bis (diphenylphosphino)propane (PROPHOS), 2,4-bis (diphenylphosphino)pentane (SKEWPHOS), 1-[1',2-bis (diphenylphosphino)ferrocenyl]ethylenediamine (BPPFA), 1-substituted-3,4-bis(diphenylphosphino)pyrrolidine (DEGPHOS), 2,3-O-isopropylidene-2,3-dihydroxy-1,4-bis(diphenylphosphino)butane (DIOP), substituted-1,2-bisphosphoranobenzene (DuPHOS), substituted-1,2-bisphosphoranoethane (BPE), 5,6-bis-(diphenylphosphino)-2-norbornene (NORPHOS), N,N'-bis(diphenylphosphino)-N,N'-bis(1-phenylethyl)ethylenediamine (PNNP), 2,2'-diphenylphosphino-1,1'-bicyclopentyl (BICP), 4,12-bis (diphenylphosphino)-[2,2]-paracyclophane (PhanePHOS), N-substituted-N-diphenylphosphino-1-[2-(diphenylphosphino)ferrocenyl]ethylamine (BoPhoz), 1-[2-(2-substituted-phosphino)ferrocenyl]ethyl-2-substituted-phosphine (Josiphos), 1-[2-(2'-2-substituted-phosphinophenyl)ferrocenyl]

ethyl-2-substituted-phosphine (Walphos), 2,2'-bis(α-N,N-dimethylaminophenylmethyl)-1,1'-bis(2-substituted-phosphino)ferrocene (Mandyphos), 2-substituted-phosphino-2-[α-(N,N-dimethylamino)-o-2-substituted-phosphinophenyl-methyl]ferrocene (Taniaphos), 1,1-bis(2-substituted-phosphotano)ferrocene (FerroTANE), substituted-Solphos and the like can be mentioned. Of these, DIOP, DuPHOS, BPE, BoPhoz, Josiphos, Walphos, Mandyphos, Taniaphos, FerroTANE and the like are preferable, and FerroTANE and BPE are particularly preferable.

As the rhodium complex, for example, acetylacetonatobis(cyclooctene)rhodium(I), acetylacetonatobis(ethylene)rhodium(I), acetylacetonatobis(1,5-cyclooctadiene)rhodium(I), bis(1,5-cyclooctadiene)rhodium tetrafluoroborate(I), (1,5-cyclooctadiene)rhodium trifluoromethanesulfonate(I), chlorobis(cyclooctene)rhodium(I) dimer, chlorobis(ethylene)rhodium(I) dimer, chloro(1,5-cyclooctadiene)rhodium(I) dimer, chloro(dicarbonyl)rhodium(I) dimer, chloronorbornanedienerhodium(I) dimer, chlorotris(triphenylphosphine)rhodium(I), hydroxy(1,5-cyclooctadiene)rhodium(I) dimer, dicarbonylacetylacetonatorhodium(I), dicarbonyl(pentamethylcyclopentadienyl)rhodium(III) and the like can be mentioned. Of these, bis(1,5-cyclooctadiene)rhodium tetrafluoroborate(I) and (1,5-cyclooctadiene)rhodium trifluoromethanesulfonate(I) are preferable, and (1,5-cyclooctadiene)rhodium trifluoromethanesulfonate(I) is particularly preferable.

While the amount of the optically active rhodium-phosphine complex to be used varies depending on the reaction container, reaction manner and the like, for example, it is about 0.1 to about 0.00001 mol, preferably about 0.02 to about 0.0001 mol, per 1 mol of compound (II).

As the base to be used in this reaction, for example, alkali metal hydroxides such as potassium hydroxide, sodium hydroxide, cesium hydroxide and the like; alkali metal alkoxides having 1 to 6 carbon atoms such as lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, potassium tert-butoxide and the like; alkali metal thioalkoxides having 1 to 6 carbon atoms such as sodium thiomethoxide and the like, and the like can be mentioned. Of these, an alkali metal hydroxide and an alkali metal alkoxide are preferable, and an alkali metal alkoxide having 1 to 6 carbon atoms is particularly preferable.

The amount of the base to be used is about 0.01 to about 100 mol, preferably about 0.1 to about 10 mol, per 1 mol of compound (II).

This reaction is generally carried out in a solvent. While the solvent is not particularly limited as long as it is inert to the reaction and can solubilize the starting material compound and the catalyst, for example, aromatic hydrocarbons such as toluene, xylene and the like; aliphatic hydrocarbons such as heptane, hexane and the like; halogenated hydrocarbons such as methylene chloride and the like; ethers such as diethyl ether, tetrahydrofuran and the like; alcohols such as methanol, ethanol, 2-propanol, butanol, benzyl alcohol and the like; nitriles such as acetonitrile and the like; amides such as N,N-dimethylformamide and the like; sulfoxides such as dimethyl sulfoxide and the like, and the like can be used. These solvents may be used in a mixture at an appropriate ratio. The solvent is preferably alcohol, particularly preferably methanol.

The above-mentioned solvents are preferably used for the reaction after drying and deaeration.

The amount of the solvent to be used is appropriately determined according to the solubility of compound (II) and the like. For example, when an alcohol (preferably methanol) is used as a solvent, the reaction proceeds in a condition ranging from a near solventless system to a system wherein not less than 100-fold weight of the alcohol solvent, relative to compound (II). Generally, the solvent is preferably used in about 2- to about 50-fold weight relative to compound (II).

The hydrogenation can be carried out by any of a batch reaction and a continuous reaction. In addition, the hydrogenation is carried out in the presence of hydrogen, where the hydrogen pressure is, for example, 1 to 200 atm, preferably 1 to 10 atm.

The reaction temperature is generally −30° C. to 100° C., preferably 10° C. to 80° C., more preferably 20° C. to 50° C. The reaction time is generally 0.5 to 48 hr, preferably 1 to 24 hr.

The optically active form of compound (III) obtained by the asymmetric reduction reaction can be purified by a known means (e.g., fractional recrystallization, chiral column method).

In each of the aforementioned reactions, when the starting compound has amino group, carboxyl group, hydroxy group or mercapto group as a substituent, a protecting group generally used in peptide chemistry and the like may be introduced into these groups. By removing the protecting group as necessary after the reaction, the objective compound can be obtained.

As the amino-protecting group, for example, formyl group; $C_{1-6}$ alkyl-carbonyl group (e.g., acetyl, propionyl), benzoyl group, $C_{1-6}$ alkoxy-carbonyl group (e.g., methoxycarbonyl, ethoxycarbonyl, tert-butoxycarbonyl (Boc)), allyloxycarbonyl group (Alloc), phenyloxycarbonyl group, fluorenylmethyloxycarbonyl group (Fmoc), $C_{7-10}$ aralkyloxy-carbonyl group (e.g., benzyloxycarbonyl), trityl group, phthaloyl group, dithiasuccinoyl group and N,N-dimethylaminomethylene group, each optionally having substituent(s), and the like can be used. As the substituent, for example, phenyl group, halogen atom, $C_{1-6}$ alkyl-carbonyl group (e.g., acetyl, propionyl, valeryl), optionally halogenated $C_{1-6}$ alkoxy group, nitro group and the like are used. The number of the substituent(s) is about 1 to 3.

As the carboxyl-protecting group, for example, $C_{1-6}$ alkyl group, allyl group, benzyl group, phenyl group, trityl group and trialkylsilyl group (e.g., trimethylsilyl, tert-butyldimethylsilyl, triisopropylsilyl), each optionally having substituent(s), and the like can be used. As the substituent, for example, halogen atom, formyl group, $C_{1-6}$ alkyl-carbonyl group (e.g., acetyl, propionyl, valeryl), optionally halogenated $C_{1-6}$ alkoxy group, nitro group, $C_{1-6}$ alkyl group, $C_{6-10}$ aryl group (e.g., phenyl, naphthyl) and the like are used. The number of the substituent(s) is about 1 to 3.

As the hydroxy-protecting group, for example, formyl group; $C_{1-6}$ alkyl group, $C_{7-10}$ aralkyl group, $C_{1-6}$ alkyl-carbonyl group (e.g., acetyl, propionyl), benzoyl group, phenyloxycarbonyl group, $C_{7-10}$ aralkyloxy-carbonyl group (e.g., benzyloxycarbonyl), $C_{7-10}$ aralkyl-carbonyl group (e.g., benzylcarbonyl), tetrahydropyranyl group, tetrahydrofuranyl group, furanyl group and trialkylsilyl group (e.g., trimethylsilyl, tert-butyldimethylsilyl, triisopropylsilyl), each optionally having substituent(s), and the like can be used. As the substituent, for example, halogen atom, $C_{1-6}$ alkyl group, $C_{7-10}$ aralkyl group (e.g., benzyl), $C_{6-10}$ aryl group (e.g., phenyl, naphthyl), $C_{1-6}$ alkoxy group, nitro group and the like are used. The number of the substituent(s) is about 1 to 4.

As the mercapto-protecting group, for example, $C_{1-6}$ alkyl group and $C_{7-20}$ aralkyl group (e.g., benzyl, trityl), each optionally having substituent(s), and the like can be mentioned. As the substituent, for example, halogen atom, $C_{1-6}$ alkyl group, phenyl group, C$_{7-10}$ aralkyl group (e.g., benzyl), C$_{1-6}$ alkoxy group, nitro group and the like are used. The number of the substituent(s) is about 1 to 4.

For elimination of the protecting group, a method known per se or a method analogous thereto is used. For example, treatment with acid, base, ultraviolet rays, hydrazine, phenylhydrazine, sodium N-methyldithiocarbamate, tetrabutylammonium fluoride, palladium(II) acetate and the like or reduction are used.

In each of the above-mentioned reaction steps, where desired, the compound of the present invention can be synthesized by further using hydrolysis, deprotection, acylation, alkylation, hydrogenation, oxidation, reduction, carbon chain extension and substituent exchange reaction alone or in a combination of two or more thereof. For these reactions, for example, the methods described in Shin Jikken Kagaku Koza, Vols. 14 and 15, 1977 (Maruzen Press) and the like are employed.

When the object product is obtained in a free form by the above-mentioned reactions, the product may be converted to a salt by a conventional method, and when it is obtained as a salt, the product may be converted to a free form or a different salt by a conventional method. The compound of the present invention thus obtained can be isolated and purified from a reaction mixture by a known means, such as, phase transfer, concentration, solvent extraction, fractionation, crystallization, recrystallization, chromatography and the like.

When compound (I) is present as a configurational isomer (stereoisomer), diastereomer, conformer or the like, each can be isolated by the above separation and purification methods on demand. In addition, when compound (I) is in the form of racemates, they can be separated into S- and R-forms by any conventional optical resolution.

When compound (I) includes stereoisomers, both the isomers alone and mixtures of each isomers are included in the scope of the present invention.

In addition, compound (I) may be a hydrate or non-hydrate. A hydrate of compound (I) normally shows an excellent preservation stability.

Compound (I) may be labeled with an isotope (e.g., $^3$H, $^{14}$C, $^{35}$S and the like) or the like.

Since compound (I) and a prodrug thereof (hereinafter, these are collectively abbreviated as the compound of the present invention) have a GPR40 receptor function modulating action, particularly, a GPR40 receptor agonist activity, and are low in toxicity (e.g., influence on hematological parameters such as red blood cell number, hematocrit value, hemoglobin concentration, MCH, MCHC, MCV, platelet count, leukocyte count, blood reticulocyte count, leukocyte classification and the like; blood biochemical parameters such as total protein, albumin, A/G ratio, glucose, total cholesterol, triglyceride, urea nitrogen, creatinine, total bilirubin, AST, ALT, LDH, ALP, CK, Na, K, Cl, calcium, inorganic phosphorus, retinol (vitamin A) and the like) and a fewer side effects (e.g., acute toxicity, chronic toxicity, genetic toxicity, reproductive toxicity, cardiotoxicity, drug interaction, carcinogenicity), they are useful as safe GPR40 receptor function modulators, preferably GPR40 agonists.

The compound of the present invention shows a superior GPR40 receptor function modulating action in mammals (e.g., mouse, rat, hamster, rabbit, cat, dog, bovine, sheep, monkey, human), and is useful as modulators of physiological function in which GPR40 receptor is involved or as agents for the prophylaxis or treatment of pathology or disease in which GPR40 receptor is involved.

To be specific, the compound of the present invention is useful as insulin secretion modulators (preferably insulin secretagogues), hypoglycemic agents and pancreatic P cell protectors.

Particularly, the compound of the present invention is useful as blood glucose level-dependent insulin secretagogues based on the GPR40 receptor agonist activity thereof. That is, different from sulfonylureas, the compound of the present invention is useful as insulin secretagogues that do not cause hypoglycemia.

Moreover, the compound of the present invention is useful as agents for the prophylaxis or treatment of diseases such as diabetes, impaired glucose tolerance, ketosis, acidosis, diabetic complications (e.g., diabetic neuropathy, diabetic nephropathy, diabetic retinopathy, macroangiopathy, diabetic gangrene), macular edema, hyperlipidemia, genital disorder, skin disease, arthropathy, osteopenia, arteriosclerosis, thrombotic disease, dyspepsia, memory and learning disorder, depression, depression and mania, schizophrenia, attention deficit hyperactivity disorder, visual disorder, appestat disorder (e.g., hyperorexia), obesity, hypoglycemia, hypertension, edema, insulin resistance, unstable diabetes, fatty atrophy, insulin allergy, insulinoma, lipotoxicity, hyperinsulinemia, cancers (e.g., breast cancer), metabolic syndrome, immune diseases (e.g., immunodeficiency), inflammatory disease (e.g., enteritis, arthritis, allergy), multiple sclerosis, acute kidney failure and the like. Here, diabetes includes type I diabetes, type II diabetes, gestational diabetes and obese diabetes. In addition, hyperlipidemia includes hypertriglyceridemia, hypercholesterolemia, hypo-high-density-lipoproteinemia, postprandial hyperlipidemia and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) and WHO reported new diagnostic criteria of diabetes.

According to these reports, diabetes is a condition showing a fasting blood glucose level (glucose concentration of intravenous plasma) of not less than 126 mg/dl or a 75 g oral glucose tolerance test 2 h level (glucose concentration of intravenous plasma) of not less than 200 mg/dl.

According to the above-mentioned reports of ADA and WHO, impaired glucose tolerance is a condition showing a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, the IFG (Impaired Fasting Glucose) means a condition showing a fasting blood glucose level (glucose concentration of intravenous plasma) of not less than 110 mg/dl and less than 126 mg/dl, and it is called IFG (Impaired Fasting Glycemia).

The compound of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention is also useful as a therapeutic agent for diabetes with sulfonylurea secondary failure and affords a superior insulin secretion effect and a hypoglycemic effect for diabetic patients for whom sulfonylurea compounds and fast-acting insulin secretagogues fail to provide an insulin secretion effect, and therefore, fail to provide a sufficient hypoglycemic effect.

As the sulfonylurea compound here, a compound having a sulfonylurea skeleton or a derivative thereof (e.g., tolbutamide, glibenclamide, gliclazide, chlorpropamide, tolazamide, acetohexamide, glyclopyramide, glimepiride, glipizide, glybuzole and the like) can be mentioned.

As the fast-acting insulin secretagogue, a compound that promotes insulin secretion from pancreatic β cell in the same manner as a sulfonylurea compound, though it does not have a sulfonylurea skeleton, such as glinide compounds (e.g., repaglinide, senaglinide, nateglinide, mitiglinide or a calcium salt hydrate thereof etc.), and the like, can be mentioned.

The compound of the present invention shows low toxicity, and can be safely administered orally or parenterally (e.g., topical, rectal, intravenous administration) in the form of the compound of the present invention as it is or after being admixed with a pharmacologically acceptable carrier to give a pharmaceutical preparation, according to a method known per se employed for general production methods for pharmaceutical preparations.

The dosage form of the aforementioned pharmaceutical preparation is, for example, an oral agent such as tablets (inclusive of sublingual tablets and orally disintegrable tablets), capsules (inclusive of soft capsules and micro capsules), granules, powders, troches, syrups, emulsions, suspensions and the like; or a parenteral agent such as injections (e.g., subcutaneous injections, intravenous injections, intramuscular injections, intraperitoneal injections, drip infusions), external agents (e.g., transdermal preparations, ointments), suppositories (e.g., rectal suppositories, vaginal suppositories), pellets, nasal preparations, pulmonary preparations (inhalations), ophthalmic preparations and the like.

These preparations may be controlled-release preparations (e.g., sustained-release microcapsules) such as immediate-release preparations, sustained-release preparations and the like.

The content of the compound of the present invention in a pharmaceutical preparation is about 0.01 to about 100% by weight relative to the whole preparation. While the dose varies depending on the administration subject, administration route, diseases, condition and the like, for example, the compound of the present invention (as an active ingredient) can be orally administered to a patient with diabetes (body weight about 60 kg) in about 0.01 to about 30 mg/kg body weight per day, preferably about 0.1 to about 20 mg/kg body weight per day, more preferably about 1 to about 20 mg/kg body weight per day, which may be given at once or in several portions a day.

As the above-mentioned pharmacologically acceptable carrier, various organic or inorganic carrier substances conventionally used as a preparation material can be mentioned. For example, excipient, lubricant, binder and disintegrant for solid preparations; solvent, dissolution aids, suspending agent, isotonicity agent, buffer and soothing agent for liquid preparations and the like can be mentioned. Where necessary, conventional additives such as preservatives, antioxidants, coloring agents, sweetening agents, adsorbing agents, wetting agents and the like can be used.

As the excipient, for example, lactose, sucrose, D-mannitol, starch, corn starch, crystalline cellulose, light anhydrous silicic acid and the like can be mentioned.

As the lubricant, for example, magnesium stearate, calcium stearate, talc, colloidal silica and the like can be mentioned.

As the binder, for example, crystalline cellulose, sucrose, D-mannitol, dextrin, hydroxypropylcellulose, hydroxypropylmethylcellulose, polyvinylpyrrolidone, starch, saccharose, gelatin, methylcellulose, carboxymethylcellulose sodium and the like can be mentioned.

As the disintegrant, for example, starch, carboxymethylcellulose, carboxymethylcellulose calcium, carboxymethylstarch sodium, L-hydroxypropylcellulose and the like can be mentioned.

As the solvent, for example, water for injection, alcohol, propylene glycol, macrogol, sesame oil, corn oil, olive oil and the like can be mentioned.

As the dissolution aids, for example, polyethylene glycol, propylene glycol, D-mannitol, benzyl benzoate, ethanol, trisaminomethane, cholesterol, triethanolamine, sodium carbonate, sodium citrate and the like can be mentioned.

As the suspending agent, for example, surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like, and the like can be mentioned.

As the isotonicity agent, for example, glucose, D-sorbitol, sodium chloride, glycerin, D-mannitol and the like can be mentioned.

As the buffer, for example, buffers such as phosphates, acetates, carbonates, citrates and the like, and the like can be mentioned.

As the soothing agent, for example, benzyl alcohol and the like can be mentioned.

As the preservative, for example, p-hydroxybenzoates, chlorobutanol, benzyl alcohol, phenethyl alcohol, dehydroacetic acid, sorbic acid and the like can be mentioned.

As the antioxidant, for example, sulfites, ascorbic acid, α-tocopherol and the like can be mentioned.

As the coloring agent, for example, water-soluble edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment and the like), natural pigments (e.g., β-carotene, chlorophil, red iron oxide etc.) and the like can be mentioned.

As the sweetening agent, for example, saccharin sodium, dipotassium glycyrrhizinate, aspartame, stevia and the like can be mentioned.

Moreover, the compound of the present invention can be used in combination with drugs other than the compound of the present invention.

As the drugs that can be used in combination with the compound of the present invention (hereinafter sometimes to be abbreviated as a concomitant drug), for example, other therapeutic agents for diabetes, therapeutic agents for diabetic complications, therapeutic agents for hyperlipidemia, antihypertensive agents, antiobesity agents, diuretics, chemotherapeutic agents, immunotherapeutic agents, antiinflammatory agents, antithrombotic agents, therapeutic agents for osteoporosis, vitamins, antidementia agents, therapeutic agents for pollakiuria or urinary incontinence, therapeutic agents for dysuria and the like can be mentioned. Specifically, the following agents can be mentioned.

Examples of the other therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), PPAR function modulators (e.g., pioglitazone or a salt thereof (preferably hydrochloride), rosiglitazone or a salt thereof (preferably maleate), Reglixane, Netoglitazone, FK-614, Rivoglitazone, compounds described in WO01/38325, Tesaglitazar, Ragaglitazar, Muraglitazar, ONO-5816, Edaglitazone, LM-4156, Metaglidasen (MBX-102), Naveglitazar, MX-6054, LY-510929, Balaglitazone, T-131 or a salt thereof, THR-0921), α-glucosidase inhibitors (e.g., voglibose, acarbose, miglitol, emiglitate), biguanides (e.g., phenformin, metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride), repaglinide, senaglinide, mitiglinide or calcium salt hydrate thereof, nateglinide], GLP-1 receptor agonists [e.g., GLP-1, GLP-1 MR agent, N,N-2211, AC-2993 (exendin-4), BIM-51077, Aib(8,35)hGLP-1(7,37)NH$_2$, CJC-1131], dipeptidyl peptidase IV inhibitors (e.g., NVP-DPP-278, PT-100, P32/98, P93/01, NVP-DPP-728, Vildagliptin, Saxagliptin, T-6666, sitagliptin, TS-021, alogliptin or a salt thereof (preferably benzoate), 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof (preferably succinate), 2-[2-(3-(R)-amino-piperidin-1-yl)-5-fluoro-6-oxo-6H-pyrimidin-1-ylmethyl]-benzonitrile or a salt thereof (preferably tartarate)), β3 agonists (e.g., AJ-9677), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), 11β-hydroxysteroid dehydrogenase inhibitors (e.g., BVT-3498), adiponectin or agonists thereof, IKK inhibitors (e.g., AS-2868), leptin resistance improving drugs, somatostatin receptor agonists (compounds described in WO01/25228, WO03/42204, WO98/44921, WO98/45285, WO99/22735), glucokinase activators (e.g., RO-4389620, PSN-010), GIP (glucose-dependent insulinotropic peptide), PACAP (pituitary adenylate cyclase activating polypeptide), GPR119 agonist (e.g., PSN119-1) and the like.

Examples of the therapeutic agents for diabetic complications include aldose reductase inhibitors (e.g., Tolrestat, Epalrestat, Zenarestat, Zopolrestat, Fidarestat, Minalrestat, ranirestat, CT-112), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole)), protein kinase C (PKC) inhibitors (e.g., ruboxistaurin mesylate), AGE inhibitors (e.g., ALT-945, pimagedine, pyratoxanthine, N-phenacylthiazolium bromide (ALT-766), EXO-226, ALT-711, Pyridorin, Pyridoxamine), active oxygen scavengers (e.g., thioctic acid), cerebral vasodilators (e.g., tiapuride), somatostatin receptor agonists (e.g., BIM23190), apoptosis signal regulating kinase-1 (ASK-1) inhibitors and the like.

Examples of the therapeutic agents for hyperlipidemia include HMG-CoA reductase inhibitors (e.g., pravastatin, simvastatin, lovastatin, atorvastatin, fluvastatin, pitavastatin, rosuvastatin or a salt thereof (e.g., sodium salt, calcium salt)), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), antioxidants (e.g., lipoic acid, probucol), ACAT inhibitors (e.g., Avasimibe, Eflucimibe, Pactimibe), anion exchange resins (e.g., colestyramine), probucol, nicotinic acid drugs (e.g., nicomol, niceritrol), ethyl icosapentate, plant sterols (e.g., soysterol, γ-oryzanol) and the like.

Examples of the antihypertensive agents include angiotensin converting enzyme inhibitors (e.g., captopril, enalapril, delapril), angiotensin II antagonists (e.g., losartan, candesartan cilexetil, eprosartan, valsartan, telmisartan, irbesartan, olmesartan medoxomil, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium channel blockers (e.g., manidipine, nifedipine, amlodipine, efonidipine, nicardipine), potassium channel openers (e.g., levcromakalim, L-27152, AL0671, NIP-121), clonidine and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonists; 11β-hydroxysteroid dehydrogenase inhibitors (e.g., BVT-3498)), pancreatic lipase inhibitors (e.g., orlistat, cetilistat (ATL-962)), β3 agonists (e.g., AJ-9677), peptide anorexiants (e.g., leptin, CNTF (Ciliary Neurotropic Factor)), cholecystokinin agonists (e.g., lintitript, FPL-15849), feeding deterrent (e.g., P-57), ACC2 inhibitors (e.g., CP-640186) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil), antitumor antibiotics (e.g., mitomycin, adriamycin), plant-derived antitumor agents (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivatives, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like. Of these, interleukins such as IL-1, IL-2, IL-12 and the like are preferable.

Examples of the antiinflammatory agents include non-steroidal antiinflammatory agents such as aspirin, acetaminophen, indomethacin and the like.

Examples of the antithrombotic agents include heparins (e.g., heparin sodium, heparin calcium, dalteparin sodium), warfarins (e.g., warfarin potassium), anti-thrombin drugs (e.g., argatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, pamidronate disodium, alendronate sodium hydrate, incadronate disodium, risedronate disodium and the like.

Examples of the vitamins include vitamin $B_1$, vitamin $B_{12}$ and the like.

Examples of the antidementia agents include tacrine, donepezil, rivastigmine, galanthamine and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, antibodies to a cachexia-inducing factors such as TNF-α, LIF, IL-6, oncostatin M and the like, and the like can be used in combination with the compound of the present invention.

Furthermore, glycosylation inhibitors (e.g., ALT-711), nerve regeneration promoting drugs (e.g., Y-128, VX853, prosaptide), antidepressants (e.g., desipramine, amitriptyline, imipramine), antiepileptics (e.g., lamotrigine, Trileptal, Keppra, Zonegran, Pregabalin, Harkoseride, carbamazepine), antiarrhythmic agents (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin, gabapentin MR agent), $\alpha_2$ receptor agonists (e.g., clonidine), local analgesics (e.g., capsaicin), antianxiety drugs (e.g., benzothiazepines), phosphodiesterase inhibitors (e.g., sildenafil), dopamine receptor agonists (e.g., apomorphine), midazolam, Ketoconazole and the like can be also used in combination with the compound of the present invention.

The combination drug is preferably an insulin preparation, a PPAR function modulator (preferably pioglitazone or hydrochloride thereof), an α-glucosidase inhibitor (preferably voglibose), a biguanide (preferably metformin or hydrochloride thereof), a sulfonylurea (preferably glibenclamide, glimepiride), mitiglinide or calcium salt hydrate thereof, nateglinide, a dipeptidyl peptidase IV inhibitor (preferably alogliptin or benzoate thereof, 2-[[6-[(3R)-3-amino-1-piperidinyl]-3,4-dihydro-3-methyl-2,4-dioxo-1(2H)-pyrimidinyl]methyl]-4-fluorobenzonitrile or succinate thereof, 2-[2-(3-(R)-amino-piperidin-1-yl)-5-fluoro-6-oxo-6H-pyrimidin-1-ylmethyl]-benzonitrile or tartarate thereof) and the like.

By combining the compound of the present invention with a concomitant drug, superior effects such as (1) decreased dose of the compound of the present invention or a concomitant drug as compared to single administration of the compound of the present invention or a concomitant drug, (2) possible setting of a long treatment period by selecting a concomitant drug having different action and mechanism from those of the compound of the present invention, (3) possible designing of a sustained treatment effect by selecting a concomitant drug having different action and mechanism from those of the compound of the present invention, (4) a synergistic effect afforded by a combined use of the compound of the present invention and a concomitant drug, and the like can be achieved.

When the compound of the present invention and a concomitant drug are used in combination, the administration time of the compound of the present invention and the concomitant drug is not restricted, and the compound of the present invention and the concomitant drug may be administered simultaneously, or may be administered at staggered times, to an administration subject. The dosage of the concomitant drug may be determined according to the dose clinically used, and can be appropriately selected depending on an administration subject, administration route, disease, combination and the like.

As the administration mode of the compound of the present invention and the concomitant drug, the following methods can be mentioned: (1) The compound of the present invention and the concomitant drug are simultaneously formulated to give a single preparation which is administered. (2) The compound of the present invention and the concomitant drug are separately formulated to give two kinds of preparations which are administered simultaneously by the same administration route. (3) The compound of the present invention and the concomitant drug are separately formulated to give two kinds of preparations which are administered by the same administration route at staggered times. (4) The compound of the present invention and the concomitant drug are separately formulated to give two kinds of preparations which are administered simultaneously by the different administration routes. (5) The compound of the present invention and the concomitant drug are separately formulated to give two kinds of preparations which are administered by the different administration routes at staggered times (for example, the compound of the present invention and the concomitant drug are administered in this order, or in the reverse order), and the like.

The present invention also relates to (6-hydroxy-2,3-dihydro-1-benzofuran-3-yl)acetic acid, which is a useful compound as a starting material for producing the compound of the present invention, or a salt thereof.

The compound can be produced, for example, according to the method described in below-mentioned Example 17. The compound may be a racemate or an optically active form. As a salt of the compound, those similar to the salt of compound (I) can be mentioned, with preference given to a metal salt.

Moreover, the present invention provides a production method of an optically active form of a compound represented by the formula (III):

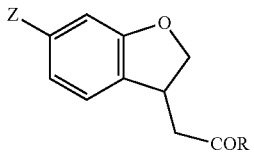

(III)

wherein
Z is a halogen atom or an optionally substituted hydroxy group; and
R is an optionally substituted hydroxy group,
or a salt thereof, which comprises subjecting a compound represented by the formula (II):

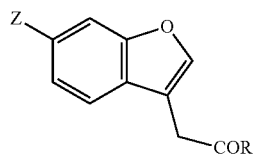

(II)

wherein each symbol is as defined above,
or a salt thereof to an asymmetric reduction reaction.

Here, Z is preferably a hydroxy group or a $C_{1-6}$ alkoxy group, more preferably a hydroxy group.

R is preferably a hydroxy group or a $C_{1-6}$ alkoxy group, more preferably a hydroxy group.

As salts of compound (II) and compound (III), those similar to the salt of compound (I) can be mentioned, with preference given to a metal salt, respectively.

EXAMPLES

The present invention is further explained in detail by referring to the following Reference Examples, Examples, Formulation Examples and Experimental Example, which are mere working examples not to be construed as limitative and may be changed without departing from the scope of the present invention.

The term "room temperature" in the following Reference Examples and Examples indicates the range of generally from about 10° C. to about 35° C. The chemical yield is an isolation yield (mol/mol %) or was obtained by high performance liquid chromatography. The optical purity (asymmetric yield) of optically active forms was evaluated according to enantiomeric excess (% e.e.). The enantiomeric excess was determined by the following formula:

enantiomeric excess (% e.e.)=100×[(R)−(S)]/[(R)+(S)]
or 100×[(S)−(R)]/[(R)+(S)]

wherein (R) and (S) are each an area of each enantiomer in high performance liquid chromatography.

The solvent used for chromatography is in % by volume and other "%" is in % by weight.

OH proton, NH proton etc. that could not be confirmed due to broad peak by proton NMR spectrum are not included in the data.

The other symbols used herein mean the following:
s: singlet
d: doublet
t: triplet
q: quartet
m: multiplet
br: broad
J: coupling constant
Hz: Hertz
$CDCl_3$: deuterated chloroform
DMSO-$d_6$: deuterated dimethyl sulfoxide
$^1$H NMR: proton nuclear magnetic resonance
(R,R)-Me-BPE: (+)-1,2-bis((2R,5R)-2,5-dimethylphosphorano)ethane
(S,S)-Et-FerroTANE: (−)-1,1'-bis((2S,4S)-2,4-diethyl phosphotano)ferrocene In the following Reference Examples and Examples, melting point, mass spectrum (MS) and nuclear magnetic resonance spectrum (NMR) were measured under the following conditions.
melting point measurement tools: Yanagimoto micromelting point measuring apparatus, or Büchi melting point measuring apparatus type B-545 was used.
MS measurement tools: Waters Corporation ZMD, Waters Corporation ZQ2000 or Micromass Ltd., platform II
Ionization method: Electron Spray Ionization (ESI) or Atmospheric Pressure Chemical Ionization (APCI). Unless specifically indicated, ESI was used.
NMR measurement tools: Varian Inc. Varian Gemini 200 (200 MHz), Varian Gemini 300 (300 MHz), Bruker BioSpin Corp. AVANCE 300, JEOL JNM-AL400.

In Reference Examples and Examples, purification by preparative HPLC was performed under the following conditions.
Preparative HPLC tools: Gilson, Inc., high through-put purification system
column: YMC Combiprep ODS-A S-5 μm, 20×50 mm solvent:
Solution A; 0.1% trifluoroacetic acid-containing water,
Solution B; 0.1% trifluoroacetic acid-containing acetonitrile
gradient cycle A: 0.00 min (Solution A/Solution B=90/10), 1.20 min (Solution A/Solution B=90/10), 4.75 min (Solution A/Solution B=0/100), 7.30 min (Solution A/Solution B=0/100), 7.40 min (Solution A/Solution B=90/10), 7.50 min (Solution A/Solution B=90/10).
gradient cycle B: 0.00 min (Solution A/Solution B=95/5), 1.00 min (Solution A/Solution B=95/5), 5.20 min (Solution A/Solution B=5/95), 6.40 min (Solution A/Solution B=5/95), 6.50 min (Solution A/Solution B=95/5), 6.60 min (Solution A/Solution B=95/5).
flow rate: 25 ml/min, detection method: UV 220 nm In the Examples, the numerical value in the parentheses in the "retention time" of the conditions of high performance liquid chromatography shows the ratio of each optical isomer produced in a mixture of the optical isomers.

Reference Example 1

4-(4-bromo-3,5-dimethylphenoxy)tetrahydro-2H-thiopyran

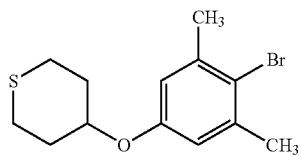 [SMILES: Cc1cc(OC2CCSCC2)cc(C)c1Br]

To a solution of 4-bromo-3,5-dimethylphenol (0.201 g, 1.00 mmol), tetrahydro-2H-thiopyran-4-ol (0.130 g, 1.10 mmol) and triphenylphosphine (0.341 g, 1.30 mmol) in tetrahydrofuran (5 mL) was added diethyl azodicarboxylate (40% solution in toluene, 0.591 mL, 1.30 mmol), and the mixture was stirred at room temperature for 1.5 hr. Tetrahydro-2H-thiopyran-4-ol (0.0591 g, 0.500 mmol), triphenylphosphine (0.157 g, 0.600 mmol) and diethyl azodicarboxylate (40% solution in toluene, 0.272 mL, 0.600 mmol) were added, and the mixture was further stirred for 1.5 hr. The reaction mixture was concentrated under reduced pressure, and the residue was purified by silica gel column chromatography (ethyl acetate:hexane=0:100-20:80) to give the title compound (0.261 g, yield 86%) as colorless crystals.

$^1$H NMR (CDCl$_3$) δ: 1.93-2.07 (2H, m), 2.10-2.23 (2H, m), 2.37 (6H, s), 2.49-2.61 (2H, m), 2.85-2.98 (2H, m), 4.26-4.35 (1H, m), 6.65 (2H, s).

Reference Example 2

[2,6-dimethyl-4-(tetrahydro-2H-thiopyran-4-yloxy)phenyl]boronic acid

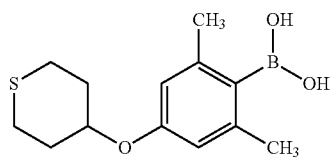 [SMILES: Cc1cc(OC2CCSCC2)cc(C)c1B(O)O]

To a solution of 4-(4-bromo-3,5-dimethylphenoxy)tetrahydro-2H-thiopyran (3.01 g, 10.0 mmol) in tetrahydrofuran (50 mL) was added dropwise n-butyllithium hexane solution (1.6 M, 6.57 mL, 10.5 mmol) at −78° C., and the reaction mixture was stirred for 1.5 hr at the same temperature. Triisopropyl borate (6.92 mL, 30.0 mmol) was added, and the mixture was stirred overnight, during which the mixture was allowed to warm to room temperature. The reaction mixture was ice-cooled, 2 M hydrochloric acid (50 mL) was added, and the mixture was stirred for 2.5 hr. The aqueous layer and the organic layer were separated, and the organic layer was washed with saturated brine and saturated aqueous sodium hydrogencarbonate while simultaneously adjusting to neutral. The organic layer was dried over anhydrous magnesium sulfate, and concentrated under reduced pressure. The residue was washed with cool hexane to give the title compound (1.89 g, yield 71%) as colorless crystals.

$^1$H NMR (CDCl$_3$) δ: 1.90-2.06 (2H, m), 2.09-2.23 (2H, m), 2.35 (6H, s), 2.48-2.62 (2H, m), 2.83-2.98 (2H, m), 4.28-4.40 (1H, m), 6.51 (2H, s), 6.59 (2H, s).

Reference Example 3 methyl 2',6'-dimethyl-4'-(tetrahydro-2H-thiopyran-4-yloxy)biphenyl-3-carboxylate

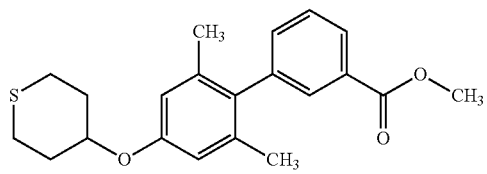 [SMILES: COC(=O)c1cccc(-c2c(C)cc(OC3CCSCC3)cc2C)c1]

In the same manner as in Reference Example 6, the title compound was obtained as colorless crystals from [2,6-dimethyl-4-(tetrahydro-2H-thiopyran-4-yloxy)phenyl]boronic acid and methyl 3-bromobenzoate.

yield 86%.

melting point 69-71C.

Reference Example 4 methyl 4'-[(1,1-dioxidotetrahydro-2H-thiopyran-4-yl)oxy]-2',6'-dimethylbiphenyl-3-carboxylate

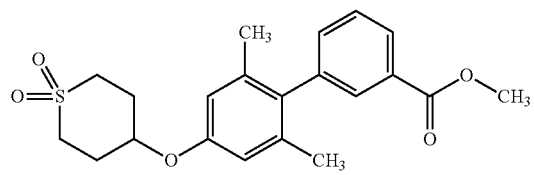 [SMILES: COC(=O)c1cccc(-c2c(C)cc(OC3CCS(=O)(=O)CC3)cc2C)c1]

To a solution of methyl 2',6'-dimethyl-4'-(tetrahydro-2H-thiopyran-4-yloxy)biphenyl-3-carboxylate (1.56 g, 4.38 mmol) in ethyl acetate (20 mL) was added m-chloroperbenzoic acid (65%, 2.44 g, 9.20 mmol) under ice-cooling, and the mixture was stirred for 16 hr, during which the mixture was allowed to gradually warm to room temperature. Ethyl acetate was added to the reaction mixture. The mixture was washed with a mixture of saturated aqueous sodium hydrogencarbonate and aqueous sodium thiosulfate solution, then washed with saturated brine, dried over anhydrous magnesium sulfate, and concentrated under reduced pressure. The residue was recrystallized from ethyl acetate-hexane to give the title compound (1.45 g, yield 85%) as colorless crystals.

melting point 180° C.

Reference Example 5

{4'-[(1,1-dioxidotetrahydro-2H-thiopyran-4-yl)oxy]-2',6'-dimethylbiphenyl-3-yl}methanol

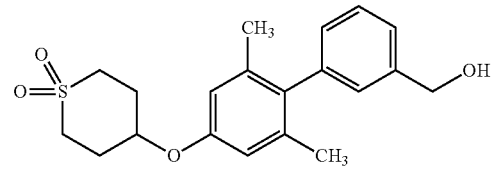 [SMILES: Cc1cc(OC2CCS(=O)(=O)CC2)cc(C)c1-c1cccc(CO)c1]

To a solution of methyl 4'-[(1,1-dioxidotetrahydro-2H-thiopyran-4-yl)oxy]-2',6'-dimethylbiphenyl-3-carboxylate (0.128 g, 0.33 mmol) in tetrahydrofuran (2 mL) was added lithium aluminum hydride (80%, 15.7 mg, 0.33 mmol) by small portions under ice-cooling, and the mixture was stirred at the same temperature for 1.5 hr. Sodium sulfate 10 hydrate (0.106 g, 0.33 mmol) was added by small portions to the reaction mixture, and the mixture was stirred at room temperature for 1 hr. The insoluble substance was filtered off through celite, and the filtrate was concentrated under reduced pressure to give the title compound (0.111 g, yield 93%) as a colorless amorphous powder.

$^1$H NMR (CDCl$_3$) δ: 1.76 (1H, t, J=5.6 Hz), 2.00 (6H, s), 2.29-2.44 (2H, m), 2.44-2.58 (2H, m), 2.87-3.02 (2H, m), 3.37-3.53 (2H, m), 4.63-4.70 (1H, m), 4.74 (2H, d, J=5.6 Hz), 6.68 (2H, s), 7.05 (1H, dt, J=7.4, 1.5 Hz), 7.12 (1H, s), 7.31-7.38 (1H, m), 7.42 (1H, t, J=7.4 Hz).

Reference Example 6

4'-hydroxy-2',6'-dimethylbiphenyl-3-carbaldehyde

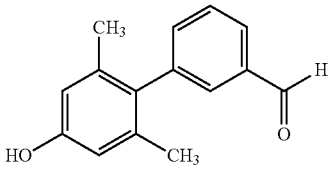

4-Bromo-3,5-dimethylphenol (10.3 g, 51.0 mmol) and (3-formylphenyl)boronic acid (7.67 g, 51.2 mmol) were dissolved in a mixture of 1 M aqueous sodium carbonate solution (150 mL), ethanol (50 mL) and toluene (150 mL). After argon substitution, tetrakis(triphenylphosphine)palladium(0) (2.95 g, 2.55 mmol) was added, and the reaction mixture was stirred at 80° C. for 24 hr under argon atmosphere. The reaction mixture was allowed to cool, and water was added. The mixture was diluted with ethyl acetate, and the insoluble substance was filtered off through celite. The organic layer of the filtrate was washed with saturated brine, dried over anhydrous magnesium sulfate, and concentrated under reduced pressure. The residue was purified by silica gel column chromatography (ethyl acetate:hexane=10:90-40:60) to give the title compound (9.53 g, yield 83%) as pale-yellow crystals.

MS m/z 227 (M+H)$^+$.

Reference Example 7

1-oxa-6-thiaspiro[2.5]octane

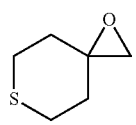

To a suspension of trimethylsulfoxonium iodide (37.1 g, 165.1 mmol) in dimethylsulfoxide (120 mL) was slowly added sodium hydride (60% in oil, 6.10 g, 152.4 mmol) at room temperature, and the mixture was stirred for 1 hr under nitrogen atmosphere. A solution of tetrahydro-4H-thiopyran-4-one (14.8 g, 127.0 mmol) in dimethylsulfoxide (60 mL) was added dropwise over 20 min to the reaction mixture, and the reaction solution was stirred at room temperature for 14 hr. The mixture was diluted with water and extracted with diethyl ether. The organic layer was washed successively with water and saturated brine, dried over anhydrous sodium sulfate, and concentrated under reduced pressure. The residue was left standing at room temperature, and the precipitated crystals were washed with a small amount of hexane and dried to give the title compound (8.22 g, yield 50%) as colorless needles.

$^1$H NMR (CDCl$_3$) δ: 1.69-1.82 (2H, m), 1.93-2.09 (2H, m), 2.56-2.73 (4H, m), 2.85-3.01 (2H, m).

Reference Example 8

4'-[(4-hydroxytetrahydro-2H-thiopyran-4-yl)methoxy]-2',6'-dimethylbiphenyl-3-carbaldehyde

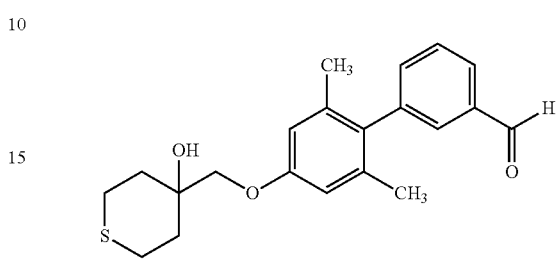

To a solution of 1-oxa-6-thiaspiro[2.5]octane (6.33 g, 48.6 mmol) and 4'-hydroxy-2',6'-dimethylbiphenyl-3-carbaldehyde (10.0 g, 44.2 mmol) in N,N-dimethylformamide (150 mL) was added potassium carbonate (6.11 g, 44.2 mmol) at room temperature, and the mixture was stirred at 100° C. for 12 hr. The reaction mixture was concentrated under reduced pressure, the residue was neutralized with 1 M hydrochloric acid, and the mixture was extracted with ethyl acetate. The extract was dried over anhydrous sodium sulfate, and concentrated under reduced pressure. The residue was crystallized from diisopropyl ether to give the title compound (12.3 g, yield 78%) as colorless crystals.

$^1$H NMR (CDCl$_3$) δ: 1.77-1.91 (2H, m), 2.00 (6H, s), 2.06-2.16 (2H, m), 2.19 (1H, s), 2.42-2.53 (2H, m), 3.04-3.18 (2H, m), 3.81 (2H, s), 6.69 (2H, s), 7.41 (1H, dt, J=7.5, 1.5 Hz), 7.59 (1H, t, J=7.5 Hz), 7.66 (1H, t, J=1.5 Hz), 7.87 (1H, dt, J=7.5, 1.5 Hz), 10.05 (1H, s).

Reference Example 9

4-({[3'-(hydroxymethyl)-2,6-dimethylbiphenyl-4-yl]oxy}methyl)tetrahydro-2H-thiopyran-4-ol

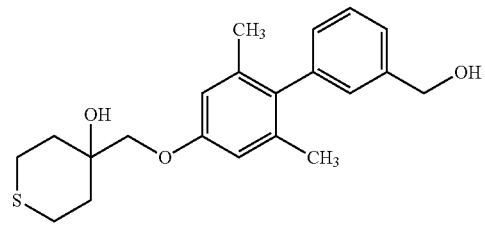 [SMILES: Cc1cc(OCC2(O)CCSCC2)cc(C)c1-c1cccc(CO)c1]

To a solution of 4'-[(4-hydroxytetrahydro-2H-thiopyran-4-yl)methoxy]-2',6'-dimethylbiphenyl-3-carbaldehyde (2.12 g, 5.95 mmol) in a mixed solvent of tetrahydrofuran (8 mL) and methanol (4 mL) was added sodium borohydride (0.225 g, 5.95 mmol) under ice-cooling, and the mixture was stirred at the same temperature for 20 min. The reaction solution was concentrated under reduced pressure, aqueous ammonium chloride solution was added to the residue, and the mixture was extracted with ethyl acetate. The extract was washed with saturated brine, dried over anhydrous sodium sulfate, and concentrated under reduced pressure to give the title compound (1.87 g, yield 88%) as colorless crystals.

$^1$H NMR (CDCl$_3$) δ: 1.70 (1H, t, J=5.8 Hz), 1.76-1.90 (2H, m), 2.01 (6H, s), 2.05-2.16 (2H, m), 2.20 (1H, s), 2.40-2.53 (2H, m), 3.03-3.18 (2H, m), 3.80 (2H, s), 4.73 (2H, d, J=5.8 Hz), 6.67 (2H, s), 7.02-7.09 (1H, m), 7.12 (1H, s), 7.31-7.37 (1H, m), 7.41 (1H, t, J=7.4 Hz).

Reference Example 10

2-hydroxy-3,4,6-trimethylbenzaldehyde

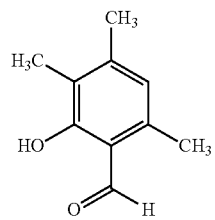

A solution of 2,3,5-trimethylphenol (13.6 g, 100 mmol,) in dichloromethane (20 mL) was ice-cooled, titanium tetrachloride (41.7 g, 220 mmol) was added dropwise over 0.5 hr under nitrogen atmosphere, and the reaction mixture was stirred for 1 hr. Dichloromethyl methyl ether (11.5 g, 100 mmol) was added dropwise, and the mixture was further stirred for 6 hr. The reaction mixture was treated with saturated aqueous ammonium chloride solution, and extracted with dichloromethane. The extract was washed successively with hydrogencarbonate and saturated brine, dried over anhydrous magnesium sulfate, and concentrated under reduced pressure. The residue was purified by silica gel column chromatography (ethyl acetate:hexane=5:95-50:50) to give the title compound (6.58 g, yield 40%) as pale-brown crystals.

MS m/z 165 (M+H)$^+$.

Reference Example 11

2,3,5,6-tetramethylphenol

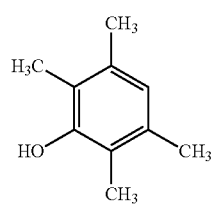

2-Hydroxy-3,4,6-trimethylbenzaldehyde (6.58 g, 40.1 mmol) was dissolved in methanol (120 mL), 10% palladium-carbon (50% water-containing product, 1.0 g) was added under hydrogen atmosphere (balloon pressure), and the mixture was stirred at room temperature for 22 hr. The catalyst was filtered off, and the filtrate was concentrated under reduced pressure. The precipitated crystals were recrystallized from methanol to give the title compound (0.73 g, yield 12%) as colorless crystals. The mother solution was concentrated under reduced pressure to give second crop (5.10 g, yield 85%). MS m/z 151 (M+H)$^+$.

Reference Example 12

4-bromo-2,3,5,6-tetramethylphenol

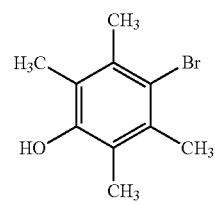

To a suspension of 2,3,5,6-tetramethylphenol (5.10 g, 34.0 mmol) in acetic acid (90 ml) was added dropwise a solution of bromine (1.98 mL, 38.6 mmol) in acetic acid (30 mL) at room temperature, and the mixture was stirred for 5 hr. The reaction mixture was concentrated under reduced pressure, and the residue was diluted with ethyl acetate, and washed successively with aqueous sodium thiosulfate solution and saturated brine. The organic layer was dried over anhydrous magnesium sulfate, and concentrated under reduced pressure. The precipitated crystals were washed with petroleum ether to give the title compound (5.10 g, yield 66%) as pale-yellow crystals. The mother solution was concentrated under reduced pressure, and washed with petroleum ether to give second crop (1.38 g, yield 18%).

$^1$H NMR (CDCl$_3$) δ: 2.23 (6H, s), 2.40 (6H, s), 4.59 (1H, s).

Reference Example 13

4'-hydroxy-2',3',5',6'-tetramethylbiphenyl-3-carbaldehyde

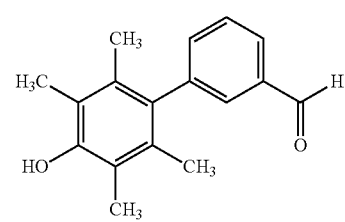 [SMILES: Cc1c(C)c(-c2cccc(C=O)c2)c(C)c(C)c1O]

In the same manner as in Reference Example 6, the title compound was obtained as colorless crystals from 4-bromo-2,3,5,6-tetramethylphenol and (3-formylphenyl)boronic acid.

yield 79%.

MS m/z 255 (M+H)$^+$.

Reference Example 14

3'-(hydroxymethyl)-2,3,5,6-tetramethylbiphenyl-4-ol

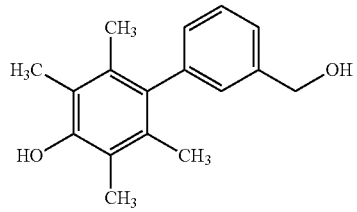 [SMILES: Cc1c(C)c(-c2cccc(CO)c2)c(C)c(C)c1O]

A solution of 4'-hydroxy-2',3',5',6'-tetramethylbiphenyl-3-carbaldehyde (2.03 g, 8.00 mmol) in a mixed solvent of methanol (10 mL) and tetrahydrofuran (20 mL) was ice-cooled, sodium borohydride (90%, 0.336 g, 8.00 mmol) was added, and the mixture was stirred for 2 hr under nitrogen atmosphere. The reaction mixture was treated with diluted hydrochloric acid, and extracted with ethyl acetate. The extract was washed with saturated brine, dried over anhydrous magnesium sulfate, and concentrated under reduced pressure. The obtained crystals were recrystallized from heptane-ethyl acetate to give the title compound (1.90 g, yield 93%) as colorless crystals.

melting point 152-153° C.

Reference Example 15

3-(methylthio)propyl 4-methylbenzenesulfonate

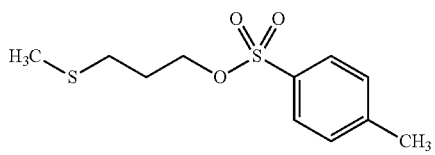

A solution of 3-(methylthio)-1-propanol (5.30 g, 50.0 mmol), triethylamine (10.5 mL, 75.0 mmol) and N,N,N',N'-tetramethyl-1,6-hexanediamine (0.861 g, 5.00 mmol) in toluene (50 mL) was ice-cooled, and a solution of p-toluenesulfonyl chloride (14.3 g, 75.0 mmol) in toluene (50 mL) was added dropwise under nitrogen atmosphere. After completion of the dropwise addition, the mixture was stirred for 3 hr, during which the mixture was allowed to warm to room temperature. Water was added to the reaction mixture, and the mixture was extracted with ethyl acetate. The extract was washed with saturated brine, dried over anhydrous sodium sulfate, and concentrated under reduced pressure. The residue was purified by silica gel column chromatography (ethyl acetate:hexane=10:90-40:60) to give the title compound (12.2 g, yield 94%) as a colorless oil.

MS m/z 261 (M+H)$^+$.

Reference Example 16

3-(methylsulfonyl)propyl 4-methylbenzenesulfonate

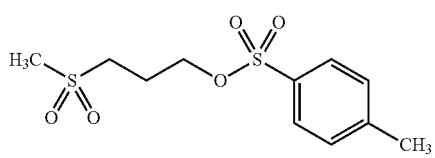

To a solution of 3-(methylthio)propyl 4-methylbenzenesulfonate (12.2 g, 46.9 mmol) in methanol (250 mL) was added dropwise a solution of potassium peroxysulfate (trade name: OXONE, 57.7 g, 93.8 mmol) in water (250 mL) under ice-cooling. After completion of the dropwise addition, the mixture was stirred for 20 hr, during which the mixture was allowed to gradually warm to room temperature. Methanol was evaporated under reduced pressure, and the mixture was diluted with water, and the organic material was extracted with ethyl acetate. The extract was washed with saturated brine, dried over anhydrous sodium sulfate, and concentrated under reduced pressure. The precipitated crystals were washed with ethyl acetate-heptane to give the title compound (13.1 g, yield 96%) as colorless crystals.

MS m/z 293 (M+H)$^+$.

Reference Example 17

{2',3',5',6'-tetramethyl-4'-[3-(methylsulfonyl)propoxy]biphenyl-3-yl}methanol

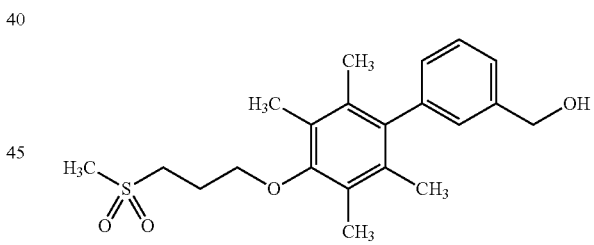

To a solution of 3'-(hydroxymethyl)-2,3,5,6-tetramethylbiphenyl-4-ol (0.616 g, 2.40 mmol) and 3-(methylsulfonyl)propyl 4-methylbenzenesulfonate (1.05 g, 3.60 mmol) in N,N-dimethylformamide (5 mL) was added potassium carbonate (0.597 g, 4.32 mmol), and the mixture was stirred at 90° C. for 12 hr under nitrogen atmosphere. Water was added to the reaction mixture, and the mixture was extracted with ethyl acetate. The extract was washed successively with 1 M aqueous sodium hydroxide solution and saturated brine, dried over anhydrous magnesium sulfate, and concentrated under reduced pressure. The residue was purified by silica gel column chromatography (ethyl acetate:hexane=40:60-80:20), and the obtained crystals were recrystallized from heptane-ethyl acetate to give the title compound (0.577 g, yield 85%) as colorless crystals.

melting point 132-134° C.

Reference Example 18

2',6'-dimethyl-4'-[3-(methylsulfonyl)propoxy]biphenyl-3-carbaldehyde

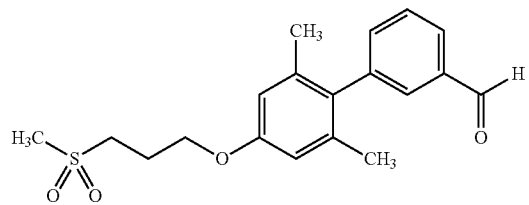 [SMILES: Cc1cc(OCCCS(C)(=O)=O)cc(C)c1-c1cccc(C=O)c1]

To a solution of 4'-hydroxy-2',6'-dimethylbiphenyl-3-carbaldehyde (2.26 g, 10.0 mmol) and 3-(methylsulfonyl)propyl 4-methylbenzenesulfonate (3.51 g, 12.0 mmol) in N,N-dimethylformamide (20 mL) was added potassium carbonate (1.80 g, 13.0 mmol), and the mixture was stirred at 90° C. for 24 hr under nitrogen atmosphere. Water was added to the reaction mixture, and the mixture was extracted with ethyl acetate. The extract was washed successively with 1 M aqueous sodium hydroxide solution and saturated brine, dried over anhydrous magnesium sulfate, and concentrated under reduced pressure. The residue was purified by silica gel column chromatography (ethyl acetate:hexane=40:60-80:20), and the obtained crystals were recrystallized from heptane-ethyl acetate to give the title compound (2.68 g, yield 77%) as colorless crystals.

MS m/z 347 (M+H)$^+$.

Reference Example 19

{2',6'-dimethyl-4'-[3-(methylsulfonyl)propoxy]biphenyl-3-yl}methanol

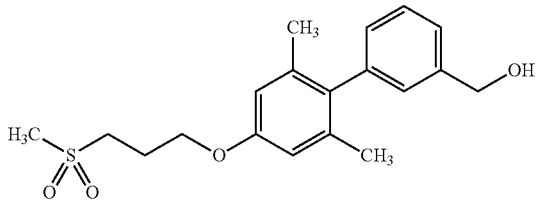 [SMILES: Cc1cc(OCCCS(C)(=O)=O)cc(C)c1-c1cccc(CO)c1]

A solution of 2',6'-dimethyl-4'-[3-(methylsulfonyl)propoxy]biphenyl-3-carbaldehyde (2.66 g, 7.68 mmol) in a mixed solvent of methanol (10 mL) and tetrahydrofuran (20 mL) was ice-cooled, sodium borohydride (90%, 0.323 g, 7.68 mmol) was added, and the mixture was stirred for 6 hr under nitrogen atmosphere. The reaction mixture was treated with diluted hydrochloric acid, and extracted with ethyl acetate. The extract was washed with saturated brine, dried over anhydrous magnesium sulfate, and concentrated under reduced pressure. The obtained crystals were recrystallized from heptane-ethyl acetate to give the title compound (2.60 g, yield 97%) as colorless crystals.

$^1$H NMR (CDCl$_3$) δ: 1.68 (1H, t, J=5.9 Hz), 2.00 (6H, s), 2.30-2.40 (2H, m), 2.97 (3H, s), 3.24-3.31 (2H, m), 4.13 (2H, t, J=5.7 Hz), 4.73 (2H, d, J=5.9 Hz), 6.64 (2H, s), 7.03-7.08 (1H, m), 7.12 (1H, s), 7.31-7.37 (1H, m), 7.41 (1H, t, J=7.5 Hz).

Reference Example 20

3'-(hydroxymethyl)-2,6-dimethylbiphenyl-4-ol

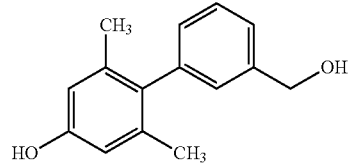 [SMILES: Cc1cc(O)cc(C)c1-c1cccc(CO)c1]

A solution of 4'-hydroxy-2',6'-dimethylbiphenyl-3-carbaldehyde (6.95 g, 30.7 mmol) in a mixed solvent of methanol (30 mL) and tetrahydrofuran (60 mL) was ice-cooled, sodium borohydride (90%, 1.29 g, 30.7 mmol) was added, and the mixture was stirred for 20 hr under nitrogen atmosphere, during which the mixture was allowed to gradually warm to room temperature. The reaction mixture was concentrated under reduced pressure, the residue was treated with diluted hydrochloric acid, and the mixture was extracted with ethyl acetate. The extract was washed with saturated brine, dried over anhydrous magnesium sulfate, and concentrated under reduced pressure. The obtained crystals were recrystallized from heptane-ethyl acetate to give the title compound (6.56 g, yield 93%) as colorless crystals.

melting point 175° C.

Reference Example 21

{4'-[2-(ethylthio)ethoxy]-2',6'-dimethylbiphenyl-3-yl}methanol

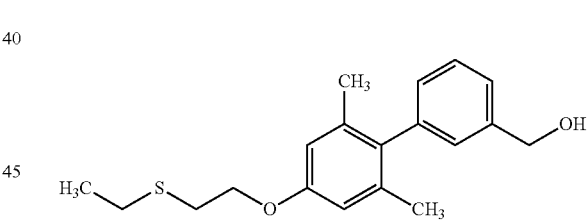

To a solution of 3'-(hydroxymethyl)-2,6-dimethylbiphenyl-4-ol (1.83 g, 8.00 mmol) and 2-chloroethyl ethyl sulfide (1.07 mL, 12.0 mmol) in N,N-dimethylformamide (15 mL) were added potassium carbonate (1.33 g, 9.60 mmol) and potassium iodide (0.132 g, 0.800 mmol), and the mixture was stirred at 95° C. for 24 hr under nitrogen atmosphere. Water was added to the reaction mixture, and the mixture was extracted with ethyl acetate. The extract was washed successively with 1 M aqueous sodium hydroxide solution and saturated brine, dried over anhydrous magnesium sulfate, and concentrated under reduced pressure. The residue was purified by silica gel column chromatography (ethyl acetate:hexane=10:90-50:50) to give the title compound (1.19 g, yield 47%) as a colorless oil.

$^1$H NMR (CDCl$_3$) δ: 1.31 (3H, t, J=7.3 Hz), 1.67 (1H, t, J=5.8 Hz), 2.00 (6H, s), 2.67 (2H, q, J=7.3 Hz), 2.92 (2H, t, J=7.0 Hz), 4.16 (2H, t, J=7.0 Hz), 4.73 (2H, d, J=5.8 Hz), 6.66 (2H, s), 7.06 (1H, dt, J=7.3, 1.3 Hz), 7.12 (1H, s), 7.30-7.36 (1H, m), 7.41 (1H, t, J=7.3 Hz).

Reference Example 22 methyl [(3S)-6-({4'-[2-(ethylthio)ethoxy]-2',6'-dimethylbiphenyl-3-yl}methoxy)-2,3-dihydro-1-benzofuran-3-yl]acetate

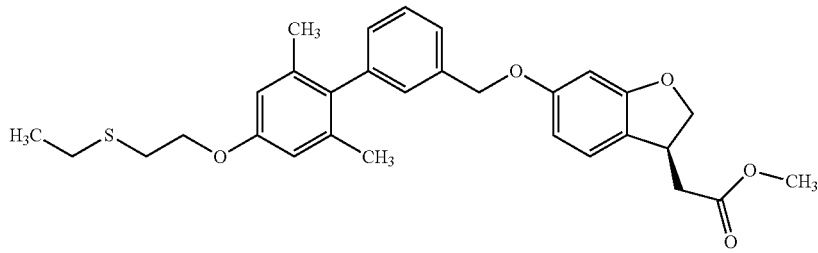 [SMILES: CCSCCOc1cc(C)c(-c2cccc(COc3ccc4c(c3)OC[C@H]4CC(=O)OC)c2)c(C)c1]

A solution of methyl [(3S)-6-hydroxy-2,3-dihydro-1-benzofuran-3-yl]acetate (0.250 g, 1.20 mmol), {4'-[2-(ethylthio)ethoxy]-2',6'-dimethylbiphenyl-3-yl}methanol (0.380 g, 1.20 mmol) and tributylphosphine (0.388 g, 1.92 mmol) in toluene (20 mL) was stirred, 1,1'-(azodicarbonyl)dipiperidine (0.484 g, 1.92 mmol) was added, and the mixture was stirred at room temperature for 1 hr under nitrogen atmosphere. Hexane (10 mL) was added to the reaction mixture, the precipitated insoluble substance was filtered off, and the filtrate was concentrated under reduced pressure. The residue was purified by silica gel column chromatography (ethyl acetate:hexane=5:95-40:60) to give the title compound (0.363 g, yield 60%) as a pale-yellow oil.

MS m/z 507 (M+H)+.

Reference Example 23

[(3S)-6-({4'-[2-(ethylthio)ethoxy]-2',6'-dimethylbiphenyl-3-yl}methoxy)-2,3-dihydro-1-benzofuran-3-yl]acetic acid

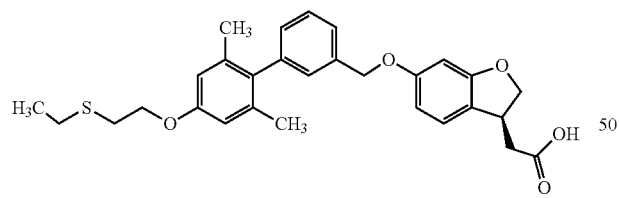

To a solution of methyl [(3S)-6-({4'-[2-(ethylthio)ethoxy]-2',6'-dimethylbiphenyl-3-yl}methoxy)-2,3-dihydro-1-benzofuran-3-yl]acetate (0.358 g, 0.707 mmol) in a mixed solvent of methanol (1.5 mL) and tetrahydrofuran (3 mL) was added 2 M aqueous sodium hydroxide solution (0.750 mL), and the mixture was stirred at 50° C. for 1.5 hr. The reaction mixture was diluted with water, acidified with 1 M hydrochloric acid, and extracted with ethyl acetate. The extract was washed with saturated brine, dried over anhydrous magnesium sulfate, and concentrated under reduced pressure to give the title compound (0.309 g, yield 89%) as a colorless oil.

MS m/z 493 (M+H)+.

Reference Example 24

4-bromo-2-fluoro-3,5-dimethylphenol

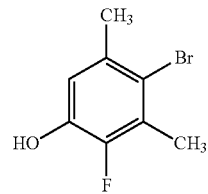

To a solution of 4-bromo-3,5-dimethylphenol (2.00 g, 9.95 mmol) in 1,2-dichloroethane (20 mL) was added N-fluoropyridinium triflate (6.15 g, 24.9 mmol), and the mixture was heated under reflux for 7 hr. The reaction mixture was treated with 1 M aqueous sodium thiosulfate solution, and extracted with ethyl acetate. The extract was washed successively with water and saturated brine, dried over anhydrous magnesium sulfate, and concentrated under reduced pressure. The residue was purified by silica gel column chromatography (ethyl acetate:hexane=0:100-30:70) to give the title compound (0.790 g, yield 36%) as a colorless oil.

1H NMR (CDCl3) δ: 2.29-2.36 (6H, m), 5.04 (1H, d, J=4.0 Hz), 6.79 (1H, d, J=9.0 Hz).

Reference Example 25

3'-fluoro-4'-hydroxy-2',6'-dimethylbiphenyl-3-carbaldehyde

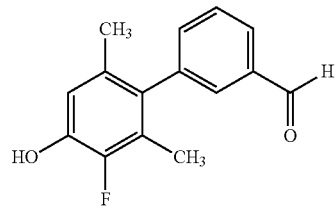

In the same manner as in Reference Example 6, the title compound was obtained as colorless crystals from 4-bromo-2-fluoro-3,5-dimethylphenol and (3-formylphenyl)boronic acid.

yield 49%.

MS m/z 245 (M+H)$^+$.

Reference Example 26

3'-fluoro-2',6'-dimethyl-4'-[3-(methylsulfonyl)propoxy]biphenyl-3-carbaldehyde

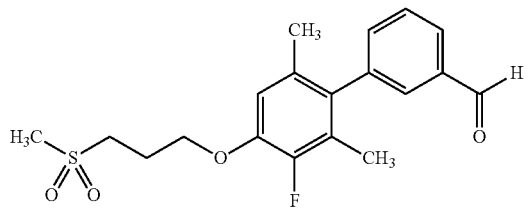 [SMILES: Cc1cc(OCCCS(C)(=O)=O)c(F)c(C)c1-c1cccc(C=O)c1]

To a solution of 3'-fluoro-4'-hydroxy-2',6'-dimethylbiphenyl-3-carbaldehyde (2.44 g, 10.0 mmol) and 3-(methylsulfonyl)propyl 4-methylbenzenesulfonate (3.51 g, 12.0 mmol) in N,N-dimethylformamide (20 mL) was added potassium carbonate (1.80 g, 13.0 mmol), and the mixture was stirred at 90° C. for 24 hr under nitrogen atmosphere. Water was added to the reaction mixture, and the mixture was extracted with ethyl acetate. The extract was washed successively with 1 M aqueous sodium hydroxide solution and saturated brine, dried over anhydrous magnesium sulfate, and concentrated under reduced pressure. The residue was purified by silica gel column chromatography (ethyl acetate:hexane=40:60-80:20), and the obtained crystals were recrystallized from heptane-ethyl acetate to give the title compound (3.45 g, yield 95%) as colorless crystals.

MS m/z 365 (M+H)$^+$.

Reference Example 27

{3'-fluoro-2',6'-dimethyl-4'-[3-(methylsulfonyl)propoxy]biphenyl-3-yl}methanol

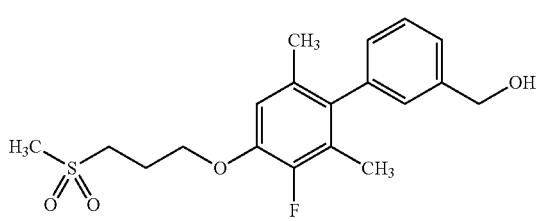 [SMILES: Cc1cc(OCCCS(C)(=O)=O)c(F)c(C)c1-c1cccc(CO)c1]

A solution of 3'-fluoro-2',6'-dimethyl-4'-[3-(methylsulfonyl)propoxy]biphenyl-3-carbaldehyde (2.77 g, 8.00 mmol) in a mixed solvent of methanol (10 mL) and tetrahydrofuran (20 mL) was ice-cooled, sodium borohydride (90%, 0.336 g, 8.00 mmol) was added, and the mixture was stirred for 8 hr under nitrogen atmosphere. The reaction mixture was treated with diluted hydrochloric acid, and extracted with ethyl acetate. The extract was washed with saturated brine, dried over anhydrous magnesium sulfate, and concentrated under reduced pressure. The residue was purified by silica gel column chromatography (ethyl acetate:hexane=40:60-80:20), and the obtained crystals were recrystallized from heptane-ethyl acetate to give the title compound (2.75 g, yield 94%) as colorless crystals.

$^1$H NMR (CDCl$_3$) δ: 1.67 (1H, t, J=5.9 Hz), 1.91-1.95 (3H, m), 1.97 (3H, s), 2.32-2.45 (2H, m), 2.98 (3H, s), 3.27-3.35 (2H, m), 4.20 (2H, t, J=5.8 Hz), 4.74 (2H, d, J=5.9 Hz), 6.70 (1H, d, J=8.3 Hz), 7.03 (1H, d, J=7.5 Hz), 7.10 (1H, s), 7.32-7.47 (2H, m).

Reference Example 28

4-(chloromethyl)-7-hydroxy-2H-chromen-2-one

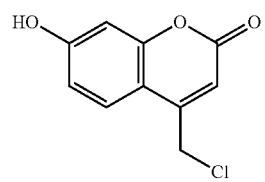

Under ice-cooling, ethyl 4-chloroacetoacetate (14.0 g, 85.0 mmol) was dissolved in concentrated sulfuric acid (30 mL), resorcinol (8.81 g, 80.0 mmol) was added by small portions, and the mixture was stirred at room temperature for 2 hr. The reaction mixture was poured into ice water, and the precipitated solid was collected by filtration, washed with water, and air-dried to give the title compound (14.1 g, yield 84%) as a beige powder.

MS m/z 211 (M+H)$^+$.

Reference Example 29

(6-hydroxy-1-benzofuran-3-yl)acetic acid

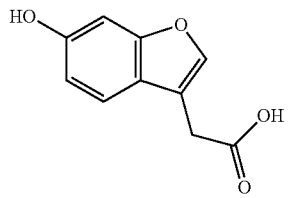 [SMILES: O=C(O)Cc1coc2cc(O)ccc12]

4-(Chloromethyl)-7-hydroxy-2H-chromen-2-one (10.9 g, 51.8 mmol) was dissolved in 1 M aqueous sodium hydroxide solution (500 mL), and the mixture was heated under reflux for 2 hr. The reaction mixture was allowed to cool, acidified with concentrated sulfuric acid, and extracted with ethyl acetate. The extract was washed with saturated brine, dried over anhydrous magnesium sulfate, and concentrated under reduced pressure to give the title compound (8.27 g, yield 83%) as brown crystals.

MS m/z 193 (M+H)$^+$.

Reference Example 30 methyl (6-hydroxy-1-benzofuran-3-yl) acetate

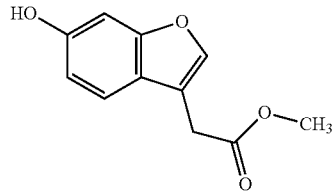

(6-Hydroxy-1-benzofuran-3-yl)acetic acid (9.85 g, 51.3 mmol) was suspended in methanol (45 mL), concentrated sulfuric acid (5 mL) was added, and the mixture was heated under reflux for 4 hr. The reaction mixture was concentrated under reduced pressure, water was added, and the mixture was extracted with diethyl ether. The extract was washed successively with saturated aqueous sodium hydrogencarbonate and saturated brine, dried over anhydrous magnesium sulfate, and concentrated under reduced pressure. The residue was purified by silica gel column chromatography (ethyl acetate:hexane=10:90-50:50.), and the obtained crystals were recrystallized from ethyl acetate-hexane to give the title compound (7.38 g, yield 70%) as pale-yellow prisms.

MS m/z 207 (M+H)$^+$.

Reference Example 31 methyl (6-hydroxy-2,3-dihydro-1-benzofuran-3-yl)acetate

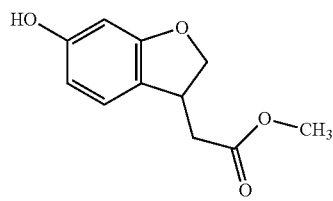

To a solution of methyl (6-hydroxy-1-benzofuran-3-yl)acetate (11.4 g, 55.3 mmol) in methanol (100 mL) was added 10% palladium-carbon (50% water-containing product, 2 g), and the mixture was stirred at room temperature for 18 hr under hydrogen atmosphere (balloon pressure). The catalyst was filtered off, and the filtrate was concentrated under reduced pressure. The residue was purified by silica gel column chromatography (ethyl acetate:hexane=20:80-50:50), and the obtained solid was recrystallized from ethyl acetate-hexane to give the title compound (8.74 g, yield 76%) as colorless prisms.

MS m/z 209 (M+H)$^+$.

Reference Example 32

4-bromo-3,5-dimethylphenyl acetate

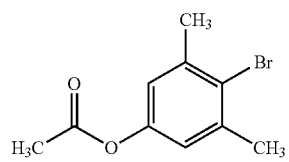

To a solution of 4-bromo-3,5-dimethylphenol (10.1 g, 50.0 mmol) in pyridine (13 mL) was added acetic anhydride (7.66 g, 38.6 mmol), and the mixture was stirred at 50° C. for 30 min. The reaction mixture was ice-cooled, diluted with 0.5 M hydrochloric acid, and extracted with ethyl acetate. The extract was washed with saturated brine, dried over anhydrous magnesium sulfate, and concentrated under reduced pressure to give the title compound (12.1 g, yield 99%) as a yellow oil.

$^1$H NMR (CDCl$_3$) δ: 2.28 (3H, s), 2.40 (6H, s), 6.82 (2H, s).

Reference Example 33

4-bromo-3-(bromomethyl)-5-methylphenyl acetate

A suspension of 4-bromo-3,5-dimethylphenyl acetate (12.1 g, 49.8 mmol), N-bromosuccinimide (9.79 g, 55.0 mmol) and 2,2'-azobisisobutyronitrile (82.1 mg, 0.500 mmol) in carbon tetrachloride (100 mL) was stirred at 75° C. for 5 hr under nitrogen atmosphere. The reaction mixture was ice-cooled, and concentrated under reduced pressure. The residue was diluted with diethyl ether, the insoluble substance was filtered off, and the filtrate was concentrated under reduced pressure. The residue was purified by silica gel column chromatography (ethyl acetate:hexane=0:100-25:75) to give the title compound (11.7 g, yield 73%) as colorless crystals.

$^1$H NMR (CDCl$_3$) δ: 2.29 (3H, s), 2.43 (3H, s), 4.60 (2H, s), 6.97 (1H, d, J=2.7 Hz), 7.07 (1H, d, J=2.7 Hz).

Reference Example 34

5-acetoxy-2-bromo-3-methylbenzyl acetate

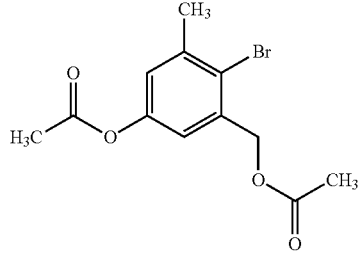 [SMILES: CC(=O)OCc1cc(OC(C)=O)cc(C)c1Br]

To a solution of 4-bromo-3-(bromomethyl)-5-methylphenyl acetate (11.7 g, 36.3 mmol) in N,N-dimethylformamide (60 mL) was added sodium acetate (5.96 g, 72.6 mmol), and the mixture was stirred at 70° C. for 4 hr under nitrogen atmosphere. Ethyl acetate was added to the reaction mixture, and the mixture was washed successively with water and saturated brine, dried over anhydrous magnesium sulfate, and concentrated under reduced pressure. The residue was purified by silica gel column chromatography (ethyl acetate:hexane=0:100-25:75) to give the title compound (7.29 g, yield 67%) as a pale-yellow oil.

$^1$H NMR (CDCl$_3$) δ: 2.15 (3H, s), 2.30 (3H, s), 2.42 (3H, s), 5.18 (2H, s), 6.95-7.03 (2H, m).

Reference Example 35

(4-acetoxy-3'-formyl-6-methylbiphenyl-2-yl)methyl acetate

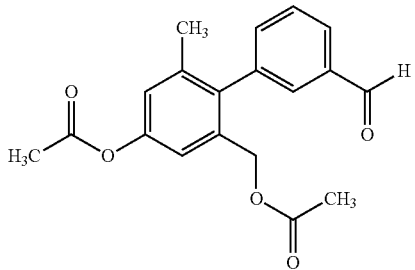 [SMILES: CC(=O)OCc1cc(OC(C)=O)cc(C)c1-c1cccc(C=O)c1]

In the same manner as in Reference Example 6, the title compound was obtained as a yellow oil from 5-acetoxy-2-bromo-3-methylbenzyl acetate and (3-formylphenyl)boronic acid. yield 50%.

$^1$H NMR (CDCl$_3$) δ: 2.00 (3H, s), 2.03 (3H, s), 2.33 (3H, s), 4.74 (2H, s), 7.02 (1H, d, J=2.5 Hz), 7.07 (1H, d, J=2.5 Hz), 7.43-7.48 (1H, m), 7.62 (1H, t, J=7.6 Hz), 7.71 (1H, t, J=1.7 Hz), 7.88-7.93 (1H, m), 10.05 (1H, s).

Reference Example 36

[4-hydroxy-3'-(hydroxymethyl)-6-methylbiphenyl-2-yl]methyl acetate

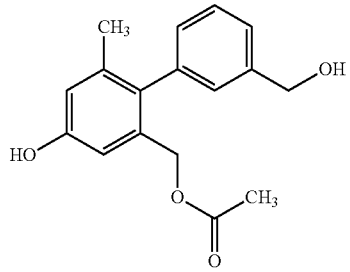 [SMILES: CC(=O)OCc1cc(O)cc(C)c1-c1cccc(CO)c1]

To a solution of (4-acetoxy-3'-formyl-6-methylbiphenyl-2-yl)methyl acetate (1.63 g, 4.99 mmol) in a mixed solvent of tetrahydrofuran (10 mL) and methanol (5 mL) was added sodium borohydride (90%, 0.210 g, 5.00 mmol) under ice-cooling, and the mixture was stirred at the same temperature for 3 hr under nitrogen atmosphere. Aqueous citric acid solution was added to the reaction mixture, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=20:80-80:20) to give the title compound (1.02 g, yield 71%) as a colorless oil.

$^1$H NMR (CDCl$_3$) δ: 2.00 (3H, s), 2.01 (3H, s), 4.72 (2H, s), 4.75 (2H, s), 5.20 (1H, br s), 6.73 (1H, d, J=2.5 Hz), 6.78 (1H, d, J=2.5 Hz), 7.05-7.11 (1H, m), 7.15 (1H, s), 7.31-7.43 (2H, m).

Reference Example 37

{3'-(hydroxymethyl)-6-methyl-4-[3-(methylsulfonyl)propoxy]biphenyl-2-yl}methyl acetate

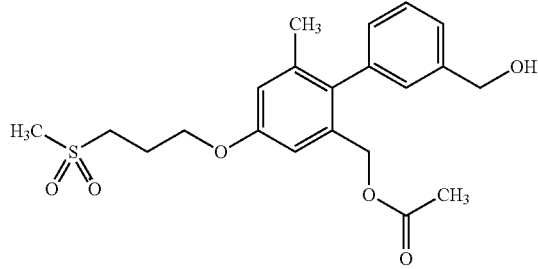

To a solution of [4-hydroxy-3'-(hydroxymethyl)-6-methylbiphenyl-2-yl]methyl acetate (1.02 g, 3.56 mmol) and 3-(methylsulfonyl)propyl 4-methylbenzenesulfonate (1.25 g, 4.27 mmol) in N,N-dimethylformamide (10 mL) was added potassium carbonate (0.640 g, 4.32 mmol), and the mixture was stirred at 90° C. for 21 hr under nitrogen atmosphere. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=50:50-100:0) to give the title compound (0.87 g, yield 60%) as a colorless oil.

¹H NMR (CDCl₃) δ: 1.81 (1H, t, J=6.0 Hz), 2.01 (3H, s), 2.03 (3H, s), 2.31-2.43 (2H, m), 2.97 (3H, s), 3.24-3.32 (2H, m), 4.16 (2H, t, J=5.7 Hz), 4.72 (2H, d, J=6.0 Hz), 4.76 (2H, s), 6.78 (1H, d, J=2.5 Hz), 6.83 (1H, d, J=2.5 Hz), 7.05-7.10 (1H, m), 7.15 (1H, s), 7.32-7.43 (2H, m).

Reference Example 38 methyl [(3S)-6-({2'-(acetoxymethyl)-6'-methyl-4'-[3-(methylsulfonyl)propoxy]biphenyl-3-yl}methoxy)-2,3-dihydro-1-benzofuran-3-yl]acetate

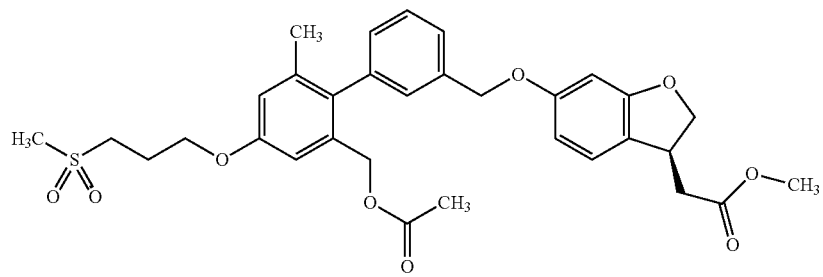

A solution of methyl [(3S)-6-hydroxy-2,3-dihydro-1-benzofuran-3-yl]acetate (0.208 g, 1.00 mmol), {3'-(hydroxymethyl)-6-methyl-4-[3-(methylsulfonyl)propoxy]biphenyl-2-yl}methyl acetate (0.360 g, 1.00 mmol) and tributylphosphine (0.324 g, 1.60 mmol) in toluene (15 mL) was stirred, 1,1'-(azodicarbonyl)dipiperidine (0.404 g, 1.60 mmol) was added, and the mixture was stirred at room temperature for 3 hr under nitrogen atmosphere. Hexane (8 mL) was added to the reaction mixture, the precipitated insoluble substance was filtered off, and the filtrate was concentrated under reduced pressure. The residue was purified by silica gel column chromatography (ethyl acetate:hexane=30:70-70:30) to give the title compound (0.432 g, yield 79%) as a colorless oil.

¹H NMR (CDCl₃) δ: 2.01 (6H, s), 2.31-2.42 (2H, m), 2.50-2.61 (1H, m), 2.70-2.80 (1H, m), 2.98 (3H, s), 3.24-3.32 (2H, m), 3.72 (3H, s), 3.75-3.86 (1H, m), 4.12-4.18 (2H, m), 4.26 (1H, dd, J=9.2, 6.0 Hz), 4.71-4.79 (3H, m), 5.04 (2H, s), 6.43-6.50 (2H, m), 6.78 (1H, d, J=2.5 Hz), 6.83 (1H, d, J=2.5 Hz), 7.02 (1H, d, J=7.9 Hz), 7.07-7.12 (1H, m), 7.19 (1H, s), 7.36-7.45 (2H, m).

Reference Example 39

3'-chloro-4'-hydroxy-2',6'-dimethylbiphenyl-3-carbaldehyde

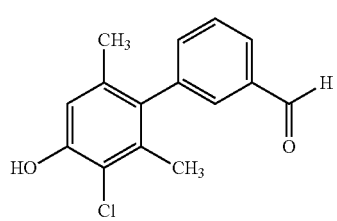

To a solution of 4'-hydroxy-2',6'-dimethylbiphenyl-3-carbaldehyde (11.3 g, 50.0 mmol) in N,N-dimethylformamide (50 mL) was added N-chlorosuccinimide (6.68 g, 50.0 mmol) by small portions under ice-cooling, and the mixture was stirred at room temperature for 13 hr, and then at 50° C. for 3 hr. N-Chlorosuccinimide (1.34 g, 10.0 mmol) was added to the reaction mixture, and the mixture was stirred at the same temperature for 3 hr. N-Chlorosuccinimide (0.668 g, 5.00 mmol) was added again, and the mixture was further stirred at the same temperature for 1 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=5:95-40:60), and the obtained crystals were recrystallized from ethyl acetate-heptane to give the title compound (8.47 g, yield 65%) as colorless crystals.

MS m/z 261 (M+H)⁺.

Reference Example 40

4'-{[tert-butyl(dimethyl)silyl]oxy}-3'-chloro-2',6'-dimethylbiphenyl-3-carbaldehyde

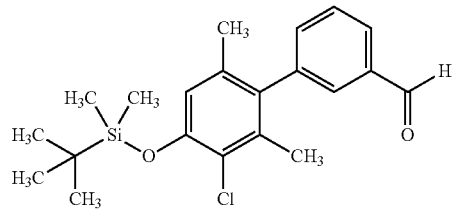 [SMILES: Cc1cc(O[Si](C)(C)C(C)(C)C)c(Cl)c(C)c1-c1cccc(C=O)c1]

To a solution of 3'-chloro-4'-hydroxy-2',6'-dimethylbiphenyl-3-carbaldehyde (1.41 g, 5.41 mmol) and imidazole (1.10 g, 16.2 mmol) in N,N-dimethylformamide (10 mL), was added tert-butyldimethylchlorosilane (1.22 g, 8.09 mmol) at room temperature, and the mixture was stirred at room temperature for 24 hr under nitrogen atmosphere. Water was added to the reaction mixture, and the mixture was extracted with diethyl ether. The extract was washed with saturated brine, dried over anhydrous sodium sulfate, and concentrated under reduced pressure. The residue was purified by silica gel column chromatography (ethyl acetate:hexane=0:100-20:80) to give the title compound (1.78 g, yield 88%) as a colorless oil.

MS m/z 375 (M+H)⁺.

Reference Example 41

(4'-{[tert-butyl(dimethyl)silyl]oxy}-3'-chloro-2',6'-dimethylbiphenyl-3-yl)methanol

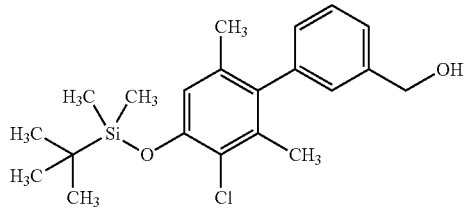 [SMILES: Cc1cc(O[Si](C)(C)C(C)(C)C)c(Cl)c(C)c1-c1cccc(CO)c1]

To a solution of 4'-{[tert-butyl(dimethyl)silyl]oxy}-3'-chloro-2',6'-dimethylbiphenyl-3-carbaldehyde (1.78 g, 4.75 mmol) in a mixed solvent of in tetrahydrofuran (10 mL) and methanol (5 mL) was added sodium borohydride (90%, 90 mg, 2.38 mmol) under ice-cooling, and the mixture was stirred at the same temperature for 2 hr under nitrogen atmosphere. Water was added to the reaction mixture, and the mixture was extracted with ethyl acetate. The extract was washed with saturated brine, dried over anhydrous sodium sulfate, and concentrated under reduced pressure. The residue was purified by silica gel column chromatography (ethyl acetate:hexane=5:95-40:60) to give the title compound (1.74 g, yield 97%) as a colorless oil.

MS m/z 377 (M+H)$^+$.

Reference Example 42 methyl {(3S)-6-[(4'-{[tert-butyl(dimethyl)silyl]oxy}-3'-chloro-2',6'-dimethylbiphenyl-3-yl)methoxy]-2,3-dihydro-1-benzofuran-3-yl}acetate

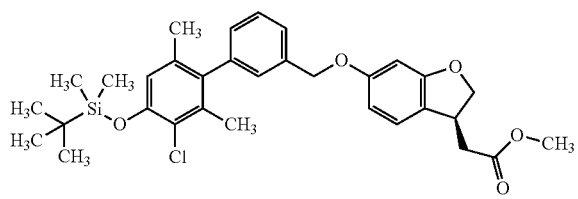 [SMILES: COC(=O)C[C@@H]1COc2cc(OCc3cccc(-c4c(C)cc(O[Si](C)(C)C(C)(C)C)c(Cl)c4C)c3)ccc21]

In the same manner as in Reference Example 22, the title compound was obtained as colorless crystals from (4'-{[tert-butyl(dimethyl)silyl]oxy}-3'-chloro-2',6'-dimethylbiphenyl-3-yl)methanol and methyl [(3S)-6-hydroxy-2,3-dihydro-1-benzofuran-3-yl]acetate. yield 77%.

MS m/z 567 (M+H)$^+$.

Reference Example 43 methyl {(3S)-6-[(3'-chloro-4'-hydroxy-2',6'-dimethylbiphenyl-3-yl)methoxy]-2,3-dihydro-1-benzofuran-3-yl}acetate

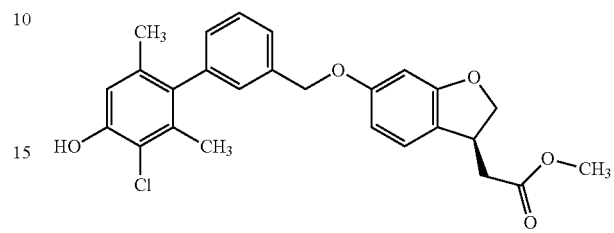

To a solution of methyl {(3S)-6-[(4'-{[tert-butyl(dimethyl)silyl]oxy}-3'-chloro-2',6'-dimethylbiphenyl-3-yl)methoxy]-2,3-dihydro-1-benzofuran-3-yl}acetate (2.01 g, 3.54 mmol) in tetrahydrofuran (20 mL) was added 1 M tetrabutylammonium fluoride tetrahydrofuran solution (3.9 mL, 3.9 mmol) at room temperature, and the mixture was stirred at the same temperature for 3 hr under nitrogen atmosphere. The reaction mixture was concentrated under reduced pressure, water was added to the residue, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=10:90-50:50) to give the title compound (1.41 g, yield 88%) as a colorless oil.

MS m/z 453 (M+H)$^+$.

Reference Example 44

3',5'-dichloro-4'-hydroxy-2',6'-dimethylbiphenyl-3-carbaldehyde

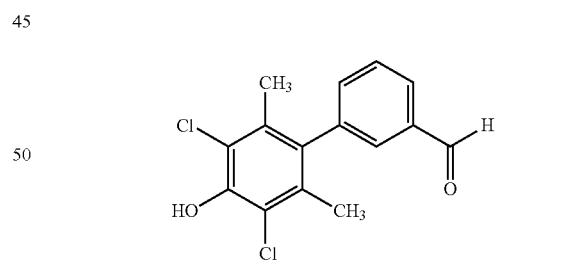

To a solution of 4'-hydroxy-2',6'-dimethylbiphenyl-3-carbaldehyde (11.3 g, 50.0 mmol) in N,N-dimethylformamide (50 mL) was added N-chlorosuccinimide (13.4 g, 100 mmol) by small portions under ice-cooling, and the mixture was stirred at room temperature for 14 hr, and then at 50° C. for 2 hr. Water was added to the reaction mixture, and the mixture was extracted with ethyl acetate. The extract was washed with saturated brine, dried over anhydrous magnesium sulfate, and concentrated under reduced pressure. The precipitated crystals were washed with ethyl acetate-heptane to give the title compound (8.88 g, yield 60%) as colorless crystals.

¹H NMR (CDCl₃) δ: 2.03 (6H, s), 6.00 (1H, s), 7.35-7.40 (1H, m), 7.60-7.66 (2H, m), 7.88-7.94 (1H, m), 10.06 (1H, s).

Reference Example 45

3',5'-dichloro-2',6'-dimethyl-4'-[3-(methylsulfonyl)propoxy]biphenyl-3-carbaldehyde

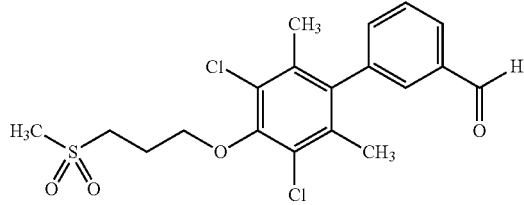 [SMILES: Cc1c(Cl)c(OCCCS(C)(=O)=O)c(Cl)c(C)c1-c1cccc(C=O)c1]

In the same manner as in Reference Example 18, the title compound was obtained as colorless crystals from 3',5'-dichloro-4'-hydroxy-2',6'-dimethylbiphenyl-3-carbaldehyde and 3-(methylsulfonyl)propyl 4-methylbenzenesulfonate. yield 53%.

¹H NMR (CDCl₃) δ: 2.03 (6H, s), 2.37-2.48 (2H, m), 3.00 (3H, s), 3.44-3.51 (2H, m), 4.18 (2H, t, J=5.7 Hz), 7.34-7.39 (1H, m), 7.61-7.68 (2H, m), 7.89-7.94 (1H, m), 10.06 (1H, s).

Reference Example 46

[3',5'-dichloro-2',6'-dimethyl-4'-[3-(methylsulfonyl)propoxy]biphenyl-3-yl}methanol

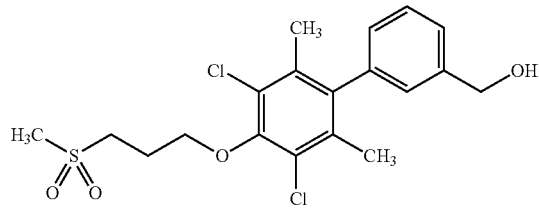 [SMILES: Cc1c(Cl)c(OCCCS(C)(=O)=O)c(Cl)c(C)c1-c1cccc(CO)c1]

In the same manner as in Reference Example 41, the title compound was obtained as a colorless oil from 3',5'-dichloro-2',6'-dimethyl-4'-[3-(methylsulfonyl)propoxy]biphenyl-3-carbaldehyde. yield 98%.

¹H NMR (CDCl₃) δ: 1.76 (1H, t, J=5.7 Hz), 2.03 (6H, s), 2.36-2.47 (2H, m), 3.00 (3H, s), 3.43-3.51 (2H, m), 4.16 (2H, t, J=5.7 Hz), 4.75 (2H, d, J=5.7 Hz), 6.97-7.03 (1H, m), 7.07-7.08 (1H, m), 7.36-7.48 (2H, m).

Reference Example 47

3,5-diethylphenol

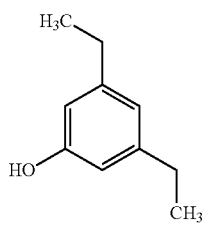

A mixture of 4-ethylphenol (25.7 g, 210 mmol) and aluminum chloride (62.5 g, 469 mmol) was stirred at 115° C. for 4 hr under nitrogen atmosphere. The reaction mixture was cooled to 60° C., and poured into ice water, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=0:100-25:75) to give the title compound (12.3 g, yield 78%) as a red-brown oil.

MS m/z 151 (M+H)⁺.

Reference Example 48

4-bromo-3,5-diethylphenol

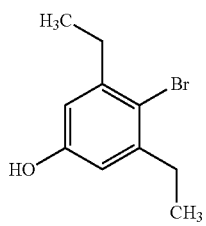

To a solution of 3,5-diethylphenol (9.30 g, 61.9 mmol) in methanol (100 mL) was added tetrabutylammonium tribromide (29.8 g, 61.9 mmol), and the mixture was stirred at room temperature for 15 hr. The solvent was evaporated under reduced pressure, water was added to the residue, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=0:100-25:75), and the obtained crystals were recrystallized from heptane to give the title compound (1.85 g) as colorless crystals. The mother liquor was concentrated under reduced pressure to give the title compound (8.68 g) as dark-brown crystals (total 10.5 g, total yield 74%).

¹H NMR (CDCl₃) δ: 1.21 (6H, t, J=7.6 Hz), 2.73 (4H, q, J=7.6 Hz), 4.65 (1H, s), 6.59 (2H, s).

Reference Example 49

2',6'-diethyl-4'-hydroxybiphenyl-3-carbaldehyde

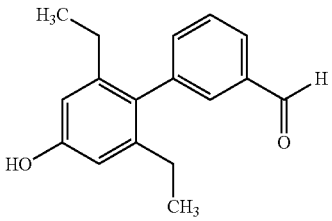 [SMILES: CCc1cc(O)cc(CC)c1-c1cccc(C=O)c1]

In the same manner as in Reference Example 6, the title compound was obtained as a yellow oil from 4-bromo-3,5-diethylphenol and (3-formylphenyl)boronic acid. yield 68%. MS m/z 255 (M+H)⁺.

Reference Example 50

2',6'-diethyl-4'-[3-(methylsulfonyl)propoxy]biphenyl-3-carbaldehyde

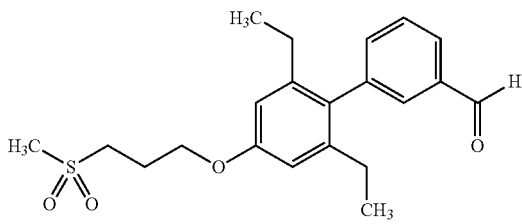 [SMILES: CCc1cc(OCCCS(C)(=O)=O)cc(CC)c1-c1cccc(C=O)c1]

To a solution of 2',6'-diethyl-4'-hydroxybiphenyl-3-carbaldehyde (2.44 g, 9.59 mmol) and 3-(methylsulfonyl)propyl 4-methylbenzenesulfonate (3.36 g, 11.5 mmol) in N,N-dimethylformamide (20 mL) was added potassium carbonate (1.73 g, 12.5 mmol), and the mixture was stirred at 90° C. for 70 hr under nitrogen atmosphere. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=30:70-70:30) to give the title compound (2.86 g, yield 80%) as a pale-yellow oil.
MS m/z 375 (M+H)⁺.

Reference Example 51

{2',6'-diethyl-4'-[3-(methylsulfonyl)propoxy]biphenyl-3-yl}methanol

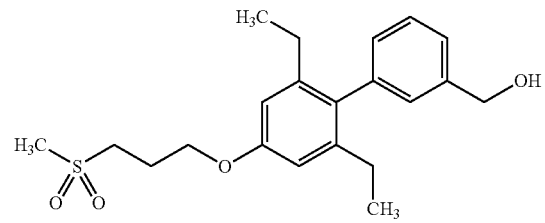 [SMILES: CCc1cc(OCCCS(C)(=O)=O)cc(CC)c1-c1cccc(CO)c1]

A solution of 2',6'-diethyl-4'-[3-(methylsulfonyl)propoxy]biphenyl-3-carbaldehyde (2.86 g, 7.64 mmol) in a mixed solvent of methanol (8 mL) and tetrahydrofuran (16 mL) was ice-cooled, sodium borohydride (90%, 0.161 g, 3.82 mmol) was added, and the mixture was stirred for 2 hr under nitrogen atmosphere. The reaction mixture was treated with 10% aqueous citric acid solution, and extracted with ethyl acetate. The extract was washed with saturated brine, dried over anhydrous magnesium sulfate, and concentrated under reduced pressure. The residue was purified by silica gel column chromatography (ethyl acetate:hexane=40:80-80:20), and the obtained crystals were recrystallized from heptane-ethyl acetate to give the title compound (2.41 g, yield 84%) as colorless crystals.
¹H NMR (CDCl₃) δ: 1.01 (6H, t, J=7.5 Hz), 1.66 (1H, t, J=5.9 Hz), 2.24-2.42 (6H, m), 2.97 (3H, s), 3.25-3.33 (2H, m), 4.16 (2H, t, J=5.7 Hz), 4.73 (2H, d, J=5.9 Hz), 6.67 (2H, s), 7.06-7.10 (1H, m), 7.12-7.16 (1H, m), 7.32-7.43 (2H, m).

Reference Example 52

{3',5'-dichloro-2',6'-diethyl-4'-[3-(methylsulfonyl)propoxy]biphenyl-3-yl}methanol

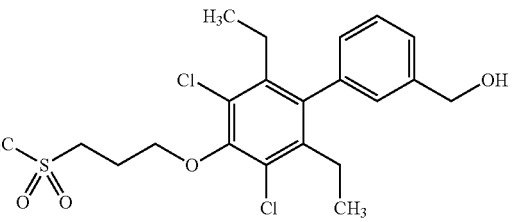

To a solution of {2',6'-diethyl-4'-[3-(methylsulfonyl)propoxy]biphenyl-3-yl}methanol (0.377 g, 1.00 mmol) in acetonitrile (5 mL) was added N-chlorosuccinimide (0.267 g, 2.00 mmol), and the mixture was stirred at room temperature for 3 days. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=15:85-50:50) to give the title compound (0.260 g, yield 58%) as a colorless oil.
¹H NMR (CDCl₃) δ: 0.94 (6H, t, J=7.4 Hz), 1.74 (1H, t, J=5.6 Hz), 2.36-2.48 (6H, m), 3.00 (3H, s), 3.44-3.53 (2H, m), 4.18 (2H, t, J=5.7 Hz), 4.75 (2H, d, J=5.6 Hz), 7.05-7.11 (1H, m), 7.14 (1H, s), 7.37-7.47 (2H, m).

Reference Example 53

3-bromo-4-phenoxybenzaldehyde

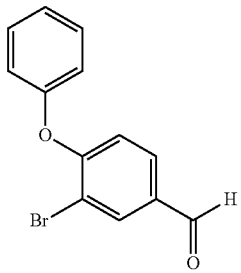 [SMILES: O=Cc1ccc(Oc2ccccc2)c(Br)c1]

To a solution of 3-bromo-4-fluorobenzaldehyde (2.03 g, 10.0 mmol) and phenol (0.941 g, 10.0 mmol) in N,N-dimethylformamide (10 mL) was added potassium carbonate (1.66 g, 12.0 mmol), and the mixture was stirred at 90° C. for 16 hr under nitrogen atmosphere. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=0:100-15:85) to give the title compound (2.27 g, yield 82%) as a pale-yellow oil.

$^1$H NMR (CDCl$_3$) δ: 6.90 (1H, d, J=8.5 Hz), 7.05-7.11 (2H, m), 7.21-7.29 (1H, m), 7.38-7.47 (2H, m), 7.72 (1H, dd, J=8.5, 2.1 Hz), 8.17 (1H, d, J=2.1 Hz), 9.89 (1H, s).

Reference Example 54

2-bromo-1,3-dimethyl-5-[3-(methylthio)propoxy]benzene

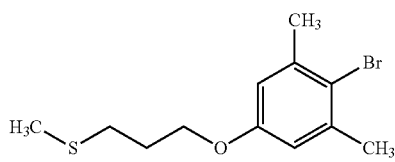

To a solution of 4-bromo-3,5-dimethylphenol (4.02 g, 20.0 mmol), 3-(methylthio)-1-propanol (2.12 g, 20.0 mmol) and tributylphosphine (7.97 mL, 32.0 mmol) in toluene (320 mL) was added 1,1'-(azodicarbonyl)dipiperidine (8.07 g, 32.0 mmol), and the mixture was stirred at room temperature for 18 hr under nitrogen atmosphere. Hexane (160 mL) was added to the reaction mixture, the insoluble substance was filtered off, and the filtrate was concentrated under reduced pressure. The residue was purified by silica gel column chromatography (ethyl acetate:hexane=0:100-25:75) to give the title compound (5.03 g, yield 87%) as a pale-yellow oil.

$^1$H NMR (CDCl$_3$) δ: 2.00-2.10 (2H, m), 2.12 (3H, s), 2.37 (6H, s), 2.67 (2H, t, J=7.1 Hz), 4.02 (2H, t, J=6.1 Hz), 6.65 (2H, s).

Reference Example 55

{2,6-dimethyl-4-[3-(methylthio)propoxy]phenyl}boronic acid

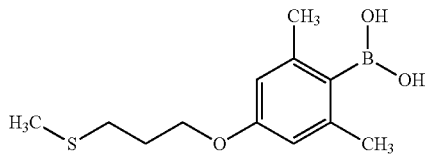

In the same manner as in Reference Example 2, the title compound was obtained as colorless crystals from 2-bromo-1,3-dimethyl-5-[3-(methylthio)propoxy]benzene. yield 87%.

$^1$H NMR (CDCl$_3$) δ: 2.00-2.10 (2H, m), 2.12 (3H, s), 2.36 (6H, s), 2.67 (2H, t, J=7.2 Hz), 4.04 (2H, t, J=6.1 Hz), 4.53 (2H, s), 6.55 (2H, s).

Reference Example 56

2',6'-dimethyl-4'-[3-(methylthio)propoxy]-6-phenoxybiphenyl-3-carbaldehyde

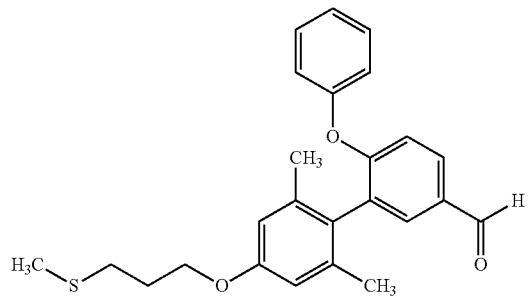 [SMILES: CSCCCOc1cc(C)c(-c2cc(C=O)ccc2Oc2ccccc2)c(C)c1]

3-Bromo-4-phenoxybenzaldehyde (1.11 g, 4.00 mmol), {2,6-dimethyl-4-[3-(methylthio)propoxy]phenyl}boronic acid (1.02 g, 4.00 mmol), 2-dicyclohexylphosphino-2',6'-dimethoxy-1,1'-biphenyl (0.263 g, 0.640 mmol) and tripotassium phosphate (1.70 g, 8.00 mmol) were dissolved in a mixed solvent of toluene (20 mL) and water (4 mL). After argon substitution, tris(dibenzylideneacetone)dipalladium (0) (0.147 g, 0.160 mmol) was added. The reaction mixture was stirred at 100° C. for 18 hr under argon atmosphere. The reaction mixture was allowed to cool, and water was added. The mixture was diluted with ethyl acetate, and the insoluble substance was filtered off through celite. The organic layer of the filtrate was washed with saturated brine, dried over anhydrous magnesium sulfate, and concentrated under reduced pressure. The residue was purified by silica gel column chromatography (ethyl acetate:hexane=0:100-20:80) to give the title compound (1.13 g, yield 70%) as a yellow oil.

MS m/z 407 (M+H)$^+$.

Reference Example 57

{2',6'-dimethyl-4'-[3-(methylthio)propoxy]-6-phenoxybiphenyl-3-yl}methanol

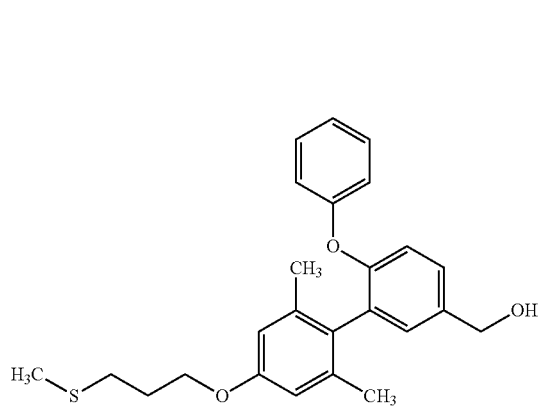 [SMILES: CSCCCOc1cc(C)c(-c2cc(CO)ccc2Oc2ccccc2)c(C)c1]

In the same manner as in Reference Example 41, the title compound was obtained as a colorless oil from 2',6'-dimethyl-4'-[3-(methylthio)propoxy]-6-phenoxybiphenyl-3-carbaldehyde.

yield 92%.

$^1$H NMR (CDCl$_3$) δ: 1.63 (1H, t, J=5.8 Hz), 2.00-2.10 (8H, m), 2.12 (3H, s), 2.68 (2H, t, J=7.2 Hz), 4.04 (2H, t, J=6.1 Hz), 4.69 (2H, d, J=5.8 Hz), 6.61 (2H, s), 6.82-6.89 (2H, m), 6.93-7.04 (2H, m), 7.14 (1H, d, J=2.1 Hz), 7.18-7.32 (3H, m).

Reference Example 58 methyl [(3S)-6-({2',6'-dimethyl-4'-[3-(methylthio)propoxy]-6-phenoxybiphenyl-3-yl}methoxy)-2,3-dihydro-1-benzofuran-3-yl]acetate In the same manner as in Reference Example 22, the title compound was obtained as a colorless oil from {2',6'-dimethyl-4'-[3-(methylthio)propoxy]-6-phenoxybiphenyl-3-yl}methanol and methyl [(3S)-6-hydroxy-2,3-dihydro-1-benzofuran-3-yl]acetate.

yield 71%.

MS m/z 599 (M+H)$^+$.

Reference Example 59

2-bromo-5-(methoxymethoxy)-1,3-dimethylbenzene

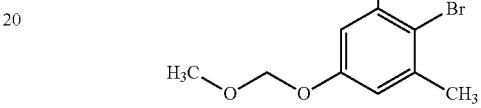

Under nitrogen atmosphere, hexane (50 mL) was added to sodium hydride (50% in oil, 12.6 g, 264 mmol). The mixture was stirred for 30 sec, and stood still, and the supernatant was removed. Tetrahydrofuran (460 mL) was added thereto, and the mixture was cooled to 0° C. A solution of 4-bromo-3,5-dimethylphenol (53.0 g, 264 mmol) in tetrahydrofuran (50 mL) was added slowly dropwise. After completion of the dropwise addition, and the mixture was stirred at 0° C. for 10 min, allowed to warm to room temperature, and was stirred for 20 min. Then, chloromethyl methyl ether (22.3 g, 277 mmol) was added slowly at room temperature, and the mixture was stirred for 24 hr. The reaction mixture was diluted with 1 M aqueous sodium hydroxide solution (80 mL). Tetrahydrofuran was evaporated under reduced pressure, and the residue was extracted with diethyl ether. The extract was washed successively with 2 M aqueous sodium hydroxide solution and saturated brine, dried over anhydrous magnesium sulfate, and concentrated under reduced pressure. The residue was purified by silica gel column chromatography (ethyl acetate:hexane=0:100-10:90) to give the title compound (47.6 g, yield 74%) as a colorless oil.

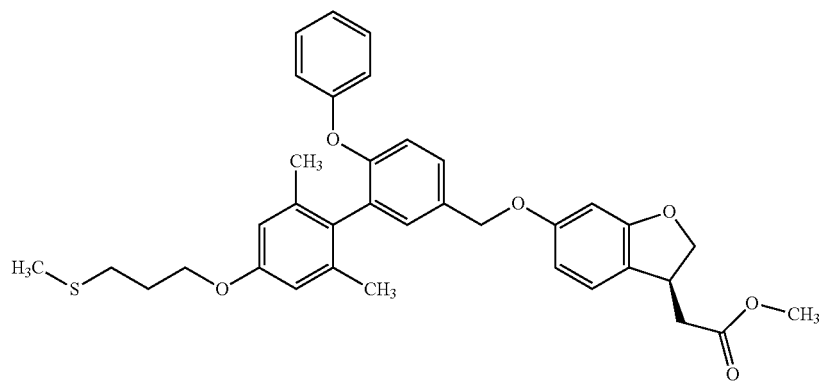

¹H NMR (CDCl₃) δ: 2.38 (6H, s), 3.47 (3H, s), 5.13 (2H, s), 6.79 (2H, s).

Reference Example 60

[4-(methoxymethoxy)-2,6-dimethylphenyl]boronic acid

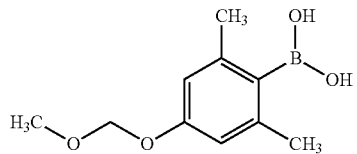

In the same manner as in Reference Example 2, the title compound was obtained as colorless crystals from 2-bromo-5-(methoxymethoxy)-1,3-dimethylbenzene. yield 91%.
¹H NMR (CDCl₃) δ: 2.36 (6H, s), 3.46 (3H, s), 4.65 (2H, s), 5.15 (2H, s), 6.68 (2H, s).

Reference Example 61 methyl 6-formyl-4'-(methoxymethoxy)-2',6'-dimethylbiphenyl-3-carboxylate

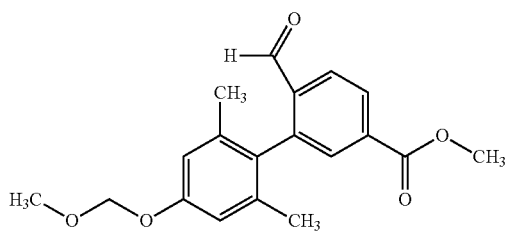

In the same manner as in Reference Example 56, the title compound was obtained as a yellow oil from [4-(methoxymethoxy)-2,6-dimethylphenyl]boronic acid and methyl 3-bromo-4-formylbenzoate. yield 79%.
¹H NMR (CDCl₃) δ: 1.94 (6H, s), 3.52 (3H, s), 3.95 (3H, s), 5.21 (2H, s), 6.84 (2H, s), 7.89-7.91 (1H, m), 8.06-8.10 (1H, m), 8.11-8.17 (1H, m), 9.73 (1H, d, J=0.8 Hz).

Reference Example 62 methyl 6-(hydroxymethyl)-4'-(methoxymethoxy)-2',6'-dimethylbiphenyl-3-carboxylate

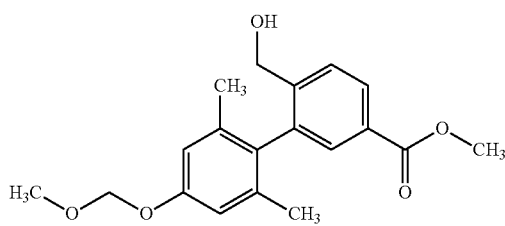

In the same manner as in Reference Example 41, the title compound was obtained as a colorless oil from methyl 6-formyl-4'-(methoxymethoxy)-2',6'-dimethylbiphenyl-3-carboxylate.
yield 93%.

¹H NMR (CDCl₃) δ: 1.58 (1H, t, J=5.9 Hz), 1.92 (6H, s), 3.52 (3H, s), 3.91 (3H, s), 4.38 (2H, d, J=5.9 Hz), 5.20 (2H, s), 6.81 (2H, s), 7.68 (1H, d, J=8.0 Hz), 7.73 (1H, d, J=1.7 Hz), 8.06 (1H, dd, J=8.0, 1.7 Hz).

Reference Example 63 methyl 4'-(methoxymethoxy)-2',6'-dimethyl-6-(phenoxymethyl)biphenyl-3-carboxylate

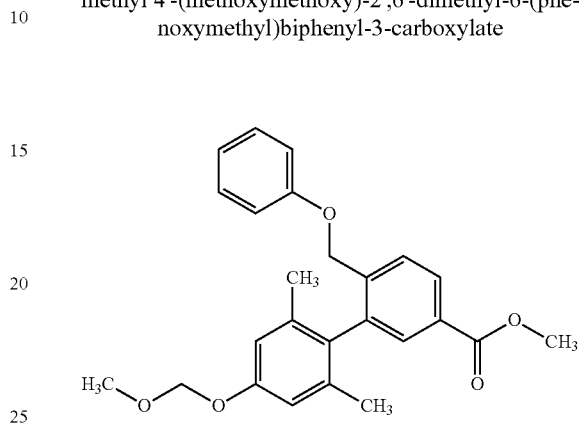

In the same manner as in Reference Example 22, the title compound was obtained as a colorless oil from methyl 6-(hydroxymethyl)-4'-(methoxymethoxy)-2',6'-dimethylbiphenyl-3-carboxylate and phenol. yield 96%.

MS m/z 407 (M+H)⁺.

Reference Example 64 methyl 4'-hydroxy-2',6'-dimethyl-6-(phenoxymethyl)biphenyl-3-carboxylate

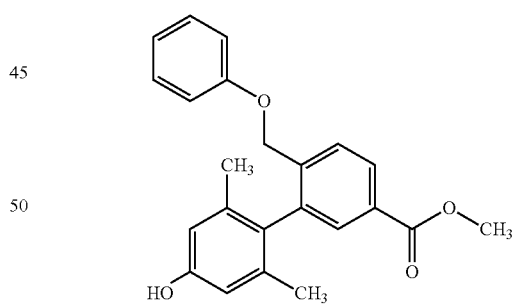

To a solution of methyl 4'-(methoxymethoxy)-2',6'-dimethyl-6-(phenoxymethyl)biphenyl-3-carboxylate (1.77 g, 4.35 mmol) in a mixed solvent of methanol (10 mL) and dimethoxyethane (5 mL) was added 10% hydrogen chloride-methanol solution (1 mL), and the mixture was stirred at 45° C. for 16 hr. The reaction mixture was concentrated under reduced pressure, and the residue was purified by silica gel column chromatography (ethyl acetate:hexane=10:90-25:75) to give the title compound (1.47 g, yield 93%) as a colorless amorphous powder.

MS m/z 363 (M+H)⁺.

Reference Example 65 methyl 2',6'-dimethyl-4'-[3-(methylsulfonyl)propoxy]-6-(phenoxymethyl)biphenyl-3-carboxylate

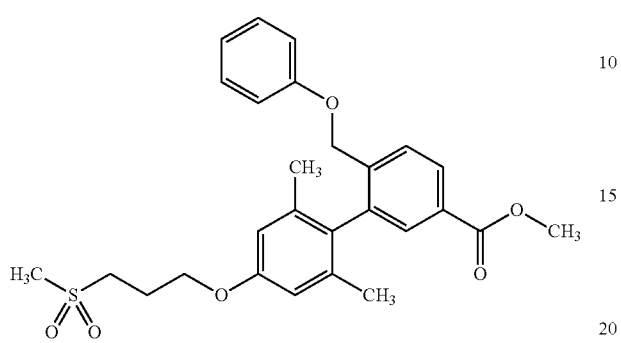

In the same manner as in Reference Example 18, the title compound was obtained as a colorless oil from methyl 4'-hydroxy-2',6'-dimethyl-6-(phenoxymethyl)biphenyl-3-carboxylate and 3-(methylsulfonyl)propyl 4-methylbenzenesulfonate. yield 92%.

$^1$H NMR (CDCl$_3$) δ: 1.95 (6H, s), 2.28-2.42 (2H, m), 2.96 (3H, s), 3.22-3.32 (2H, m), 3.91 (3H, s), 4.13 (2H, t, J=5.4 Hz), 4.68 (2H, s), 6.65 (2H, s), 6.77-6.85 (2H, m), 6.88-6.97 (1H, m), 7.17-7.28 (2H, m), 7.71-7.80 (2H, m), 8.07 (1H, dd, J=8.0, 1.9 Hz).

Reference Example 66

{2',6'-dimethyl-4'-[3-(methylsulfonyl)propoxy]-6-(phenoxymethyl)biphenyl-3-yl}methanol

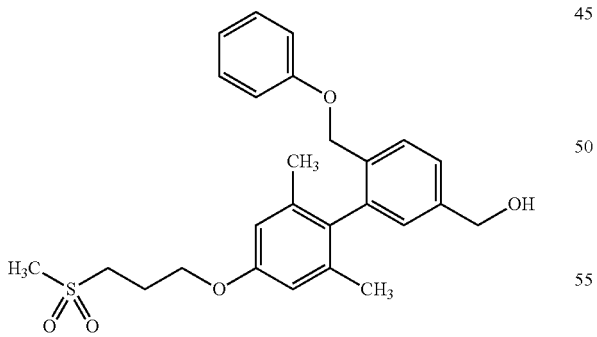

In the same manner as in Reference Example 5, the title compound was obtained as a colorless oil from methyl 2',6'-dimethyl-4'-[3-(methylsulfonyl)propoxy]-6-(phenoxymethyl) biphenyl-3-carboxylate. yield 100%.

$^1$H NMR (CDCl$_3$) δ: 1.72 (1H, t, J=6.0 Hz), 1.96 (6H, s), 2.29-2.41 (2H, m), 2.95 (3H, s), 3.23-3.31 (2H, m), 4.11 (2H, t, J=5.7 Hz), 4.64 (2H, s), 4.74 (2H, d, J=6.0 Hz), 6.63 (2H, s), 6.77-6.84 (2H, m), 6.88-6.96 (1H, m), 7.08 (1H, d, J=1.6 Hz), 7.18-7.26 (2H, m), 7.40 (1H, dd, J=7.9, 1.6 Hz), 7.64 (1H, d, J=7.9 Hz).

Reference Example 67

5-bromo-2-fluoro-4-hydroxybenzaldehyde

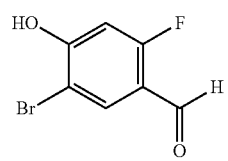 [SMILES: O=Cc1cc(Br)c(O)cc1F]

To a solution of 2-fluoro-4-hydroxybenzaldehyde (2.16 g, 15.4 mmol) in acetic acid (70 mL) was added a solution of bromine (2.71 g, 17.0 mmol) in acetic acid (10 mL), and the mixture was stirred at 45° C. for 26 hr. The reaction mixture was concentrated under reduced pressure, brine was added to the residue, and the mixture was extracted with ethyl acetate. The extract was dried over anhydrous magnesium sulfate, and concentrated under reduced pressure. The residue was purified by silica gel column chromatography (ethyl acetate:hexane=5:95-40:60) to give the title compound (2.74 g, yield 81%) as colorless crystals.

$^1$H NMR (CDCl$_3$) δ: 6.85 (1H, d, J=12.2 Hz), 7.94 (1H, d, J=7.5 Hz), 9.96 (1H, s), 12.08 (1H, br s).

Reference Example 68

4-(benzyloxy)-5-bromo-2-fluorobenzaldehyde

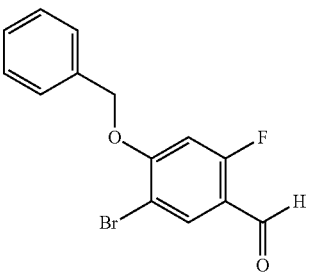 [SMILES: O=Cc1cc(Br)c(OCc2ccccc2)cc1F]

In the same manner as in Reference Example 18, the title compound was obtained as colorless crystals from 5-bromo-2-fluoro-4-hydroxybenzaldehyde and benzyl bromide. yield 85%.

¹H NMR (CDCl₃) δ: 5.35 (2H, s), 7.33-7.53 (6H, m), 8.01 (1H, d, J=7.5 Hz), 10.03 (1H, s).

Reference Example 69

6-(benzyloxy)-4-fluoro-2',6'-dimethyl-4'-[3-(methylthio)propoxy]biphenyl-3-carbaldehyde

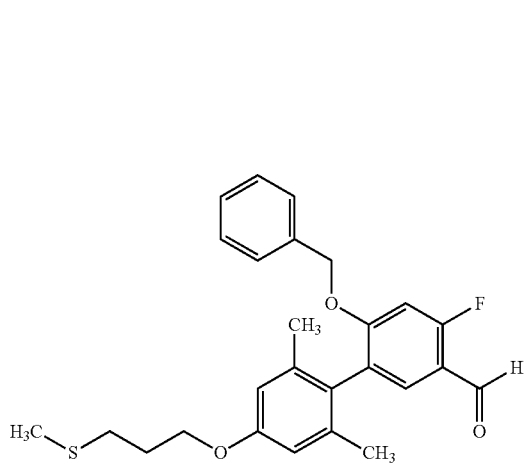 [SMILES: CSCCCOc1cc(C)c(-c2cc(C=O)c(F)cc2OCc2ccccc2)c(C)c1]

In the same manner as in Reference Example 56, the title compound was obtained as a yellow oil from 4-(benzyloxy)-5-bromo-2-fluorobenzaldehyde and {2,6-dimethyl-4-[3-(methylthio)propoxy]phenyl}boronic acid. yield 88%.

¹H NMR (CDCl₃) δ: 1.97 (6H, s), 2.06-2.12 (2H, m), 2.14 (3H, s), 2.71 (2H, t, J=7.2 Hz), 4.09 (2H, t, J=6.1 Hz), 5.12 (2H, s), 6.67 (2H, s), 6.74 (1H, d, J=12.4 Hz), 7.16-7.22 (2H, m), 7.27-7.36 (3H, m), 7.58 (1H, d, J=8.3 Hz), 10.23 (1H, s).

Reference Example 70

{6-(benzyloxy)-4-fluoro-2',6'-dimethyl-4'-[3-(methylthio)propoxy]biphenyl-3-yl}methanol

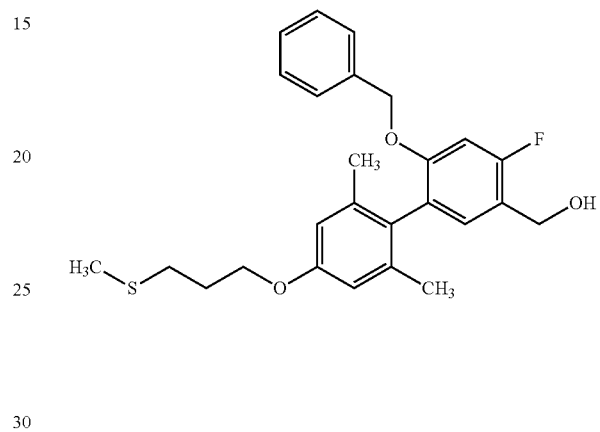

In the same manner as in Reference Example 41, the title compound was obtained as a colorless oil from 6-(benzyloxy)-4-fluoro-2',6'-dimethyl-4'-[3-(methylthio)propoxy]biphenyl-3-carbaldehyde. yield 89%.

¹H NMR (CDCl₃) δ: 1.68 (1H, t, J=5.9 Hz), 1.99 (6H, s), 2.03-2.14 (2H, m), 2.14 (3H, s), 2.71 (2H, t, J=7.2 Hz), 4.09 (2H, t, J=6.5 Hz), 4.69 (2H, d, J=5.9 Hz), 5.01 (2H, s), 6.67 (2H, s), 6.72 (1H, d, J=11.9 Hz), 7.05 (1H, d, J=8.7 Hz), 7.14-7.20 (2H, m), 7.20-7.34 (3H, m).

Reference Example 71 methyl [(3S)-6-({6-(benzyloxy)-4-fluoro-2',6'-dimethyl-4'-[3-(methylthio)propoxy]biphenyl-3-yl}methoxy)-2,3-dihydro-1-benzofuran-3-yl]acetate

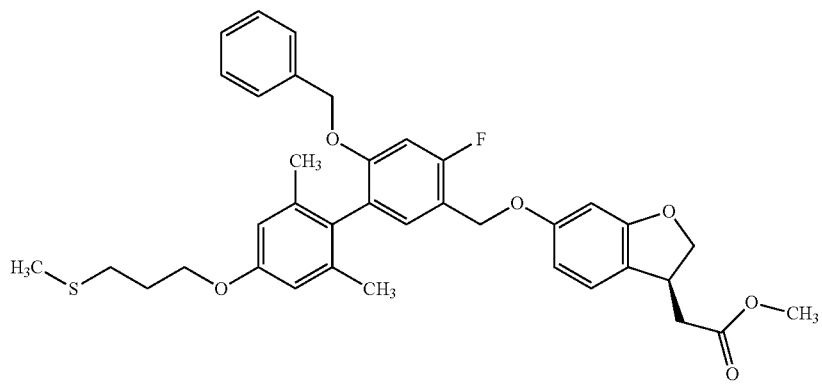

In the same manner as in Reference Example 22, the title compound was obtained as a colorless oil from {6-(benzyloxy)-4-fluoro-2',6'-dimethyl-4'-[3-(methylthio)propoxy]biphenyl-3-yl}methanol and methyl [(3S)-6-hydroxy-2,3-dihydro-1-benzofuran-3-yl]acetate. yield 80%.

$^1$H NMR (CDCl$_3$) δ: 1.97 (6H, s), 2.04-2.13 (2H, m), 2.14 (3H, s), 2.54 (1H, dd, J=16.5, 9.3 Hz), 2.66-2.79 (3H, m), 3.71 (3H, s), 3.73-3.85 (1H, m), 4.08 (2H, t, J=6.1 Hz), 4.25 (1H, dd, J=9.1, 6.1 Hz), 4.74 (1H, t, J=8.9 Hz), 5.02 (4H, s), 6.42-6.50 (2H, m), 6.66 (2H, s), 6.73 (1H, d, J=11.7 Hz), 7.00 (1H, d, J=7.9 Hz), 7.10 (1H, d, J=8.7 Hz), 7.14-7.34 (5H, m).

Example 1 methyl [(3S)-6-({4'-[(1,1-dioxidotetrahydro-2H-thiopyran-4-yl)oxy]-2',6'-dimethylbiphenyl-3-yl}methoxy)-2,3-dihydro-1-benzofuran-3-yl]acetate

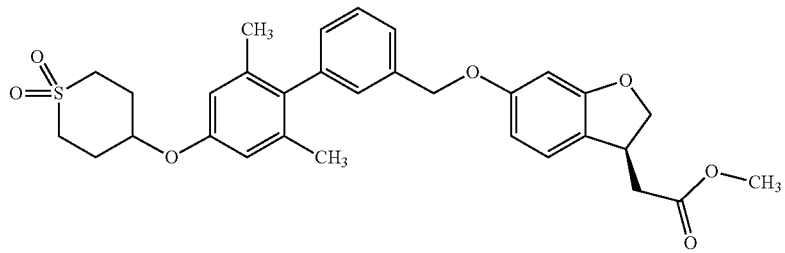 [SMILES: COC(=O)C[C@@H]1COc2cc(OCc3cccc(-c4c(C)cc(OC5CCS(=O)(=O)CC5)cc4C)c3)ccc21]

A solution of methyl [(3S)-6-hydroxy-2,3-dihydro-1-benzofuran-3-yl]acetate (0.208 g, 1.00 mmol), {4'-[(1,1-dioxidotetrahydro-2H-thiopyran-4-yl)oxy]-2',6'-dimethylbiphenyl-3-yl}methanol (0.360 g, 1.00 mmol) and tributylphosphine (0.324 g, 1.60 mmol) in toluene (15 mL) was stirred, 1,1'-(azodicarbonyl)dipiperidine (0.404 g, 1.60 mmol) was added, and the mixture was stirred at room temperature for 3 hr under nitrogen atmosphere. Hexane (8 mL) was added to the reaction mixture, the precipitated insoluble substance was filtered off, and the filtrate was concentrated under reduced pressure. The residue was purified by silica gel column chromatography (ethyl acetate:hexane=30:70-70:30) to give the title compound (0.432 g, yield 79%) as a colorless oil.

MS m/z 551 (M+H)$^+$.

Example 2

[(3S)-6-({4'-[(1,1-dioxidotetrahydro-2H-thiopyran-4-yl)oxy]-2',6'-dimethylbiphenyl-3-yl}methoxy)-2,3-dihydro-1-benzofuran-3-yl]acetic acid

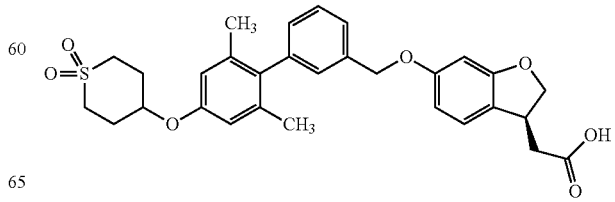

To a solution of methyl [(3S)-6-({4'-[(1,1-dioxidotetrahydro-2H-thiopyran-4-yl)oxy]-2',6'-dimethylbiphenyl-3-yl}methoxy)-2,3-dihydro-1-benzofuran-3-yl]acetate (0.427 g, 0.775 mmol) in a mixed solvent of methanol (2 mL) and tetrahydrofuran (4 mL) was added 2 M aqueous sodium hydroxide solution (1 mL), and the mixture was stirred at 50° C. for 2 hr. The reaction mixture was diluted with water, acidified with 1 M hydrochloric acid, and extracted with ethyl acetate. The extract was washed with saturated brine, dried over anhydrous magnesium sulfate, and concentrated under reduced pressure. The precipitated crystals were recrystallized from hexane-ethyl acetate to give the title compound (0.352 g, yield 85%) as colorless crystals.

MS m/z 537 (M+H)$^+$.

Example 3 methyl [6-({4'-[(4-hydroxy-1,1-dioxidotetrahydro-2H-thiopyran-4-yl)methoxy]-2',6'-dimethylbiphenyl-3-yl}methoxy)-2,3-dihydro-1-benzofuran-3-yl]acetate

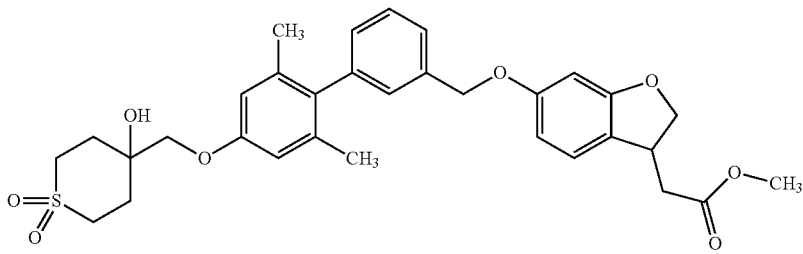 [SMILES: COC(=O)CC1COc2cc(OCc3cccc(-c4c(C)cc(OCC5(O)CCS(=O)(=O)CC5)cc4C)c3)ccc21]

To a solution of methyl [6-({4'-[(4-hydroxytetrahydro-2H-thiopyran-4-yl)methoxy]-2',6'-dimethylbiphenyl-3-yl}methoxy)-2,3-dihydro-1-benzofuran-3-yl]acetate (0.689 g, 1.26 mmol) in ethyl acetate (5 mL) was added m-chloroperbenzoic acid (72%, 0.602 g, 2.51 mmol), and the mixture was stirred at room temperature for 2 hr. The reaction mixture was diluted with ethyl acetate, washed successively with 1 M aqueous sodium hydroxide solution and saturated brine, dried over anhydrous magnesium sulfate, and concentrated under reduced pressure. The residue was purified by silica gel column chromatography (ethyl acetate:hexane=50:50-100:0), and the obtained crystals were recrystallized from hexane-ethyl acetate to give the title compound (0.416 g, yield 57%) as colorless crystals.

MS m/z 581 (M+H)$^+$.

Example 4

[6-({4'-[(4-hydroxy-1,1-dioxidotetrahydro-2H-thiopyran-4-yl)methoxy]-2',6'-dimethylbiphenyl-3-yl}methoxy)-2,3-dihydro-1-benzofuran-3-yl]acetic acid

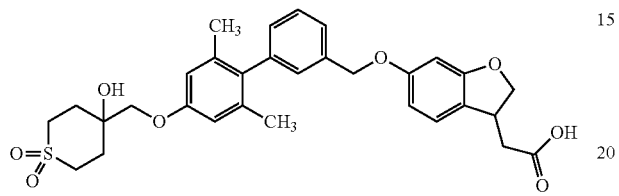

In the same manner as in Example 2, the title compound was obtained as colorless crystals from methyl [6-({4'-[(4-hydroxy-1,1-dioxidotetrahydro-2H-thiopyran-4-yl)methoxy]-2',6'-dimethylbiphenyl-3-yl}methoxy)-2,3-dihydro-1-benzofuran-3-yl]acetate. yield 89%.

MS m/z 567 (M+H)$^+$.

Example 5 methyl [(3S)-6-({4'-[(4-hydroxy-1,1-dioxidotetrahydro-2H-thiopyran-4-yl)methoxy]-2',6'-dimethylbiphenyl-3-yl}methoxy)-2,3-dihydro-1-benzofuran-3-yl]acetate

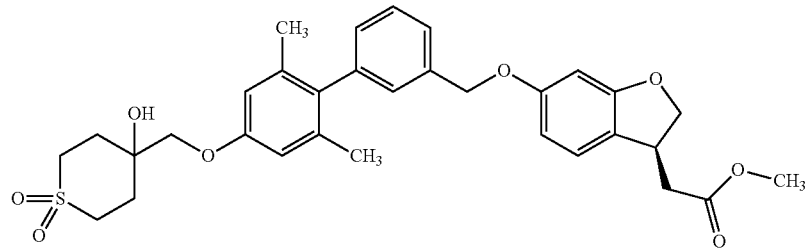 [SMILES: COC(=O)C[C@@H]1COc2cc(OCc3cccc(-c4c(C)cc(OCC5(O)CCS(=O)(=O)CC5)cc4C)c3)ccc21]

To a solution of methyl [(3S)-6-({4'-[(4-hydroxytetrahydro-2H-thiopyran-4-yl)methoxy]-2',6'-dimethylbiphenyl-3-yl}methoxy)-2,3-dihydro-1-benzofuran-3-yl]acetate (1.43 g, 2.61 mmol) in ethyl acetate (15 mL) was added m-chloroperbenzoic acid (65%, 1.39 g, 5.22 mmol) under ice-cooling, and the mixture was stirred at the same temperature for 2 hr. The reaction mixture was diluted with ethyl acetate, washed successively with aqueous sodium thiosulfate solution, 1 M aqueous sodium hydroxide solution and saturated brine, dried over anhydrous magnesium sulfate, and concentrated under reduced pressure. The residue was purified by silica gel column chromatography (ethyl acetate:hexane=40:60-80:20), and the obtained crystals were recrystallized from heptane-ethyl acetate to give the title compound (1.20 g, yield 79%) as colorless crystals.

MS m/z 581 (M+H)$^+$.

Example 6

[(3S)-6-({4'-[(4-hydroxy-1,1-dioxidotetrahydro-2H-thiopyran-4-yl)methoxy]-2',6'-dimethylbiphenyl-3-yl}methoxy)-2,3-dihydro-1-benzofuran-3-yl]acetic acid To a solution of methyl [(3S)-6-({4'-[(4-hydroxy-1,1-dioxidotetrahydro-2H-thiopyran-4-yl)methoxy]-2',6'-dimethylbiphenyl-3-yl}methoxy)-2,3-dihydro-1-benzofuran-3-yl]acetate (0.482 g, 0.830 mmol) in a mixed solvent of methanol (2 mL) and tetrahydrofuran (4 mL) was added 2 M aqueous sodium hydroxide solution (1 mL), and the mixture was stirred at 50° C. for 2 hr. The reaction mixture was diluted with water, acidified with 1 M hydrochloric acid, and extracted with ethyl acetate. The extract was washed with saturated brine, dried over anhydrous magnesium sulfate, and concentrated under reduced pressure. The precipitated crystals were recrystallized from heptane-ethyl acetate to give the title compound (0.358 g, yield 76%) as colorless crystals.

MS m/z 567 (M+H)$^+$.

Elemental analysis for $C_{31}H_{34}O_8S$
Calculated: C, 65.71; H, 6.05.
Found: C, 65.69; H, 6.03.

Example 7 methyl [(3S)-6-({2',3',5',6'-tetramethyl-4'-[3-(methylsulfonyl)propoxy]biphenyl-3-yl}methoxy)-2,3-dihydro-1-benzofuran-3-yl]acetate

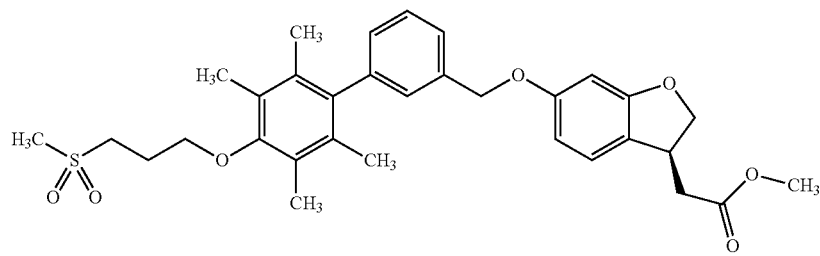

A solution of methyl [(3S)-6-hydroxy-2,3-dihydro-1-benzofuran-3-yl]acetate (0.208 g, 1.00 mmol), {2',3',5',6'-tetramethyl-4'-[3-(methylsulfonyl)propoxy]biphenyl-3-yl}methanol (0.377 g, 1.00 mmol) and tributylphosphine (0.324 g, 1.60 mmol) in toluene (15 mL) was stirred, 1,1'-(azodicarbonyl)dipiperidine (0.404 g, 1.60 mmol) was added, and the mixture was stirred at room temperature for 1.5 hr under nitrogen atmosphere. Hexane (8 mL) was added to the reaction mixture, the precipitated insoluble substance was filtered off, and the filtrate was concentrated under reduced pressure. The residue was purified by silica gel column chromatography (ethyl acetate:hexane=30:70-80:20) to give the title compound (0.462 g, yield 82%) as a colorless oil.
MS m/z 567 (M+H)$^+$.

Example 8

[(3S)-6-({2',3',5',6'-tetrameramethyl-4'-[3-(methylsulfonyl)propoxy]biphenyl-3-yl}methoxy)-2,3-dihydro-1-benzofuran-3-yl]acetic acid

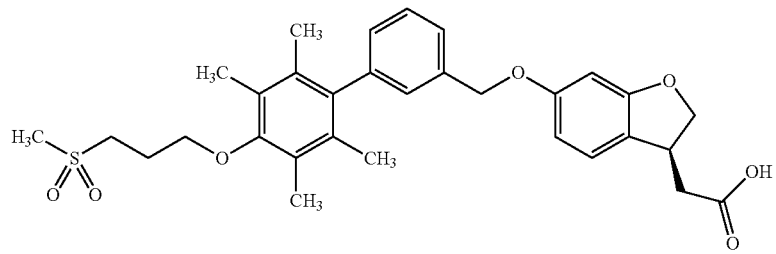 [SMILES: Cc1c(C)c(-c2cccc(COc3ccc4c(c3)OC[C@H]4CC(=O)O)c2)c(C)c(C)c1OCCCS(C)(=O)=O]

To a solution of methyl [(3S)-6-({2',3',5',6'-tetramethyl-4'-[3-(methylsulfonyl)propoxy]biphenyl-3-yl}methoxy)-2,3-dihydro-1-benzofuran-3-yl]acetate (0.457 g, 0.806 mmol) in a mixed solvent of methanol (2 mL) and tetrahydrofuran (4 mL) was added 2 M aqueous sodium hydroxide solution (1 mL), and the mixture was stirred at 50° C. for 2 hr. The reaction mixture was diluted with water, acidified with 1 M hydrochloric acid, and extracted with ethyl acetate. The extract was washed with saturated brine, dried over anhydrous magnesium sulfate, and concentrated under reduced pressure. The precipitated crystals were recrystallized from heptane-ethyl acetate to give the title compound (0.417 g, yield 94%) as colorless crystals.
MS m/z 553 (M+H)$^+$.

Example 9 methyl [(3S)-6-({2',6'-dimethyl-4'-[3-(methylsulfonyl)propoxy]biphenyl-3-yl}methoxy)-2,3-dihydro-1-benzofuran-3-yl]acetate

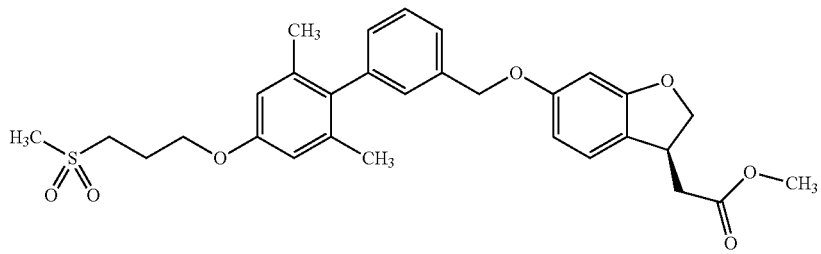

A solution of methyl [(3S)-6-hydroxy-2,3-dihydro-1-benzofuran-3-yl]acetate (0.208 g, 1.00 mmol), {2',6'-dimethyl-4'-[3-(methylsulfonyl)propoxy]biphenyl-3-yl}methanol (0.348 g, 1.00 mmol) and tributylphosphine (0.324 g, 1.60 mmol) in toluene (15 mL) was stirred, 1,1'-(azodicarbonyl)dipiperidine (0.404 g, 1.60 mmol) was added, and the mixture was stirred at room temperature for 1.5 hr under nitrogen atmosphere. Hexane (8 mL) was added to the reaction mixture, the precipitated insoluble substance was filtered off, and the filtrate was concentrated under reduced pressure. The residue was purified by silica gel column chromatography (ethyl acetate:hexane=40:60-80:20) to give the title compound (0.442 g, yield 82%) as a colorless oil.

MS m/z 539 (M+H)$^+$.

Example 10

[(3S)-6-({2',6'-dimethyl-4'-[3-(methylsulfonyl)propoxy]biphenyl-3-yl}methoxy)-2,3-dihydro-1-benzofuran-3-yl]acetic acid

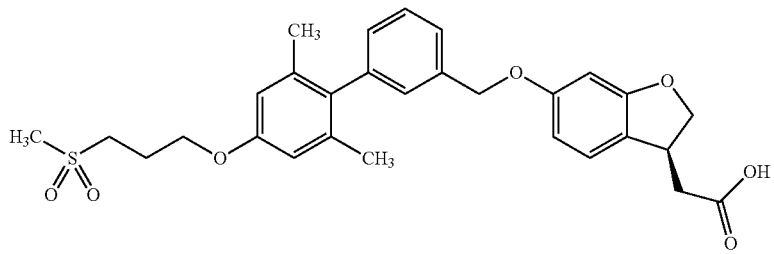 [SMILES: Cc1cc(OCCCS(C)(=O)=O)cc(C)c1-c1cccc(COc2ccc3c(c2)OC[C@H]3CC(=O)O)c1]

To a solution of methyl [(3S)-6-({2',6'-dimethyl-4'-[3-(methylsulfonyl)propoxy]biphenyl-3-yl}methoxy)-2,3-dihydro-1-benzofuran-3-yl]acetate (0.438 g, 0.813 mmol) in a mixed solvent of methanol (2 mL) and tetrahydrofuran (4 mL) was added 2 M aqueous sodium hydroxide solution (1 mL), and the mixture was stirred at 50° C. for 2 hr. The reaction mixture was diluted with water, acidified with 1 M hydrochloric acid, and extracted with ethyl acetate. The extract was washed with saturated brine, dried over anhydrous magnesium sulfate, and concentrated under reduced pressure. The precipitated crystals were recrystallized from heptane-ethyl acetate to give the title compound (0.377 g, yield 88%) as colorless crystals.

MS m/z 525 (M+H)$^+$.

Elemental analysis for $C_{29}H_{32}O_7S$

Calculated: C, 66.39; H, 6.15.

Found: C, 66.23; H, 6.14.

Example 11

[(3S)-6-({4'-[2-(ethylsulfonyl)ethoxy]-2',6'-dimethylbiphenyl-3-yl}methoxy)-2,3-dihydro-1-benzofuran-3-yl]acetic acid

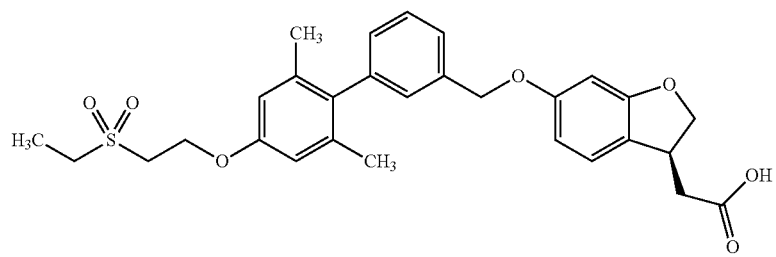 [SMILES: CCS(=O)(=O)CCOc1cc(C)c(-c2cccc(COc3ccc4c(c3)OC[C@H]4CC(=O)O)c2)c(C)c1]

To a solution of [(3S)-6-({4'-[2-(ethylthio)ethoxy]-2',6'-dimethylbiphenyl-3-yl-3-yl}methoxy)-2,3-dihydro-1-benzofuran-3-yl]acetic acid (0.304 g, 0.617 mmol) in methanol (10 mL) was added dropwise a solution of potassium peroxysulfate (trade name: OXONE, 0.569 g, 0.926 mmol) in water (5 mL) under ice-cooling, and the mixture was stirred for 12 hr, during which the mixture was allowed to gradually warm to room temperature. The reaction mixture was diluted with water, and extracted with ethyl acetate. The extract was washed with saturated brine, dried over anhydrous magnesium sulfate, and concentrated under reduced pressure. The residue was purified by preparative HPLC, and the obtained crystals were recrystallized from heptane-ethyl acetate to give the title compound (0.237 g, yield 73%) as colorless crystals.

MS m/z 525 (M+H)$^+$.

Example 12 methyl [(3S)-6-({3'-fluoro-2',6'-dimethyl-4'-[3-(methylsulfonyl)propoxy]biphenyl-3-yl}methoxy)-2,3-dihydro-1-benzofuran-3-yl]acetate

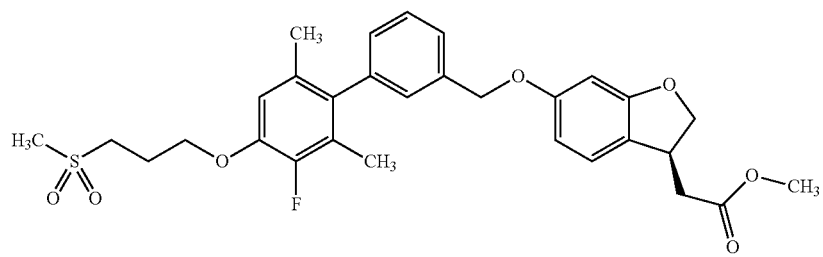

A solution of methyl [(3S)-6-hydroxy-2,3-dihydro-1-benzofuran-3-yl]acetate (0.729 g, 3.50 mmol), {3'-fluoro-2',6'-dimethyl-4'-[3-(methylsulfonyl)propoxy]biphenyl-3-yl}methanol (1.28 g, 3.50 mmol) and tributylphosphine (1.13 g, 5.60 mmol) in a mixed solvent of toluene (45 mL) and tetrahydrofuran (5 mL) was stirred, 1,1'-(azodicarbonyl)dipiperidine (1.41 g, 5.60 mmol) was added, and the mixture was stirred at room temperature for 4 hr under nitrogen atmosphere. Hexane (50 mL) was added to the reaction mixture, the precipitated insoluble substance was filtered off, and the filtrate was concentrated under reduced pressure. The residue was purified by silica gel column chromatography (ethyl acetate:hexane=40:60-80:20) and basic silica gel column chromatography (ethyl acetate:hexane=40:60-100:0), and the obtained crystals were recrystallized from heptane-ethyl acetate to give the title compound (1.50 g, yield 77%) as colorless crystals.

MS m/z 557 (M+H)$^+$.

Example 13

[(3S)-6-({3'-fluoro-2',6'-dimethyl-4'-[3-(methylsulfonyl)propoxy]biphenyl-3-yl}methoxy)-2,3-dihydro-1-benzofuran-3-yl]acetic acid

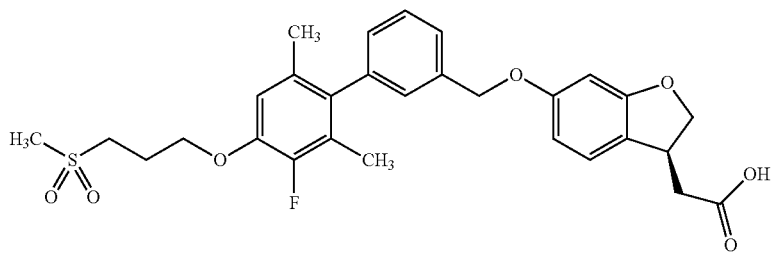

To a solution of methyl [(3S)-6-({3'-fluoro-2',6'-dimethyl-4'-[3-(methylsulfonyl)propoxy]biphenyl-3-yl}methoxy)-2,3-dihydro-1-benzofuran-3-yl]acetate (0.418 g, 0.740 mmol) in a mixed solvent of methanol (4 mL) and tetrahydrofuran (8 mL) was added 2 M aqueous sodium hydroxide solution (2 mL), and the mixture was stirred at 50° C. for 2 hr. The reaction mixture was diluted with water, acidified with 1 M hydrochloric acid, and extracted with ethyl acetate. The extract was washed with saturated brine, dried over anhydrous magnesium sulfate, and concentrated under reduced pressure. The residue was purified by silica gel column chromatography (ethyl acetate:hexane=50:50-100:0), and the obtained crystals were recrystallized from hexane-ethyl acetate to give the title compound (0.248 g, yield 62%) as colorless crystals.

MS m/z 543 (M+H)$^+$.
Elemental analysis for $C_{29}H_{31}FO_7S$
Calculated: C, 64.19; H, 5.76.
Found: C, 64.40; H, 5.92.

Example 14 optically active form of methyl (6-hydroxy-2,3-dihydro-1-benzofuran-3-yl)acetate

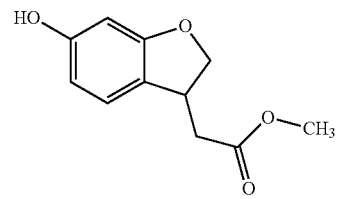

To a mixture of (1,5-cyclooctadiene)rhodium trifluoromethanesulfonate (12 mg) and (R,R)-Me-BPE (6.5 mg) was added methanol (2.5 mL) sufficiently substituted with argon gas, and the mixture was stirred at room temperature for 15 min. This was added to methyl (6-hydroxy-1-benzofuran-3-yl)acetate (51 mg), and the mixture was stirred at 70° C. for 3 hr under 0.7 MPa hydrogen atmosphere. The reaction mixture was quantified by HPLC. As a result, the enantiomeric excess was 47.9%, and the yield was 41.5%.

(conditions of high performance liquid chromatography) column: CHIRALPAK AS (manufactured by DAICEL CHEMICAL INDUSTRIES LTD.)
mobile phase: n-hexane/2-propanol (volume ratio: 85/15)
flow rate: 0.75 mL/min
detection: UV (220 nm)
temperature: room temperature
retention time: 15 min (74.0%), 19 min (26.0%)

Example 15 optically active form of methyl (6-methoxy-2,3-dihydro-1-benzofuran-3-yl)acetate

To a mixture of (1,5-cyclooctadiene)rhodium trifluoromethanesulfonate (12 mg) and (R,R)-Me-BPE (6.5 mg) was added methanol (2.5 mL) sufficiently substituted by argon gas, and the mixture was stirred at room temperature for 15 min. This was added to methyl (6-methoxy-1-benzofuran-3-yl)acetate (55 mg), and the mixture was stirred at 70° C. for 3 hr under 0.7 MPa hydrogen atmosphere. The reaction mixture was quantified by HPLC. As a result, the enantiomeric excess was 52.8%, and the yield was 24.3%.

(conditions of high performance liquid chromatography) column: CHIRALPAK AD-RH (manufactured by DAICEL CHEMICAL INDUSTRIES LTD.)

mobile phase: acetonitrile/water (volume ratio: 40/60)

flow rate: 1.0 mL/min detection: UV (220 nm)

temperature: room temperature retention time: 19 min (76.4%), 25 min (23.6%)

Example 16 optically active form of (6-methoxy-2,3-dihydro-1-benzofuran-3-yl)acetic acid

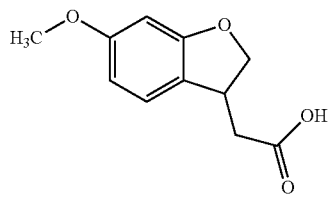

To a mixture of (1,5-cyclooctadiene)rhodium trifluoromethanesulfonate (5.9 mg) and (S,S)-Et-FerroTANE (5.5 mg) was added methanol (2.5 mL) sufficiently substituted by argon gas, and the mixture was stirred at room temperature for 15 min. This was added to a mixture of (6-methoxy-1-benzofuran-3-yl)acetic acid (51.5 mg) and sodium methoxide (7 mg), and the mixture was stirred at room temperature for 5 hr under 0.7 MPa hydrogen atmosphere. The reaction mixture was quantified by HPLC. As a result, the enantiomeric excess was 86.2%, and the yield was 88.4%.

(conditions of high performance liquid chromatography)

column: CHIRALPAK AS-H (manufactured by DAICEL CHEMICAL INDUSTRIES LTD.)

mobile phase: n-hexane/2-propanol/trifluoroacetate (volume ratio: 95/5/0.1)

flow rate: 1.0 mL/min detection: UV (220 nm)

temperature: room temperature retention time: 22 min (93.1%), 24 min (6.9%)

Example 17 optically active form of (6-hydroxy-2,3-dihydro-1-benzofuran-3-yl)acetic acid

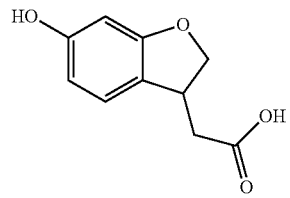 [SMILES: O=C(O)CC1COc2cc(O)ccc21]

To a mixture of (1,5-cyclooctadiene)rhodium trifluoromethanesulfonate (47 mg) and (S,S)-Et-FerroTANE (44 mg) was added methanol (15 mL) sufficiently substituted by argon gas, and the mixture was stirred at room temperature 15 min. To a mixture of (6-hydroxy-1-benzofuran-3-yl)carboxylic acid (1.92 g) and sodium methoxide (270 mg) was added methanol (35 mL) sufficiently substituted by argon gas. The methanol solution prepared earlier was added thereto, and the mixture was stirred at room temperature for 2 hr under 0.7 MPa hydrogen atmosphere. The reaction mixture was quantified by HPLC. As a result, the enantiomeric excess was 91.2%, and the yield was 98.5%.

(conditions of high performance liquid chromatography) column: CHIRALPAK AD-H (manufactured by DAICEL CHEMICAL INDUSTRIES LTD.)

mobile phase: n-hexane/ethanol/trifluoroacetate (volume ratio: 90/10/0.1)

flow rate: 1.0 mL/min detection: UV (220 nm)

temperature: room temperature retention time: 27 min (4.4%), 29 min (95.6%)

The reaction mixture was neutralized, and concentrated under reduced pressure. The residue was partitioned between water and ethyl acetate. The organic layer was washed with saturated brine, dried over anhydrous sodium sulfate, naturally filtered, and concentrated under reduced pressure. The obtained residue was purified by silica gel chromatography to give colorless crystals (1.56 g). yield 80.5%, enantiomeric excess 90.3%.

$^1$H-NMR (400 MHz, tetrahydrofuran-d$_6$) δ: 2.43 (1H, dd, J=16, 11 Hz), 2.67 (1H, dd, J=16, 11 Hz), 3.67 (1H, m), 4.15

(1H, dd, J=9 Hz) 4.64 (1H, t-like, J=9 Hz), 6.13 (1H, d, J=2 Hz), 6.20 (1H, dd, J=8, 2 Hz), 6.93 (1H, d, J=8 Hz) 8.03 (1H, br s), 10.9 (1H, s).

Example 18 methyl [(3S)-6-hydroxy-2,3-dihydro-1-benzofuran-3-yl]acetate

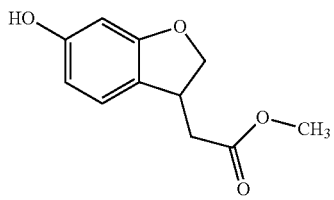

To a mixture of (1,5-cyclooctadiene)rhodium trifluoromethanesulfonate (656 mg) and (S,S)-Et-FerroTANE (620 mg) was added methanol (200 mL) sufficiently substituted by argon gas, and the mixture was stirred at room temperature 15 min. To a mixture of (6-hydroxy-1-benzofuran-3-yl)acetate (26.1 g) and sodium methoxide (3.8 g) was added methanol (500 mL) sufficiently substituted by argon gas. The methanol solution prepared earlier was added thereto, and the mixture was stirred at room temperature for 2 hr under 0.7 MPa hydrogen atmosphere. The reaction mixture was quantified by HPLC. As a result, the enantiomeric excess was 90.8%, the yield was quantitative.
(conditions of high performance liquid chromatography) column: CHIRALPAK AD-H (manufactured by DAICEL CHEMICAL INDUSTRIES LTD.)
mobile phase: n-hexane/ethanol/trifluoroacetate (volume ratio: 90/10/0.1)
flow rate: 1.0 mL/min
detection: UV (220 nm)
temperature: room temperature
retention time: 27 min (4.6%), 29 min (95.4%)

The reaction mixture was concentrated under reduced pressure, and the residue was partitioned between diluted hydrochloric acid and ethyl acetate. The organic layer was washed with saturated brine, dried over anhydrous sodium sulfate, naturally filtered, and concentrated under reduced pressure. The residue was suspended in methanol (200 mL), concentrated sulfuric acid (14.9 mL) was added at 0° C., and the mixture was heated under reflux for 1.5 hr. The reaction mixture was concentrated under reduced pressure, ice water was added, and the mixture was extracted with ethyl acetate. The extract was washed successively with saturated aqueous sodium hydrogencarbonate and saturated brine, dried over anhydrous magnesium sulfate, and concentrated under reduced pressure. The residue was purified by silica gel column chromatography (ethyl acetate) to give the title compound (26.3 g, yield 93%) as a pale-brown solid. This product was purified by the following conditions of high performance liquid chromatography to give the title compound (24.4 g, enantiomeric excess 99.6%, yield 93%).
(conditions of high performance liquid chromatography) column: CHIRALPAK AD (manufactured by DAICEL CHEMICAL INDUSTRIES LTD.)
mobile phase: n-hexane/2-propanol (volume ratio: 88/12)
flow rate: 60 mL/min
detection: UV (220 nm)
temperature: 30° C.

Example 19

[(3S)-6-({2'-(hydroxymethyl)-6'-methyl-4'-[3-(methylsulfonyl)propoxy]biphenyl-3-yl}methoxy)-2,3-dihydro-1-benzofuran-3-yl]acetic acid

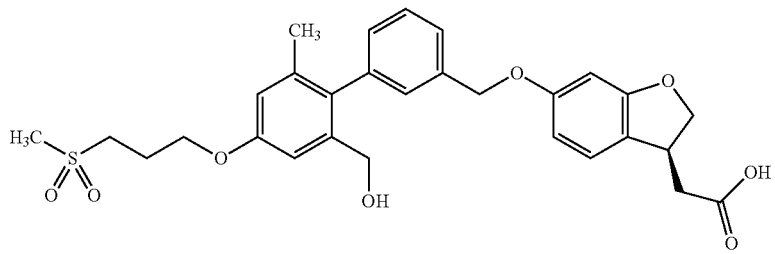 [SMILES: Cc1cc(OCCCS(C)(=O)=O)cc(CO)c1-c1cccc(COc2ccc3c(c2)OC[C@H]3CC(=O)O)c1]

To a solution of methyl [(3S)-6-({2'-(acetoxymethyl)-6'-methyl-4'-[3-(methylsulfonyl)propoxy]biphenyl-3-yl}methoxy)-2,3-dihydro-1-benzofuran-3-yl]acetate (1.11 g, 1.86 mmol) in a mixed solvent of methanol (4 mL) and tetrahydrofuran (8 mL) was added 2 M aqueous sodium hydroxide solution (2 mL), and the mixture was stirred at 50° C. for 2 hr. The reaction mixture was diluted with water, acidified with 1 M hydrochloric acid, and extracted with ethyl acetate. The extract was washed with saturated brine, dried over anhydrous magnesium sulfate, and concentrated under reduced pressure. The residue was purified by silica gel column chromatography (ethyl acetate:hexane=50:50-100:0) and preparative HPLC, and the obtained crystals were recrystallized from heptane-ethyl acetate to give the title compound (0.508 g, yield 51%) as colorless crystals.

$^1$H NMR (CDCl$_3$) δ: 2.00 (3H, s), 2.30-2.41 (2H, m), 2.55-2.67 (1H, m), 2.72-2.81 (1H, m), 2.96 (3H, s), 3.23-3.31 (2H, m), 3.73-3.85 (1H, m), 4.16 (2H, t, J=5.9 Hz), 4.25-4.34 (3H, m), 4.69-4.78 (1H, m), 5.08 (2H, s), 6.40-6.50 (2H, m) 6.74 (1H, d, J=2.7 Hz), 6.93 (1H, d, J=2.7 Hz), 7.00-7.10 (2H, m), 7.16 (1H, s), 7.36-7.46 (2H, m). ,

Example 20

[(3S)-6-({2',6'-dimethyl-4'-[3-(methylsulfonyl)propoxy]biphenyl-3-yl}methoxy)-2,3-dihydro-1-benzofuran-3-yl]acetic acid 0.5 hydrate

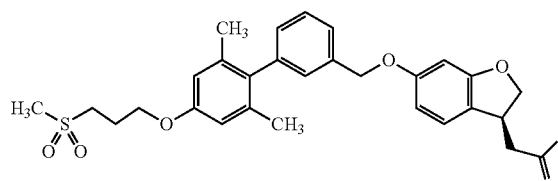

[(3S)-6-({2',6'-Dimethyl-4'-[3-(methylsulfonyl)propoxy]biphenyl-3-yl}methoxy)-2,3-dihydro-1-benzofuran-3-yl]acetic acid was recrystallized from ethanol-water to give the title compound as colorless crystals. yield 85%.

$^1$H NMR (CDCl$_3$) δ: 1.99 (6H, s), 2.29-2.41 (2H, m), 2.61 (1H, dd, J=16.9, 9.2 Hz), 2.81 (1H, dd, J=16.9, 5.5 Hz), 2.97 (3H, s), 3.23-3.31 (2H, m), 3.75-3.87 (1H, m), 4.13 (2H, t, J=5.8 Hz), 4.28 (1H, dd, J=9.1, 6.0 Hz), 4.76 (1H, t, J=9.1 Hz), 5.06 (2H, s), 6.44-6.52 (2H, m), 6.64 (2H, s), 7.02-7.10 (2H, m), 7.16 (1H, s), 7.35-7.46 (2H, m).

Example 21 methyl [(3S)-6-({3'-chloro-2',6'-dimethyl-4'-[3-(methylsulfonyl)propoxy]biphenyl-3-yl}methoxy)-2,3-dihydro-1-benzofuran-3-yl]acetate

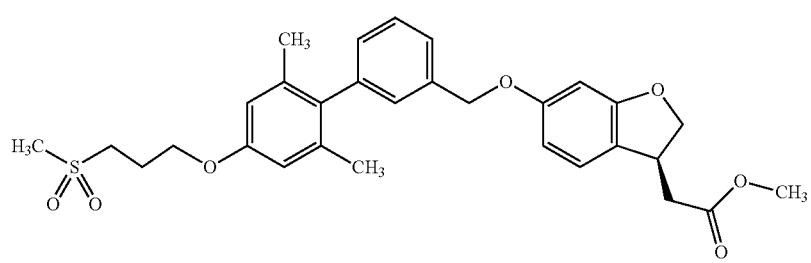

In the same manner as in Reference Example 18, the title compound was obtained as a colorless viscous oil from methyl {(3S)-6-[(3'-chloro-4'-hydroxy-2',6'-dimethylbiphenyl-3-yl)methoxy]-2,3-dihydro-1-benzofuran-3-yl}acetate and 3-(methylsulfonyl)propyl 4-methylbenzenesulfonate. yield 88%.

MS m/z 573 (M+H)$^+$.

Example 22

[(3S)-6-({3'-chloro-2',6'-dimethyl-4'-[3-(methylsulfonyl)propoxy]biphenyl-3-yl}methoxy)-2,3-dihydro-1-benzofuran-3-yl]acetic acid

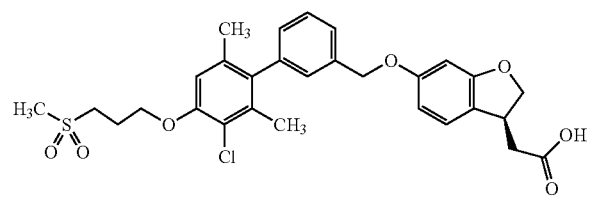 [SMILES: Cc1cc(OCCCS(C)(=O)=O)c(Cl)c(C)c1-c1cccc(COc2ccc3c(c2)OC[C@H]3CC(=O)O)c1]

To a solution of methyl [(3S)-6-({3'-chloro-2',6'-dimethyl-4'-[3-(methylsulfonyl)propoxy]biphenyl-3-yl}methoxy)-2,3-dihydro-1-benzofuran-3-yl]acetate (0.676 g, 1.18 mmol) in a mixed solvent of methanol (2 mL) and tetrahydrofuran (4 mL) was added 2 M aqueous sodium hydroxide solution (1.2 mL), and the mixture was stirred at 50° C. for 2 hr. The reaction mixture was diluted with water, acidified with 1 M hydrochloric acid, and extracted with ethyl acetate. The extract was washed with saturated brine, dried over anhydrous magnesium sulfate, and concentrated under reduced pressure. The precipitated crystals were recrystallized from diethyl ether-ethyl acetate to give the title compound (0.418 g, yield 63%) as colorless crystals.

MS m/z 559 (M+H)$^+$.

Elemental analysis for $C_{29}H_{31}ClO_7S$

Calculated: C, 62.30; H, 5.59.
Found: C, 62.03; H, 5.58.

Example 23 methyl [(3S)-6-({3',5'-dichloro-2',6'-dimethyl-4'-[3-(methylsulfonyl)propoxy]biphenyl-3-yl}methoxy)-2,3-dihydro-1-benzofuran-3-yl]acetate

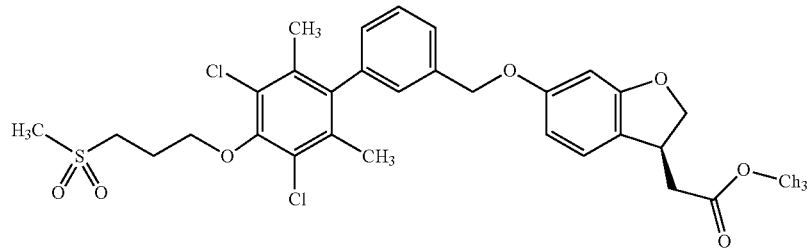

A solution of methyl [(3S)-6-hydroxy-2,3-dihydro-1-benzofuran-3-yl]acetate (0.237 g, 1.14 mmol), {3',5'-dichloro-2',6'-dimethyl-4'-[3-(methylsulfonyl)propoxy]biphenyl-3-yl}methanol (0.475 g, 1.14 mmol) and tributylphosphine (0.453 mL, 1.82 mmol) in toluene (18 mL) was stirred, 1,1'-(azodicarbonyl)dipiperidine (0.459 g, 1.82 mmol) was added, and the mixture was stirred at room temperature for 1 hr under nitrogen atmosphere. Hexane (9 mL) was added to the reaction mixture, the precipitated insoluble substance was filtered off, and the filtrate was concentrated under reduced pressure. The residue was purified by silica gel column chromatography (ethyl acetate:hexane=30:70-70:30) to give the title compound (0.622 g, yield 89%) as a yellow oil.

MS m/z 607 (M+H)$^+$.

Example 24

[(3S)-6-({3',5'-dichloro-2',6'-dimethyl-4'-[3-(methylsulfonyl)propoxy]biphenyl-3-yl}methoxy)-2,3-dihydro-1-benzofuran-3-yl]acetic acid

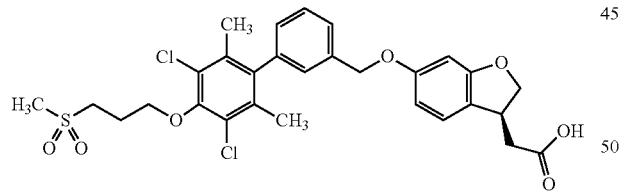

To a solution of methyl [(3S)-6-({3',5'-dichloro-2',6'-dimethyl-4'-[3-(methylsulfonyl)propoxy]biphenyl-3-yl}methoxy)-2,3-dihydro-1-benzofuran-3-yl]acetate (0.617 g, 1.02 mmol) in a mixed solvent of methanol (2 mL) and tetrahydrofuran (4 mL) was added 2 M aqueous sodium hydroxide solution (1 mL), and the mixture was stirred at 50° C. for 2 hr. The reaction mixture was diluted with water, acidified with 10% aqueous citric acid solution, and extracted with ethyl acetate. The extract was washed with saturated brine, dried over anhydrous magnesium sulfate, and concentrated under reduced pressure. The precipitated crystals were recrystallized from heptane-ethyl acetate to give the title compound (0.520 g, yield 86%) as colorless crystals.

MS m/z 593 (M+H)$^+$.

Elemental analysis for $C_{29}H_{30}Cl_2O_7S$

Calculated: C, 58.69; H, 5.09.

Found: C, 58.69; H, 4.99.

Example 25 methyl [(3S)-6-({2',6'-diethyl-4'-[3-(methylsulfonyl)propoxy]biphenyl-3-yl}methoxy)-2,3-dihydro-1-benzofuran-3-yl]acetate

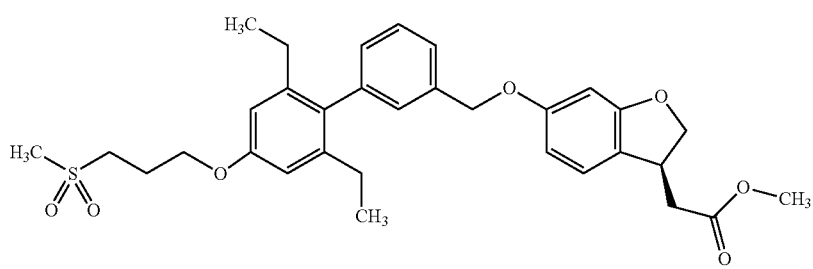

A solution of methyl [(3S)-6-hydroxy-2,3-dihydro-1-benzofuran-3-yl]acetate (0.208 g, 1.00 mmol), {2',6'-diethyl-4'-[3-(methylsulfonyl)propoxy]biphenyl-3-yl}methanol (0.377 g, 1.00 mmol) and tributylphosphine (0.399 mL, 1.60 mmol) in toluene (16 mL) was stirred, 1,1'-(azodicarbonyl)dipiperidine (0.404 g, 1.60 mmol) was added, and the mixture was stirred at room temperature for 2 hr under nitrogen atmosphere. Hexane (8 mL) was added to the reaction mixture, the precipitated insoluble substance was filtered off, and the filtrate was concentrated under reduced pressure. The residue was purified by silica gel column chromatography (ethyl acetate:hexane=30:70-70:30) to give the title compound (0.526 g, yield 93%) as a yellow oil.

MS m/z 567 (M+H)$^+$.

Example 26

[(3S)-6-({2',6'-diethyl-4'-[3-(methylsulfonyl)propoxy]biphenyl-3-yl}methoxy)-2,3-dihydro-1-benzofuran-3-yl]acetic acid

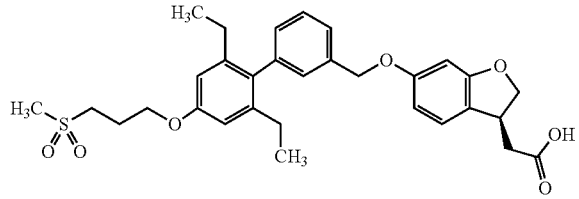 [SMILES: CCc1cc(OCCCS(C)(=O)=O)cc(CC)c1-c1cccc(COc2ccc3c(c2)OC[C@H]3CC(=O)O)c1]

To a solution of methyl [(3S)-6-({2',6'-diethyl-4'-[3-(methylsulfonyl)propoxy]biphenyl-3-yl}methoxy)-2,3-dihydro-1-benzofuran-3-yl]acetate (0.521 g, 0.919 mmol) in a mixed solvent of methanol (2 mL) and tetrahydrofuran (4 mL) was added 2 M aqueous sodium hydroxide solution (1 mL), and the mixture was stirred at 50° C. for 1.5 hr. The reaction mixture was diluted with water, acidified with 10% aqueous citric acid solution, and extracted with ethyl acetate. The extract was washed with saturated brine, dried over anhydrous magnesium sulfate, and concentrated under reduced pressure. The precipitated crystals were recrystallized from heptane-ethyl acetate to give the title compound (0.413 g, yield 81%) as colorless crystals.

MS m/z 553 (M+H)$^+$.

$^1$H NMR (CDCl$_3$) δ: 0.98 (6H, t, J=7.5 Hz), 2.22-2.42 (6H, m), 2.55-2.66 (1H, m), 2.75-2.85 (1H, m), 2.97 (3H, s), 3.25-3.33 (2H, m), 3.74-3.86 (1H, m), 4.15 (2H, t, J=5.7 Hz), 4.28 (1H, dd, J=9.1, 6.1 Hz), 4.75 (1H, t, J=9.1 Hz), 5.07 (2H, s), 6.43-6.51 (2H, m), 6.66 (2H, s), 7.04 (1H, d, J=8.3 Hz), 7.06-7.12 (1H, m), 7.18 (1H, s), 7.35-7.45 (2H, m).

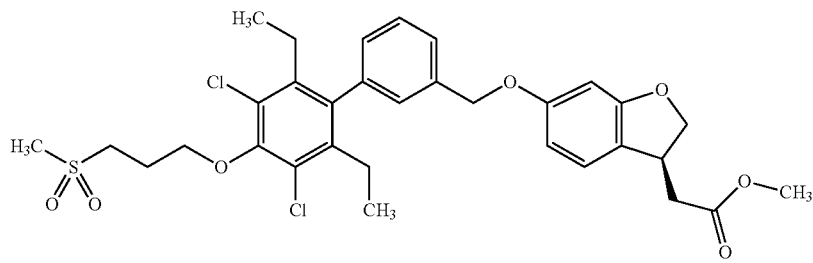

In the same manner as in Example 23, the title compound was obtained as a colorless oil from methyl [(3S)-6-hydroxy-2,3-dihydro-1-benzofuran-3-yl]acetate and {3',5'-dichloro-2',6'-diethyl-4'-[3-(methylsulfonyl)propoxy]biphenyl-3-yl}methanol. yield 74%.

MS m/z 635 (M+H)$^+$.

Example 28

[(3S)-6-({3',5'-dichloro-2',6'-diethyl-4'-[3-(methylsulfonyl)propoxy]biphenyl-3-yl}methoxy)-2,3-dihydro-1-benzofuran-3-yl]acetic acid

Example 27 methyl [(3S)-6-({3',5'-dichloro-2',6'-diethyl-4'-[3-(methylsulfonyl)propoxy]biphenyl-3-yl}methoxy)-2,3-dihydro-1-benzofuran-3-yl]acetate

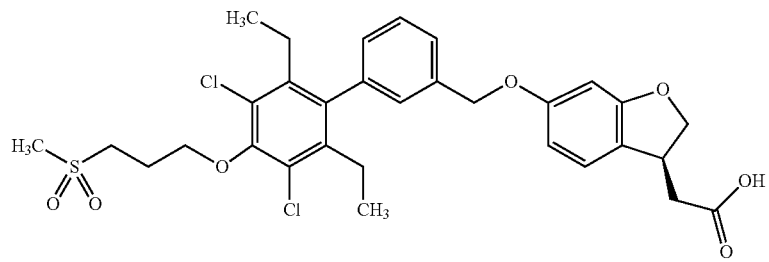 [SMILES: CCc1c(Cl)c(OCCCS(C)(=O)=O)c(Cl)c(CC)c1-c1cccc(COc2ccc3c(c2)OC[C@H]3CC(=O)O)c1]

In the same manner as in Example 24, the title compound was obtained as colorless crystals from methyl [(3S)-6-({3',5'-dichloro-2',6'-diethyl-4'-[3-(methylsulfonyl)propoxy]biphenyl-3-yl}methoxy)-2,3-dihydro-1-benzofuran-3-yl]acetate. yield 66%.
MS m/z 621 (M+H)$^+$.

Example 29 methyl [(3S)-6-({2',6'-dimethyl-4'-[3-(methylsulfonyl)propoxy]-6-phenoxybiphenyl-3-yl}methoxy)-2,3-dihydro-1-benzofuran-3-yl]acetate

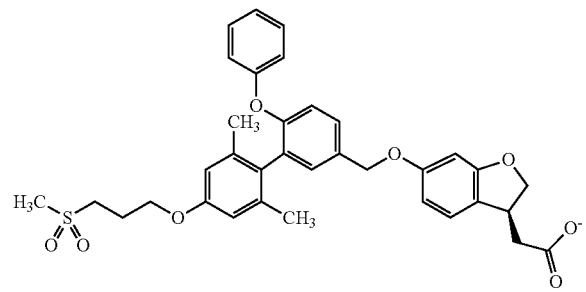 [SMILES: Cc1cc(OCCCS(C)(=O)=O)cc(C)c1-c1cc(COc2ccc3c(c2)OC[C@H]3CC(=O)[O-])ccc1Oc1ccccc1]

In the same manner as in Example 5, the title compound was obtained as a colorless oil from methyl [(3S)-6-({2',6'-dimethyl-4'-[3-(methylthio)propoxy]-6-phenoxybiphenyl-3-yl}methoxy)-2,3-dihydro-1-benzofuran-3-yl]acetate. yield 99%.
MS m/z 631 (M+H)$^+$.

Example 30

[(3S)-6-({2',6'-dimethyl-4'-[3-(methylsulfonyl)propoxy]-6-phenoxybiphenyl-3-yl}methoxy)-2,3-dihydro-1-benzofuran-3-yl]acetic acid 0.5 calcium salt

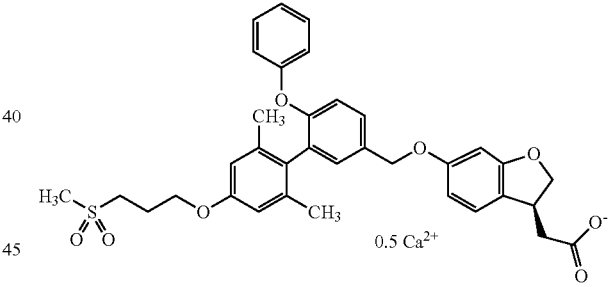

To a solution of methyl [(3S)-6-({2',6'-dimethyl-4'-[3-(methylsulfonyl)propoxy]-6-phenoxybiphenyl-3-yl}methoxy)-2,3-dihydro-1-benzofuran-3-yl]acetate (0.371 g, 0.588 mmol) in a mixed solvent of methanol (2 mL) and tetrahydrofuran (4 mL) was added 2 M aqueous sodium hydroxide solution (0.6 mL), and the mixture was stirred at 50° C. for 2 hr. The reaction mixture was diluted with water, acidified with 1 M hydrochloric acid, and extracted with ethyl acetate. The extract was washed with saturated brine, dried over anhydrous magnesium sulfate, and concentrated under reduced pressure. The residue was purified by silica gel column chromatography (ethyl acetate:hexane=40:60-100:0) to give an oil (0.342 g). The obtained oil was dissolved in a mixed solvent of methanol (2 mL) and water (1 mL), and 1 M aqueous sodium hydroxide solution (0.555 mL) was added. 1 M Aqueous calcium chloride solution (0.333 mL) was added thereto. The precipitated solid was collected by filtration, washed with water, and dried to give the title compound (0.256 g, yield 68%) as a colorless powder.

$^1$H NMR (DMSO-d$_6$) δ: 1.95 (6H, s), 2.01-2.29 (3H, m), 2.43-2.55 (1H, m), 3.01 (3H, s), 3.20-3.29 (2H, m), 3.62-3.74 (1H, m), 4.04 (2H, t, J=6.0 Hz), 4.11-4.19 (1H, m), 4.68 (1H, t, J=8.9 Hz), 4.99 (2H, s), 6.36-6.43 (2H, m), 6.64 (2H, s), 6.79-6.85 (2H, m), 6.95 (1H, d, J=8.5 Hz), 7.00-7.12 (2H, m), 7.16 (1H, d, J=2.0 Hz), 7.23-7.31 (2H, m), 7.37 (1H, dd, J=8.5, 2.0 Hz).

Example 31 methyl [(3S)-6-({2',6'-dimethyl-4'-[3-(methylsulfonyl)propoxy]-6-(phenoxymethyl)biphenyl-3-yl}methoxy)-2,3-dihydro-1-benzofuran-3-yl]acetate

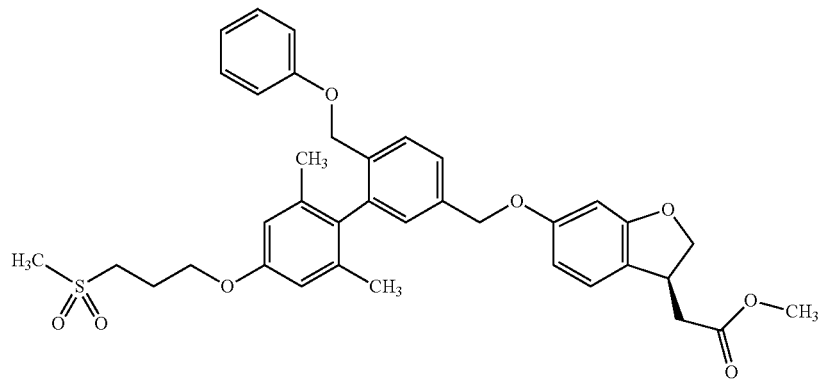

In the same manner as in Example 1, the title compound was obtained as a colorless oil from {2',6'-dimethyl-4'-[3-(methylsulfonyl)propoxy]-6-(phenoxymethyl)biphenyl-3-yl}methanol and methyl [(3S)-6-hydroxy-2,3-dihydro-1-benzofuran-3-yl]acetate. yield 72%.

$^1$H NMR (CDCl$_3$) δ: 1.95 (6H, s), 2.28-2.41 (2H, m), 2.55 (1H, dd, J=16.5, 9.1 Hz), 2.74 (1H, dd, J=16.5, 5.4 Hz), 2.95 (3H, s), 3.22-3.31 (2H, m), 3.71 (3H, s), 3.74-3.87 (1H, m), 4.11 (2H, t, J=5.7 Hz), 4.26 (1H, dd, J=9.0, 6.1 Hz), 4.64 (2H, s), 4.75 (1H, t, J=9.0 Hz), 5.06 (2H, s), 6.43-6.50 (2H, m), 6.62 (2H, s), 6.77-6.84 (2H, m), 6.87-6.95 (1H, m), 7.01 (1H, d, J=7.9 Hz), 7.12 (1H, d, J=1.5 Hz), 7.18-7.26 (2H, m), 7.44 (1H, dd, J=7.9, 1.8 Hz), 7.65 (1H, d, J=7.9 Hz).

Example 32

[(3S)-6-({2',6'-dimethyl-4'-[3-(methylsulfonyl)propoxy]-6-(phenoxymethyl)biphenyl-3-yl}methoxy)-2,3-dihydro-1-benzofuran-3-yl]acetic acid

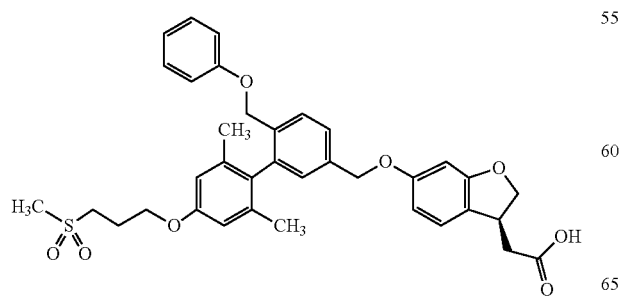

In the same manner as in Example 2, the title compound was obtained as a colorless oil from methyl [(3S)-6-({2',6'-dimethyl-4'-[3-(methylsulfonyl)propoxy]-6-(phenoxymethyl)biphenyl-3-yl}methoxy)-2,3-dihydro-1-benzofuran-3-yl]acetate. yield 99%.

$^1$H NMR (CDCl$_3$) δ: 1.95 (6H, s), 2.28-2.42 (2H, m), 2.61 (1H, dd, J=16.7, 9.1 Hz), 2.80 (1H, dd, J=16.7, 5.3 Hz), 2.95 (3H, s), 3.21-3.33 (2H, m), 3.73-3.88 (1H, m), 4.11 (2H, d, J=7.2 Hz), 4.28 (1H, dd, J=9.1, 6.1 Hz), 4.64 (2H, s), 4.75 (1H, t, J=8.9 Hz), 5.06 (2H, s), 6.42-6.52 (2H, m), 6.62 (2H, s), 6.77-6.97 (3H, m), 7.00-7.26 (4H, m), 7.40-7.50 (1H, m), 7.65 (1H, d, J=8.0 Hz).

Example 33 methyl [(3S)-6-({6-(benzyloxy)-4-fluoro-2',6'-dimethyl-4'-[3-(methylsulfonyl)propoxy]biphenyl-3-yl}methoxy)-2,3-dihydro-1-benzofuran-3-yl]acetate

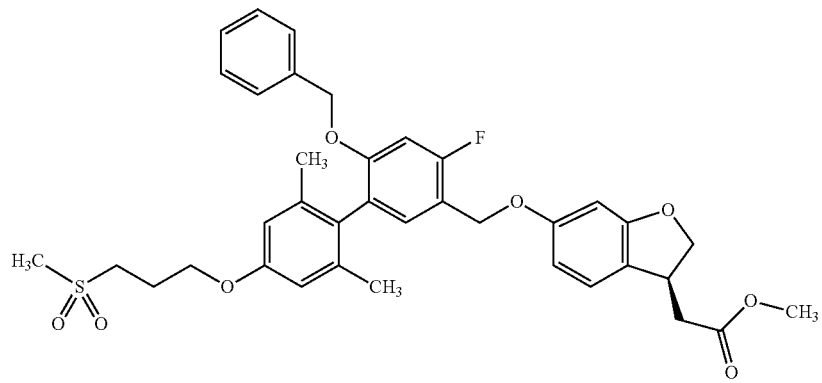

In the same manner as in Example 5, the title compound was obtained as a colorless oil from methyl [(3S)-6-({6-(benzyloxy)-4-fluoro-2',6'-dimethyl-4'-[3-(methylthio)propoxy]biphenyl-3-yl}methoxy)-2,3-dihydro-1-benzofuran-3-yl]acetate. yield 78%.

$^1$H NMR (CDCl$_3$) δ: 1.97 (6H, s), 2.29-2.41 (2H, m), 2.54 (1H, dd, J=16.3, 9.1 Hz), 2.73 (1H, dd, J=16.3, 5.3 Hz), 2.95 (3H, s), 3.22-3.32 (2H, m), 3.71 (3H, s), 3.73-3.86 (1H, m), 4.12 (2H, t, J=5.7 Hz), 4.25 (1H, dd, J=9.1, 6.1 Hz), 4.73 (1H, t, J=9.1 Hz), 5.01 (4H, s), 6.41-6.50 (2H, m), 6.64 (2H, s), 6.74 (1H, d, J=11.7 Hz), 7.00 (1H, d, J=8.0 Hz), 7.09 (1H, d, J=8.7 Hz), 7.14-7.34 (5H, m).

Example 34

[(3S)-6-({6-(benzyloxy)-4-fluoro-2',6'-dimethyl-4'-[3-(methylsulfonyl)propoxy]biphenyl-3-yl}methoxy)-2,3-dihydro-1-benzofuran-3-yl]acetic acid

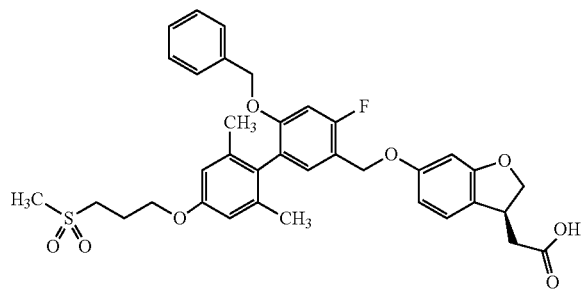 [SMILES: Cc1cc(OCCCS(C)(=O)=O)cc(C)c1-c1cc(COc2ccc3c(c2)OC[C@H]3CC(=O)O)c(F)cc1OCc1ccccc1]

In the same manner as in Example 2, the title compound was obtained as a colorless amorphous powder from methyl [(3S)-6-({6-(benzyloxy)-4-fluoro-2',6'-dimethyl-4'-[3-(methylsulfonyl)propoxy]biphenyl-3-yl}methoxy)-2,3-dihydro-1-benzofuran-3-yl]acetate. yield 81%.

$^1$H NMR (CDCl$_3$) δ: 1.97 (6H, s), 2.29-2.41 (2H, m), 2.60 (1H, dd, J=16.6, 9.1 Hz), 2.79 (1H, dd, J=16.6, 5.6 Hz), 2.95 (3H, s), 3.23-3.31 (2H, m), 3.74-3.86 (1H, m), 4.12 (2H, t, J=5.7 Hz), 4.28 (1H, dd, J=9.1, 6.0 Hz), 4.75 (1H, t, J=9.1 Hz), 5.02 (4H, s), 6.42-6.50 (2H, m), 6.64 (2H, s), 6.74 (1H, d, J=11.7 Hz), 7.04 (1H, d, J=8.1 Hz), 7.09 (1H, d, J=8.7 Hz), 7.14-7.21 (2H, m), 7.22-7.34 (3H, m).

| Formulation Example 1 (production of capsule) | |
|---|---|
| 1) compound of Example 1 | 30 mg |
| 2) microcrystalline cellulose | 10 mg |
| 3) lactose | 19 mg |
| 4) magnesium stearate | 1 mg |
| total | 60 mg |

The above-mentioned 1), 2), 3) and 4) are mixed and filled in a gelatin capsule.

| Formulation Example 2 (production of tablet) | |
|---|---|
| 1) compound of Example 1 | 30 g |
| 2) lactose | 50 g |
| 3) corn starch | 15 g |
| 4) carboxymethylcellulose calcium | 44 g |
| 5) magnesium stearate | 1 g |
| 1000 tablets total | 140 g |

The total amount of the above-mentioned 1), 2) and 3) and 30 g of 4) are kneaded with water, vacuum dried and granulated. The granulated powder is mixed with 14 g of 4) and 1 g of 5) and tableted with a tableting machine. In this way, 1000 tablets containing 30 mg of the compound of Example 1 per tablet are obtained.

Experimental Example 1

Receptor Function Modulating Action (Agonist Action) on Human-Derived GPR40

A CHO cell line stably expressing human-derived GPR40 was used for determining the agonist activity. Unless particularly described, the CHO cell line was cultured in α-MEM medium (Invitrogen or Wako Pure Chemical Industries, Ltd.) supplemented with 10% dialyzed fetal calf serum (TRA Thermo Electron).

One day before the assay, the cells cultured to near confluence were rinsed with PBS (Invitrogen), detached using 0.5 mM EDTA (Wako Pure Chemical Industries, Ltd.) and recovered by centrifugation. The obtained cells were counted and diluted to 3×10$^5$ cells per 1 mL medium. The cells were dispensed to a 96-well black clear bottom plate (Coster) by 100 μL per well and cultured overnight in a CO$_2$ incubator. To the CHO cells prepared in this manner were added various test compounds, and variation in the intracellular calcium concentration was measured using FLIPR (Molecular Device) or Cell Lux (PerkinElmer). For measurement of variation in the intracellular calcium concentration using FLIPR or Cell Lux, the following pretreatment was performed.

To add fluorescence dye Fluo3-AM (Molecular Device) to the cells, fatty acid-free BSA was added to α-MEM medium to the final concentration of 0.1% to give an assay buffer. A fluorescence dye solution was prepared by dissolving 500 mM Probenecid in 1N NaOH, adding the solution to the assay buffer to the final concentration of 2.5 mM, and the resulting solution (10 mL) was added to 1 vial of component A (Molecular Device). The medium of the 96 well black clear bottom plate into which the CHO cells had been sown one day before the assay was removed. The cells were washed with D-PBS(−), 50 L of the assay buffer (α-MEM medium added with fatty acid-free BSA, final concentration 0.1%) was further added thereto and the cells were cultured at 37° C. for 60 min in a CO$_2$ incubator. Then, a fluorescence dye solution was dispensed by 100 μL per well, and the cells were cultured in a CO$_2$ incubator for 1 hr to allow intake of the fluorescence dye.

During this time, the test compound was diluted to a given concentration with the assay buffer, and dispensed to a polypropylene 96-well plate (sample plate) by 100 μL. The cell plate and the sample plate were simultaneously set in the FLIPR or Cell Lux. After the foregoing pretreatment, variation in the intracellular calcium concentration after addition of 50 μL of various test compounds was measured using FLIPR or Cell Lux. From the results, the agonist activity of each compound (1 μM) was calculated as a relative activity value when the activity of 10 μM γ-linolenic acid (GPR40 agonist) was 100%. The results are shown in Table 1.

FLIPR was employed for the assay of compounds of Examples 2, 6, 8, 10, 11 and 13, and Cell Lux was employed for the assay of compounds of Examples 19, 20, 22, 24, 26, 28, 30, 32 and 34.

TABLE 1

| Compound No. | Relative activity value |
|---|---|
| Example 2 | 107 |
| Example 6 | 102 |
| Example 8 | 112 |
| Example 10 | 114 |
| Example 11 | 120 |

TABLE 1-continued

| Compound No. | Relative activity value |
|---|---|
| Example 13 | 125 |
| Example 19 | 118 |
| Example 20 | 118 |
| Example 22 | 121 |
| Example 24 | 96 |
| Example 26 | 101 |
| Example 28 | 92 |
| Example 30 | 108 |
| Example 32 | 104 |
| Example 34 | 119 |
| γ-linoleic acid | 100 |

INDUSTRIAL APPLICABILITY

The compounds of the present invention have a superior GPR40 receptor function modulating action and are useful as insulin secretagogues or agents for the prophylaxis or treatment of diabetes and the like.

This application is based on patent application No. 177099/2006 filed in Japan, the contents of which are hereby incorporated by reference.

The invention claimed is:

1. A pharmaceutical preparation comprising [(3S)-6-({2',6'-dimethyl-4'-[3-(methylsulfonyl)propoxy]biphenyl-3-yl}methoxy)-2,3-dihydro-1-benzofuran-3-yl]acetic acid or a salt thereof and a pharmacologically acceptable carrier.

* * * * *